US011459568B2

(12) United States Patent
Messina et al.

(10) Patent No.: US 11,459,568 B2
(45) Date of Patent: Oct. 4, 2022

(54) TARGETING MICRORNA-101-3P IN CANCER THERAPY

(71) Applicant: University of Massachusetts, Boston, MA (US)

(72) Inventors: Louis M. Messina, Westborough, MA (US); Guodong Tie, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 627 days.

(21) Appl. No.: 16/332,588

(22) PCT Filed: Oct. 31, 2017

(86) PCT No.: PCT/US2017/059367
§ 371 (c)(1),
(2) Date: Mar. 12, 2019

(87) PCT Pub. No.: WO2018/081817
PCT Pub. Date: May 3, 2018

(65) Prior Publication Data
US 2021/0277402 A1    Sep. 9, 2021

Related U.S. Application Data

(60) Provisional application No. 62/415,269, filed on Oct. 31, 2016.

(51) Int. Cl.
| C07H 21/02 | (2006.01) |
| C07H 21/04 | (2006.01) |
| C12N 15/113 | (2010.01) |
| A61K 35/28 | (2015.01) |
| A61K 45/06 | (2006.01) |

(52) U.S. Cl.
CPC .......... *C12N 15/1137* (2013.01); *A61K 35/28* (2013.01); *A61K 45/06* (2013.01); *C12N 15/113* (2013.01); *C12N 15/1135* (2013.01); *C12N 2310/11* (2013.01); *C12N 2310/14* (2013.01); *C12N 2310/141* (2013.01); *C12N 2310/531* (2013.01)

(58) Field of Classification Search
CPC .................. C12N 15/113; C12N 2310/141
See application file for complete search history.

(56) References Cited

U.S. PATENT DOCUMENTS

| 7,741,345 | B2 | 6/2010 | Cannizzaro et al. |
| 8,790,655 | B2 | 7/2014 | Carson et al. |
| 8,795,678 | B2 | 8/2014 | Liang et al. |
| 10,034,901 | B2 | 7/2018 | Messina et al. |
| 2011/0236362 | A1 | 9/2011 | Watarai et al. |
| 2011/0236894 | A1 | 9/2011 | Rao et al. |
| 2012/0190731 | A1 | 7/2012 | Messina et al. |
| 2012/0272346 | A1 | 10/2012 | Stillman et al. |
| 2013/0323220 | A1 | 12/2013 | Joung et al. |
| 2015/0153349 | A1 | 6/2015 | Galon et al. |
| 2016/0213715 | A1 | 7/2016 | Messina et al. |
| 2019/0233828 | A1 | 8/2019 | Messina |
| 2020/0316123 | A1 | 10/2020 | Messina et al. |

FOREIGN PATENT DOCUMENTS

| WO | WO 2007135195 | 11/2007 | |
| WO | WO 2009/114547 | 9/2009 | |
| WO | WO2009/145399 | 12/2009 | |
| WO | WO 2009/146399 | 12/2009 | |
| WO | WO 2011/022316 A1 * | 2/2011 | ........... C12N 15/113 |
| WO | WO 2013/173223 | 11/2013 | |
| WO | WO 2015/113922 | 8/2015 | |
| WO | WO 2016/014544 | 1/2016 | |
| WO | WO 2016/109668 | 7/2016 | |

OTHER PUBLICATIONS

Ma et al. (Cancer Research, Aug. 2015, 75, 15, 1-7).*
Sheng et al. (Arch Virol, 2014, 159:2397-2410).*
Liu et al. (Oncotarget, vol. 7, No. 23, 35188-35198.*
PCT International Preliminary Report on Patentability in International Appln. No. PCT/US2018/040642, dated Aug. 4, 2020, 11 pages.
U.S. Appl. No. 15/004,132, filed Jan. 22, 2016, Louis M. Messina.
U.S. Appl. No. 15/538,690, filed Jun. 22, 2017, Louis M. Messina.
U.S. Appl. No. 16/231,129, filed Dec. 21, 2018, Louis M. Messina.
EP Office Action in European Appln. No. 16740821.0, dated Jan. 27, 2020, 4 pages.
EP Supplementary European Search Report in European Appln. No. 17865070.1, dated Jun. 25, 2020.
Fan et al., "MicroRNA-101-3p reverses gemcitabine resistance by inhibition of ribonucleotide reductase M1 in pancreatic cancer," Cancer Letters, Apr. 1, 2016, 373(1):130-7.
Alder et al., "Kruppel-like factor 4 is essential for inflammatory monocyte differentiation in vivo," J. Immunol., Apr. 2008, 180:5645-5652.
Alexandrescu et al., "Immunotherapy for Melanoma: Current Status and Perspectives," J. Immunother., Jul.-Aug. 2010, 33(6):570-590.
American Diabetes Association, "2. Classification and Diagnosis of Diabetes," Diabetes Care, 2015, 38(Supplement 1):S8-S16.
American Diabetes, "11. Older Adults: Standards of Medical Care in Diabetes—2018," Diabetes Care, 2018, 41(Suppl 1):S119-S125.
Bannon et al., "Diabetes induces stable intrinsic changes to myeloid cells that contribute to chronic inflammation during wound healing in mice," Dis. Model Mech., Nov. 2013, 6(6):1434-1447.
Bedard and Krause, "The NOX family of ROS-generating NADPH oxidases: physiology and pathophysiology," Physiol. Rev., Jan. 2007, 87(1):245-313.
Bendelac et al., "The biology of NKT cells," Annu. Rev. Immunol., 2007, 25:297-336.
Bennouna et al, "Phase I study of bromohydrin pyrophosphate (BrHPP, IPH 1101), a Vγ9Vδ2 T lymphocyte agonist in patients with solid tumors," Cancer Immunol. Immunother., 2010, 59:1521-1530.
Berezhnoy et al., "A clinically useful approach to enhance immunological memory and antitumor immunity," Oncoimmunology, May 2014, 14(3):e28811-3.

(Continued)

*Primary Examiner* — Amy H Bowman
(74) *Attorney, Agent, or Firm* — Fish & Richardson P.C.

(57) ABSTRACT

Methods and compositions for treating cancer, e.g., colorectal cancer, using a miR-101-3p inhibitor.

20 Claims, 34 Drawing Sheets

Specification includes a Sequence Listing.

(56) References Cited

OTHER PUBLICATIONS

Boesch et al., "Heterogeneity of cancer stem cells: rationale for targeting the stem cell niche," Biochimica Biophysica Acta, Dec. 2016, 1866(2):276-289.
Bollino and Webb, "Chimeric antigen receptor-engineered natural killer and natural killer T cells for cancer immunotherapy," Transl. Res., Sep. 2017, 187:32-43.
Bonomini et al., "Metabolic syndrome, aging and involvement of oxidative stress," Aging Dis., Mar. 2015, 6(2):109-120.
Boulton et al., "The global burden of diabetic foot disease," Lancet, Nov. 2005, 366(9498):1719-1724.
Brem and Tomic-Canic, "Cellular and molecular basis of wound healing in diabetes," J. Clin. Invest., May 2007, 117(5):1219-1222.
Brem et al., "Evidence-based protocol for diabetic foot ulcers," Plast. Reconstr. Surg., Jun. 2006, 117(7 Suppl):193S-209S.
Brem et al., "The synergism of age and db/db genotype impairs wound healing," Exp. Gerontol., Jun. 2007, 42(6):523-531.
Breslin et al., "Mouse blood monocytes: Standardizing their identification and analysis using CD11," J. Immunol. Methods., Apr. 2013, 390(1-2):1-8.
Bryder et al., "Interleukin-3 supports expansion of long-term multilineage repopulating activity after multiple stem cell divisions in vitro," Blood, Sep. 2000, 96(5):1748-1755.
Buttigieg et al., "NOX2 (gp91phox) is a predominant O2 sensor in a human airway chemoreceptor cell line: biochemical, molecular, and electrophysiological evidence," Am. J. Physiol. Lung Cell. Mol. Physiol., Oct. 2012, 303(7):L598-L607.
Caravaggi et al., "Management of ischemic diabetic foot," J. Cardiovasc., Surg., Dec. 2013, 54(6):737-754.
Castellano et al., "Constrained analogues of procaine as novel small molecule inhibitors of DNA methyltransferase-1," J. Med. Chem., Apr. 2008, 51(7):2321-2325.
Castillo-Aguilera et al., "DNA methylation targeting: the DNMT/ HMT crosstalk challenge," Biomolecules, Mar. 2017, 7(1): 3.
Chambers et al., "Aging hematopoietic stem cells decline in function and exhibit epigenetic dysregulation," PLoS Biol., Aug. 2007, 5(8):e201:1750-1762.
Chapman et al., "TET-catalyzed 5-hydroxymethylcytosine regulates gene expression in differentiating colonocytes and colon cancer," Sci Rep., Dec. 2015, 5:17568.
Chen et al., "Absence of CD4 or CD8 lymphocytes changes infiltration of inflammatory cells and profiles of cytokine expression in skin wounds, but does not impair healing," Exp. Dermatol., Mar. 2014, 23(3):189-194.
Chen et al., "TET2 promotes histone O-GlcNAcylation during gene transcription," Nature, Jan. 2013, 493(7433):561-564.
Chien et al., "γδT cells: first line of defense and beyond," Annu. Rev. Immunol., 2014, 32:121-155.
Choo et al., "MicroRNA-5p and -3p co-expression and crosstargeting in colon cancer cells," J. Biomed. Sci., Oct. 2014, 21:95, 14 pages.
Cieslewicz et al., "Targeted delivery of proapoptotic peptides to tumor-associated macrophages improves survival," PNAS, Oct. 2013, 110(40):15919-15924.
Cimmino et al., "TET1 is a tumor suppressor of hematopoietic malignancy," Nat. Immunol., Aug. 2015, 16:6(8)53-62.
Coffman et al., "Endothelin receptor-A is required for the recruitment of antitumor T cells and modulates chemotherapy induction of cancer stem cells," Cancer Biol. Ther., Feb. 2013, 14(2):184-192.
Corpuz et al., "Differential responsiveness of Innate-like IL-17- and IFN-γ-producing γδ T cells to homeostatic cytokines," J. Immunol., Jan. 2016, 196(2):645-654.
Crowe et al., "A critical role for natural killer T cells in immunosurveillance of methylcholanthrene-induced sarcomas," J. Exp. Med., Jul. 2002, 196(1):119-127.
Cubbon et al., "Effects of insulin resistance on endothelial progenitor cells and vascular repair," Clin. Sci., Aug. 2009, 117(5):173-190.
Cui et al., "Upregulated lncRNA SNHG1 contributes to progression of non-small cell lung cancer through inhibition of mlR-101-3p and activation of Wnt/P-catenin signaling pathway," Oncotarget, Mar. 2017, 8(11): 17785-17794.
Cullen et al., "Hematopoietic stem cell development: an epigenetic journey," Curr. Top. Dev. Biol., 2014, 107:39-75.
Daigneault et al., "The identification of markers of macrophage differentiation in PMA-stimulated THP-1 cells and monocytederived macrophages," PLoS One, Jan. 2010, 5(1):e8668, 31 pages.
Dakic et al., "PU.1 regulates the commitment of adult hematopoietic progenitors and restricts granulopoiesis," J. Exp. Med., May 2005, 201(9):1487-1502.
Deplus et al., "TET2 and TET3 regulate GlcNAcylation and H3K4 methylation through OCT and SET1/COMPASS," Mar. 2013, Embo J., 32(5):645-655.
Dhodapkar et al., "A reversible defect in natural killer T cell function characterizes the progression of premalignant to malignant multiple myeloma," J Exp. Med., Jun. 2003, 197(12):1667-1676.
Diebold et al., "NOX2 as a target for drug development: indications, possible complications, and progress," Antioxid. Redox. Signal., Aug. 2015, 23(5):375-405.
Dieterlen-Lievre, "Hematopoiesis: progenitors and their genetic program," Curr. Biol., Oct. 1998, 8(20):R727-R730.
Donovan et al., "Drugs for gestational diabetes," Australian Prescriber, Oct. 2010, 33(5):141-144.
Drechsler et al., "Hyperlipidemia-triggered neutrophilia promotes early atherosclerosis," Circulation, Nov. 2010, 122(18):1837-1845.
Dunn et al., "Cancer immunoediting: from immunosurveillance to tumor escape," Nat. Immunol., Nov. 2002, 3(11):991-998.
Dunn et al., "Interferons, immunity and cancer immunoediting," Nat. Rev. Immunol., Nov. 2006, 6(11): 836-848.
Dunn et al., "The immunobiology of cancer immunosurveillance and immunoediting," Immunity, Aug. 2004, 21(2):137-148.
Eggermont et al., "Anti-CTLA-4 antibody adjuvant therapy in melanoma," Semin. Oncol., Oct. 2010, 37(5):455-459.
ENSEMBL. Gene: DNMT1 ENSMUSG00000004099. Jul. 2018; downloaded from the internet <https://uswest.ensembl.org/Mus_musculus/Gene/Sequence?g=ENSMUSG00000004099;r=9:20907209-20959888>on Sep. 21, 2018, pp. 1-16.
Escamilla-Tilch et al., "The interplay between pathogen-associated and danger-associated molecular patterns: an inflammatory code in cancer?," Immunol. Cell Biol., Nov.-Dec. 2013, 91(10):601-610.
Esteve et al., "Direct interaction between DNMT1 and G9a coordinates DNA and histone methylation during replication," Genes Dev., Nov. 2006, 20(22):3089-3103.
European Search Report and Written Opinion in International Application No. 16740821.0, dated Jul. 25, 2018, 8 pages.
Fadini et al., "An unbalanced monocyte polarisation in peripheral blood and bone marrow of patients with type 2 diabetes has an impact on microangiopathy," Diabetologia, Aug. 2013, 56:(8):1856-1866.
Fagan et al., "Laccaic acid A is a direct DNA-competitive inhibitor of DNA methyltransferase 1," J. Biol. Chemistry, Aug. 2013, 288(33):23858-23867.
Falanga, "Wound healing and its impairment in the diabetic foot," Lancet, Nov. 2005, 366(9498):1736-1743.
Fan et al., "DNA methyltransferase 1 knockdown induces silenced CDH1 gene reexpression by demethylation of methylated CpG in hepatocellular carcinoma cell line SMMC-7721," Eur. J. Gastroenterol. Hepatol., Nov. 2007, 19(11):952-961.
Feinberg et al., "The Kruppel-like factor KLF4 is a critical regulator of monocyte differentiation," EMBO J., Sep. 2007, 26(18):4138-4148.
Fisher et al., "γ cells for cancer immunotherapy: a systematic review of clinical trials," Oncoimmunology, Jan. 2014, 3(1): e27572.
Folli et al., "Altered insulin receptor signalling and β-cell cycle dynamics in type 2 diabetes mellitus," PLoS One, 2011, 6(11):e28050, 11 pages.
Font-Burgada et al., "Obesity and cancer: the oil that feeds the flame," Cell Metab., Jan. 2016, 23(1):48-62.
Foulks et al., "Epigenetic drug discovery: targeting DNA methyltransferases," J. Biol. Screen., Jan. 2012, 17(1):2-17.

(56) References Cited

OTHER PUBLICATIONS

Francke et al., "Generation of mature murine monocytes from heterogeneous bone marrow and description of their properties," J. Histochem. Cytochem., Sep. 2011, 59(9):813-825.
Frank et al., "Autophagic digestion of Leishmania major by host macrophages is associated with differential expression of BNIP3, CTSE, and the miRNAs miR-101c, miR-129, and miR-210," Parasit. Vectors, Jul. 2015, 8:404.
Gallagher et al., "Epigenetic changes in bone marrow progenitor cells influence the inflammatory phenotype and alter wound healing in type 2 diabetes," Diabetes, Apr. 2015, 64(4):1420-1430.
Galluzi et al., "Trial watch: experimental Toll-like receptor agonists for cancer therapy," Oncoimmunol., Aug. 2012, 1(5): 699-716.
Galon et al., "Cancer classification using the immunoscore: a worldwide task force," J. Transl. Med., Oct. 2012, 10:205-214.
Ganesan and Bakhshi, "Systemic therapy for melanoma," Natl. Med. J. India., 2010, 23(1):21-7.
Gangaraju and Lin, "MicroRNAs: key regulators of stem cells," Nat. Rev. Mol. Cell. Biol., Feb. 2009, 10(2):116-125.
Garbe et al., "TCR and Notch synergize in alphabeta versus gammadelta lineage choice," Trends Immunol., Mar. 2007, 28(3):124-131.
Geiger et al., "Hematopoietic stem cell aging," Curr. Opin. Immunol., Aug. 2014, 29:86-92.
Geissmann et al., "Development of monocytes, macrophages, and dendritic cells," Science, Feb. 2010, 327(5966):656-661.
Georgantas et al., "Microarray and serial analysis of gene expression analyses identify known and novel transcripts overexpressed in hematopoietic stem cells," Cancer Res., Jul. 2004, 64(13):4434-4441.
Gerstein et al., "Wound healing and aging," Dermatol.Clin., Oct. 1993, 11(4):749-757.
Gilbert et al., "DNA methylation affects nuclear organization, histone modifications, and linker histone binding but not chromatin compaction," J. Cell Biol., May 2007, 177(3):401-411.
Godfrey et al., "NKT cells: what's in a name?," Mar. 2004, Nat. Rev. Immunol, 4(3):231-237.
Golovina and Vonderheide, "Regulatory T cells: overcoming suppression of T-cell immunity," Cancer J., Jul.-Aug. 2010, 16(4):342-347.
Gomes et al., "Targeting γδT lymphocytes for cancer immunotherapy: from novel mechanistic insight to clinical application," Cancer Res., Dec. 2010, 70(24):10024-10027.
Gore et al., "DNA methylation in hematopoietic development and disease," Exp. Hematol, Sep. 2016, 44(9):783-790.
Gosain et al., "Aging and wound healing," World J. Surg., Mar. 2004, 28(3):321-326.
Gould & Fulton, "Wound healing in older adults," R.I. Med. J., Feb. 2016, 99(2): 34-36.
Gould et al., "Chronic wound repair and healing in older adults: current status and future research," J. Am. Geriatr. Soc., Mar. 2015, 63(3):427-438.
Greten et al., "IKKbeta links inflammation and tumorigenesis in a mouse model of colitis-associated cancer," Cell, Aug. 2004, 118(3):285-296.
Guo and Dipietro, "Factors affecting wound healing," J. Dent. Res., Mar. 2010, 89(3): 219-229.
Guo et al., "Cancer stem cells," Pediatric Res., Apr. 2006, 59(4 Pt 2):59R-64R.
Guo et al., "Mapping cellular hierarchy by single-cell analysis of the cell surface repertoire," Cell Stem Cell, Oct. 2013, 13(4):492-505.
Haetscher et al., "STAT5-regulated microRNA-193b controls haematopoietic stem and progenitor cell expansion by modulating cytokine receptor signalling," Nat. Commun., Nov. 2015, 6:8928, 11 pages.
Hennekens and Andreotti, "Leading avoidable cause of premature deaths worldwide: case for obesity," Am. J. Med., Feb. 2013, 126(2):97-98.

Hirano et al., "Discovery of GSK2795039, a novel small molecule NADPH oxidase 2 inhibitor," Antioxid. Redox. Signal., Aug. 2015, 23(5):358-374.
Holmes and Zuniga-Pflucker, "The OP9-DL1 system: generation of T-lymphocytes from embryonic or hematopoietic stem cells in vitro," Cold Spring Harb. Protoc., Feb. 2009, 2009(2):pdb.prot5156.
Holtmeier et al., "γδ cells link innate and adaptive immune responses," Chem. Immunol. Allergy, 2015, 86:151-183.
Huang et al., "Rates of complications and mortality in older patients with diabetes mellitus," JAMA Intern. Med., Feb. 2014, 174(2):251-258.
Huber et al., "Regulation of monocyte differentiation by specific signaling modules and associated transcription factor networks," Cell. Mol. Life Sci., Jan. 2014, 71(1):63-92.
International Search Report and Written Opinion in International Application No. PCT/US 18/40642 dated Nov. 5, 2018, 16 pages.
International Search Report and Written Opinion in International Application No. PCT/US 16/14477, dated Apr. 22, 2016, 15 pages.
Ito et al., "Role of Tet proteins in 5mC to 5hmC conversion, ES-cell self-renewal, and inner cell mass specification," Nature, Aug. 2010, 466(7310):1129-1133.
Ito et al., "Tet proteins can convert 5-methylcytosine to 5-formylcytosine and 5-carboxylcytosine," Science, Sep. 2011, 333(6047):1300-1303.
Jablonski et al., "Novel markers to delineate murine M1 and M2 macrophages," PLoS One, Dec. 2015, 10(12):e0145342, 25 pages.
Jackson et al., "Severe global DNA hypomethylation blocks differentiation and induces histone hyperacetylation in embiyonic stem cells," Mol. Cell. Biol., Oct. 2004, 24(20):8862-8871.
Jin et al., "DNA methyltransferase 3B (DNMT3B) mutations in ICF syndrome lead to altered epigenetic modifications and aberrant expression of genes regulating development, neurogenesis and immune function," Hum. Mol. Genet., Mar. 2008, 17(5):690-709.
Jin et al., "Long non-coding RNA SPRY4-IT1 promotes proliferation and invasion by acting as a ceRNA of miR-101-3p in colorectal cancer cells," Tumour Biol., Jul. 2017, 39(7): 1-6.
Katsarou et al., "Type 1 diabetes mellitus," Nat. Rev. Dis. Primers, Mar. 2017, 3:17016, 17 pages.
Kawasaki and Taira, "Induction of DNA methylation and gene silencing by short interfering RNAs in human cells," Nature, Sep. 2004, 431(7005):211-217.
Kerkar et al., "Cellular constituents of immune escape within the tumor microenvironment," Cancer Res., Jul. 2012, 72(13): 3125-3130.
Khanna et al., "Macrophage dysfunction impairs resolution of inflammation in the wounds of diabetic mice," PLoS One, Mar. 2010, 5(3):e9539, 12 pages.
Kim et al., "Discrete Notch signaling requirements in the specification of hematopoietic stem cells," EMBO J., Oct. 2014, 33(20):2363-2373.
Klein et al., "Mutations in DNMT1 cause hereditary sensory neuropathy with dementia and hearing loss," Nat. Genet., Jun. 2011, 43(6):595-600.
Klingenberg et al., "Depletion of FOXP3+ regulatory T cells promotes hypercholesterolemia and atherosclerosis," J. Clin. Invest., Mar. 2013, 12(3)3:1323-1334.
Klinke, "A multiscale systems perspective on cancer, immunotherapy, and Interleukin-12," Mol. Cancer., Sep. 2010, 9:242, 18 pages.
Ko et al., "Impaired hydroxylation of 5-methylcytosine in myeloid cancers with mutant TET2," Nature, Dec. 2010, 468(7325):839-843.
Ko et al., "Ten-Eleven-Translocation 2 (TET2) negatively regulates homeostasis and differentiation of hematopoietic stem cells in mice," Proc. Natl. Acad. Sci. USA, Aug. 2011, 108(35):14566-14571.
Kobayashi et al., "A new indicator of favorable prognosis in locally advanced renal cell carcinomas: gamma delta T-cells in peripheral blood," Anticancer Res., Mar. 2011, 31(3):1027-1032.
Kobayashi et al., "Safety profile and anti-tumor effects of adoptive immunotherapy using gamma-delta T cells against advanced renal cell carcinoma: a pilot study," Cancer Immunol. Immunother., Apr. 2007, 56(4):469-476.

(56) References Cited

OTHER PUBLICATIONS

Koene et al., "Shared risk factors in cardiovascular disease and cancer," Circulation, Mar. 2016, 133(11):1104-1114.
Kondo et al., "Zoledronate facilitates large-scale ex vivo expansion of functional γδ T cells from cancer patients for use in adoptive immunotherapy," Cytotherapy, 2008, 10(8):842-856.
Krüger et al., "Immune based therapies in cancer," Histol Histopathol., Jun. 2007, 22(6):687-696.
Krzyszczyk et al., "The role of macrophages in acute and chronic wound healing and interventions to promote pro-wound healing phenotypes," Front. Physiol., May 2018, 9:419, 22 pages.
Kurita et al., "DNMT1 and DNMT3b silencing sensitizes human hepatoma cells to TRAIL-mediated apoptosis via up-regulation of TRAIL-R2/DR5 and caspase-8," Cancer Sci., Jun. 2010, 101(6):1431-1439.
Lantz et al., "An invariant T cell receptor a chain is used by a unique subset of major histocompatibility complex class I-specific CD4+ and CD4-8-T cells in mice and humans," J. Exp. Med., Sep. 1994, 180(3):1097-1106.
Laslo et al., "Multilineage transcriptional priming and determination of alternate hematopoietic cell fates," Cell, Aug. 2006, 126(4):755-766.
Lee and Margolin, "Cytokines in Cancer Immunotherapy," Cancers, Oct. 2011, 3(4):3856-3893.
Li et al., "Epigenetic inactivation of the CpG demethylase TET1 as a DNA methylation feedback loop in human cancers," Sci. Rep., May 2016, 6:26591, 13 pages.
Li et al., "Targeted mutation of the DNA methyltransferase gene results in embryonic lethality," Cell, Jun. 1992, 69(6):915-926.
Li et al., "Tumor microenvironment: the role of tumor stroma in cancer," J. Cell. Biochem., Jul. 2007, 101(4):805-815.
Liao et al., "Krüppel-like factor 4 regulates macrophage polarization," J. Clin. Invest., Jul. 2011, 121(7):2736-2749.
Liao et al., "Targeted disruption of DNMT1, DNMT3A and DNMT3B in human embryonic stem cells," Nat. Genet., May 2015, 47(5):469-478.
Liguori et al., "Oxidative stress, aging, and diseases," Clin. Interv. Aging, Apr. 2018, 13:757-772.
Liu et al., "Age-dependent impairment of HIF-1a expression in diabetic mice: correction with electroporation-facilitated gene therapy increases wound healing, angiogenesis, and circulating angiogenic cells," J. Cell. Physiol., Nov. 2008, 217(2):319-327.
Liu et al., "MicroRNA-101-3p suppresses cell proliferation, invasion and enhances chemotherapeutic sensitivity in salivary gland adenoid cystic carcinoma by targeting Pim-1," Am. J. Cancer Res., Oct. 2015, 5(10): 3015-3029.
Lu et al., "Polysaccharide krestin is a novel TLR2 agonist that mediates inhibition of tumor growth via stimulation of CD8 T Cells and NK Cells," Clin. Cancer. Res., Jan. 2011, 17(1):67-76.
Luo et al., "Long non-coding RNAs control hematopoietic stem cell function," Cell Stem, Apr. 2015, 16(4):426-438.
Luo, et al., "Targeting tumor-associated macrophages as a novel strategy against breast cancer," J. Clin. Invest., Aug. 2006, 116(8):2132-2141.
MacLeod et al., "Skin-resident T cells sense ultraviolet radiation-induced injury and contribute to DNA repair," J. Immunol., Jun. 2014, 192(12):5695-5702.
Makrantonaki et al., "Pathogenesis of wound healing disorders in the elderly," J. Dtsch Dermatol. Ges., Mar. 2017, 15(3):255-275.
Mantovani et al., "Macrophage polarization comes of age," Immunity, Oct. 2005, 23(4):344-346.
Martinez et al., "Alternative activation of macrophages: an immunologic functional perspective," Annu. Rev. Immunol., 2009, 27:451-483.
Maruyama et al., "Decreased macrophage number and activation lead to reduced lymphatic vessel formation and contribute to impaired diabetic wound healing," Am. J. Pathol., Apr. 2007, 170(4):1178-1191.
Matsuda et al., "Developmental program of mouse Valpha14i NKT cells," Curr. Opin. Immunol., Apr. 2005, 17(2):122-130.

McKercher et al., "Targeted disruption of the PU.1 gene results in multiple hematopoietic abnormalities," EMBO J., Oct. 1996, 15(20):5647-5658.
Melero et al., "IL-12 gene therapy for cancer: in synergy with other immunotherapies," Trends. Immunol., Mar. 2001, 22(3):113-115.
Mercer et al., "Multilineage priming of enhancer repertoires precedes commitment to the B and myeloid cell lineages in hematopoietic progenitors," Immunity, Sep. 2011, 35(3):413-425.
Mineharu et al., "Blockade of mTOR signaling via rapamycin combined with immunotherapy augments antiglioma cytotoxic and memory T-Cell Functions," Mol. Cancer Ther., Dec. 2014, 13(12): 3024-3036.
Moschella et al., "Combination strategies for enhancing the efficacy of immunotherapy in cancer patients," Ann. NY Acad. Sci., Apr. 2010, 1194:169-178.
Motohashi et al., "A phase I study of in vitro expanded natural killer T cells in patients with advanced and recurrent non-small cell lung cancer," Clin Cancer Res., Oct. 2006, 12(20 Pt 1):6079-6086.
Munn, "Blocking IDO activity to enhance anti-tumor immunity," Front Biosci (Elite Ed), Jan. 2012, 4: 734-745.
NCEP, "Third Report of the National Cholesterol Education Program (NCEP) Expert Panel on Detection, Evaluation, and Treatment of High Blood Cholesterol in Adults (Adult Treatment Panel III) final report," Circulation, 2002, 106(25): 3143-421.
Neri et al., "TET1 is a tumour suppressor that inhibits colon cancer growth by derepressing inhibitors of the WNT pathway," Oncogene, Aug. 2015, 34(32): 4168-4176.
Notarnicola et al., "Semm lipid profile in colorectal cancer patients with and without synchronous distant metastases," Oncology, 2005, 68(4-6):371-374.
Nunez-Cruz et al., "Differential requirement for the SAP-Fyn interaction during NK T cell development and function," J. Immunol., Aug. 2008, 181(4):2311-2320.
Oh et al., "Stem cell aging: mechanisms, regulators and therapeutic opportunities," Nat. Med., Aug. 2014, 20(8):870-880.
Okano et al., "Cloning and characterization of a family of novel mammalian DNA (cytosine-5) methyltransferases," Nat. Genet., Jul. 1998, 19(3): 219-220.
Okano et al., "DNA methyltransferases Dnmt3a and Dnmt3b are essential for de novo methylation and mammalian development," Cell, Oct. 1999, 99(3):247-257.
Omar et al., "Enhanced beta cell function and anti-inflammatory effect after chronic treatment with the dipeptidyl peptidase-4 inhibitor vildagliptin in an advanced-aged diet-induced obesity mouse model," Diabetologia, Aug. 2013, 56(8):1752-1760.
Orkin, "Priming the hematopoietic pump," Immunity, Nov. 2003, 19(5):633-634.
Outtz et al., "Notch1 deficiency results in decreased inflammation during wound healing and regulates vascular endothelial growth factor receptor-1 and inflammatory cytokine expression in macrophages," J. Immunol., Oct. 2010, 185(7):4363-4373.
Papakonstantinou et al., "Differential microRNA profiles and their functional implications in different immunogenetic subsets of chronic lymphocytic leukemia," Mol. Med., May 2013, 19: 115-123.
Pattabiraman and Weinberg, "Tackling the cancer stem cells—what challenges do they pose?," Nat. Rev. Drug Discov., Jul. 2014, 13(7):497-512.
PCT International Preliminary Report on Patentability in International Application No. PCT/US17/59367, dated May 16, 2019, 11 pages.
PCT International Preliminary Report on Patentability in International Application No. PCT/US2016/014477, dated Jul. 25, 2017.
Pearce et al., "Enhancing CD8 T-cell memory by modulating fatty acid metabolism," Nature, Jul. 2009, 460(7251):103-107.
Pervaiz et al., "Oxidative stress regulation of stem and progenitor cells," Antioxid. Redox. Signal., Nov. 2009, 11(11):2777-2789.
Piccoli et al., "Bone-marrow derived hematopoietic stem/progenitor cells express multiple isoforms of NADPH oxidase and produce constitutively reactive oxygen species," Biochem. Biophys. Res. Commun., Feb. 2007, 353(4):965-972.
Plowden et al., "Innate immunity in aging: impact on macrophage function," Aging Cell, Aug. 2004, 3(4):161-167.

(56) References Cited

OTHER PUBLICATIONS

Porcelli et al., "Analysis of T cell antigen receptor (TCR) expression by human peripheral blood CD4-8-α/b T cells demonstrates preferential use of several Vb genes and an invariant TCR α chain," J. Exp. Med., Jul. 1993, 178(1):1-16.
Portielje et al., "IL-12: a promising adjuvant for cancer vaccination," Cancer Immunol. Immunother., Mar. 2003, 52(3):133-144.
Pradeu and Cooper, "The danger theory: 20 years later," Front Immunol., 2012, 3:287, 10 pages.
Prattichizzo et al., ""Inflammaging" as a druggable target: a senescence-associated secretory phenotype-centered view of type 2 diabetes," OxidMed Cell. Longev., vol. 2016, Article ID 1810327, 10 pages.
Quail and Joyce, "Microenvironmental regulation of tumor progression and metastasis," Nat. Med., Nov. 2013, 19(11):1423-1437.
Rector et al., "Comprehensive hematopoietic stem cell isolation methods," Methods Mol. Biol., 2013, 976:1-15.
Reiber et al., "Causal pathways for incident lower-extremity ulcers in patients with diabetes from two settings," Diabetes Care, Jan. 1999, 22(1):157-162.
Robson et al., "Oxidative stress biomarkers in type 2 diabetes mellitus for assessment of cardiovascular disease risk," Diabetes Metab. Syndr., May 2018, 12(3):455-462.
Rogers et al., "A role for DNA hypomethylation and histone acetylation in maintaining allelespecific expression of mouse NKG2A in developing and mature NK cells," J. Immunol., Jul. 2006, 177(1):414-421.
Sag et al., "ATP-binding cassette transporter G1 intrinsically regulates invariant NKT cell development," J. Immunol., Dec. 2012, 189(11):5129-5138.
Sag et al., "The cholesterol transporter ABCG1 links cholesterol homeostasis and tumour immunity," Nat. Commun., Feb. 2015, 6:6354, 14 pages.
Satoh et al., "Unbalanced M1/M2 phenotype of peripheral blood monocytes in obese diabetic patients: effect of pioglitazone," Diabetes Care, Jan. 2010, 33(1):e7.
Schmitt et al., "Induction of T cell development and establishment of T cell competence from embryonic stem cells differentiated in vitro," Nat. Immunol., Apr. 2004, 5(4):410-417.
Schroeder et al., "Notch signaling induces multilineage myeloid differentiation and up-regulates PU.1 expression," J. Immunol., Jun. 2003, 170(11):5538-5548.
Scott et al., "Antibody therapy of cancer," Nat. Rev. Cancer, Mar. 2012, 12(4):278-287.
Sesti et al., "Insulin receptor variant forms and Type 2 diabetes mellitus," Pharmacogenomics, Feb. 2000, 1(1):49-61.
Sesti et al., "Molecular mechanism of insulin resistance in type 2 diabetes mellitus: role of the insulin receptor variant forms," Diabetes Metab. Res. Rev., Sep.-Oct. 2001, 17(5):363-373.
Sgonc et al., "Age-related aspects of cutaneous wound healing: a mini-review," Gerontology, 2013, 59(2):159-164.
Silva-Santos et al., "γδ T cells in cancer," Nat. Rev. Immunol., Nov. 2015, 15(11):883-889.
Smyth et al., "Tumor necrosis factor-related apoptosis-inducing ligand (TRAIL) contributes to interferon gamma-dependent natural killer cell protection from tumor metastasis," J. Exp. Med., Mar. 2001, 193(6):661-670.
Sosenko et al., "The prediction of type 1 diabetes by multiple autoantibody levels and their incorporation into an autoantibody risk score in relatives of type 1 diabetic patients," Diabetes Care, Sep. 2013, 36(9):2615-2620.
Spanholtz et al., "High log-scale expansion of functional human natural killer cells from umbilical cord blood CD34-positive cells for adoptive cancer immunotherapy," PLOS ONE, Feb. 2010, 5(2):e9221.
Strid et al., "Acute upregulation of an NKG2D ligand promotes rapid reorganization of a local immune compartment with pleiotropic effects on carcinogenesis," Nat. Immunol., Feb. 2008, 9(2):146-154.
Taniguchi et al., "The NKT cell system: bridging innate and acquired immunity," Nat. Immunol., Dec. 2003, 4(12):1164-1165.

Tarhini and Iqbal, "CTLA-4 blockade: therapeutic potential in cancer treatments," Onco. Targets Ther., Jun. 2010, 3:15-25.
Tavares et al., "Normal lymphocyte immunophenotype in an elderly population," Rev. Bras. Hematol. Hemoter., May-Jun. 2014, 36(3):180-183.
Tepper et al., "Decreased circulating progenitor cell number and failed mechanisms of stromal cell-derived factor-1 mediated bone marrow mobilization impair diabetic tissue repair," Diabetes, Aug. 2010, 59(8):1974-1983.
Themeli et al., "Generation of tumor-targeted human T lymphocytes from induced pluripotent stem cells for cancer therapy," Nat Biotechnol., Oct. 2013, 31(10):928-933.
Thermofisher Scientific, "hsa-miR-132-3p Product Details," Jan. 2, 2018; downloaded from the internet <https://https://www.thermofisher.com/order/genome-database/details/mirna/MC10166>, pp. 1-3.
Tie et al., "Hypercholesterolemia induces oxidant stress that accelerates the ageing of hematopoietic stem cells," J Am Heart Assoc., Jan. 2014, 3(1):e000241.
Todaro et al., "Efficient killing of human colon cancer stem cells by γδ T lymphocytes," J. Immunol., Jun. 2009, 182(11):7287-7296.
Topalian et al., "Safety, activity, and immune correlates of anti-PD-1 antibody in cancer," NEJM, Jul. 2012, 366(26):2443-2454.
Toura et al., "Cutting edge: inhibition of experimental tumor metastasis by dendritic cells pulsed with α-galactosylceramide," J. Immunol., Sep. 1999, 163(5):2387-2391.
TPA: Mus msuculus mRNA mmu-let-7d-3p; GenBank Accession LM379002.1. Mar. 3, 2015; downloaded from the internet <https://www.ncbi.nlm.nih.gov/nuccore/LM379002> on Sep. 25, 2018, p. 2.
Trowbridge et al., "DNA methyltransferase 1 is essential for and uniquely regulates hematopoietic stem and progenitor cells," Cell Stem Cell, Oct. 2009, 5(4):442-449.
Turley et al., "Immunological hallmarks of stromal cells in the tumor microenvironment," Nat. Rev. Immunol., Nov. 2015, 15(11):669-682.
Van Galen et al., "Reduced lymphoid lineage priming promotes human hematopoietic stem cell expansion," Cell Stem Cell, Jan. 2014, 14(1):94-106.
Vantourout and Hayday, "Six-of-the-best: unique contributions of γδ T cells to immunology," Nat. Rev. Immunol., Feb. 2013, 13(2):88-100.
Vella et al., "Tet proteins connect the O-linked N-acetylglucosamine transferase Ogt to chromatin in embryonic stem cells," Mol. Cell., Feb. 2013, 49(4):645-656.
Walsh et al., "Humanized mouse models of clinical disease," Annu. Rev. Pathol., Jan. 2017, 12:187-215.
Wang et al., "Total body irradiation causes residual bone marrow injury by induction of persistent oxidative stress in murine hematopoietic stem cells," Free Radic. Biol. Med., Jan. 2010, 48(2):348-356.
Wang et al., "The effects of DNA methyltransferase inhibitors and histone deacetylase inhibitors on digit regeneration in mice," Regen. Med., Mar. 2010, 5(2):201-220.
Watarai et al., "Murine induced pluripotent stem cells can be derived from and differentiate into natural killer T cells," J. Clin. Invest, Jul. 2010, 120(7):2610-2618.
Willenborg and Eming, "Macrophages—sensors and effectors coordinating skin damage and repair," J. Dtsch Dermatol. Ges., Mar. 2014, 12(3): 214-221.
Wilson et al., "STAT3 is a critical cell-intrinsic regulator of human unconventional T cell numbers and function," J Exp. Med., Jun. 2015, 212(6):855-864.
Winkelmann et al., "Mutations in DNMT1 cause autosomal dominant cerebellar ataxia, deafness and narcolepsy," Hum. Mol. Genet., May 2012, 21(10):2205-2210.
Wojtowicz-Praga, "Reversal of tumor-induced immunosuppression by TGF-beta inhibitors," Invest. New Drugs, Feb. 2003, 21(1):21-32.
Wong et al., "Abstract 54: MicroRNA Let-7d-3p in Heart Failure," Circulation Research, Jul. 2016, 119:A54.
Wood et al., "Pro-inflammatory chemokine CCL2 (MCP-1) promotes healing in diabetic wounds by restoring the macrophage response," PLoS One, Mar. 2014, 9(3):e91574, 8 pages.

(56) References Cited

OTHER PUBLICATIONS

Wu et al., "Mechanisms and functions of Tet protein-mediated 5-methylcytosine oxidation," Genes Dev., Dec. 2011, 25(23):2436-2452.

Wu et al., "Suppression of TET 1-dependent DNA demethylation is essential for KRAS-mediated transformation," Cell Reports, Dec. 2014, 9(5): 1827-1840.

Yan et al., "Diabetes impairs wound healing by Dnmt1-dependent dysregulation of hematopoietic stem cells differentiation towards macrophages," Nat. Commun., Jan. 2018, 9(1): 33, 13 pages.

Yan et al., "Type 2 diabetes restricts multipotency of mesenchymal stem cells and impairs their capacity to augment postischemic neovascularization in db/db Mice," J. Am. Heart Assoc., Dec. 2012, 1(6):e002238, 16 pages.

Yokota et al., "Complementary regulation of early B-lymphoid differentiation by genetic and epigenetic mechanisms," Int. J. Hematol., Oct. 2013, 98(4):382-389.

Yu et al., "Metabolic regulation by the mitochondrial phosphatase PTPMT1 is required for hematopoietic stem cell differentiation," Cell Stem Cell, Jan. 2013, 12(1):62-74.

Zarin et al., "Gamma delta T-cell differentiation and effector function programming, TCR signal strength, when and how much?," Cell Immunol., Jul. 2015, 296(1):70-75.

Zeisberger et al., "Clodronate-liposome-mediated depletion of tumour-associated macrophages: a new and highly effective antiangiogenic therapy approach," Br. J. Cancer., Aug. 2006, 95(3):272-281.

Zhao et al., "Inflammation in chronic wounds," Int. J. Mol. Sci., Dec. 2016, 17(12), pii:E2085.

Zhu et al., "Developing new chemical tools for DNA methyltransferase 1 (DNMT 1): a small-molecule activity-based probe and novel tetrazole-containing inhibitors," Bioorganic & Med Chemistry, Jun. 2015, 23(12):2917-2927.

Ziegler et al., "Seroconversion to multiple islet autoantibodies and risk of progression to diabetes in children," JAMA, Jul. 2013, 309(23):2473-2479.

Zitvogel et al., "Mechanism of action of conventional and targeted anticancer therapies: reinstating immunosurveillance," Immunity, Jul. 2013, 39(1):74-88.

Zykova et al., "Altered cytokine and nitric oxide secretion in vitro by macrophages from diabetic type II-like db/db mice," Diabetes, Sep. 2000, 49(9):1451-1458.

AlMatar et al., "Therapeutic potential of N-acetylcysteine for wound healing, acute bronchiolitis, and congenital heart defects," Current Drug Metabolism, Feb. 1, 2016, 17(2):156-67.

EP European Search Report in European Appln. No. 18903173.5, dated Oct. 18, 2021, 22 pages.

Park et al., "Effects of genistein on early-stage cutaneous wound healing," Biochemical and Biophysical Research Communications, Jul. 8, 2011, 410(3):514-9.

Xie et al., "Genistein inhibits DNA methylation and increases expression of tumor suppressor genes in human breast cancer cells," Genes, Chromosomes and Cancer, May 2014, 53(5):422-31.

EP Extended Search Report in European Appln. No. 18903173.5, dated Jan. 24, 2022, 19 pages.

CA Office Action in Canadian Appln. No. 2,973,878, dated Jan. 28, 2022, 5 pages.

Cui et al., "Upregulated lncRNA SNHGI contributes ti progression of nonsmall cell lung cancer through inhibition of m1R-101-3p and activation of Wnt/P-catenin signaling pathway," Oncotarget, Jan. 2017, 8: 17785-17794.

International Search Report and Written Opinion in International Application No. PCT/US17/59367, dated Feb. 2, 2019.

Jin et al., "Long non-coding RNA SPRY4-IT1 promotes proliferation and invasion by acting as a ceRNA of miR-101-3p in colorectal cancer cells," Tumor Biology, Jul. 7, 2017: 1-6.

Liu et al., "MicroRNA-101-3p suppresses cell proliferation, invasion and enhances chemotherapeutic sensitivity in salivary gland adenoid cystic carcinoma by targeting Pim-1,"American Journal of Cancer Research, Oct. 10, 2015: 3015-3029.

Papkonstantinou et al., "Differential microRNA Profiles and Their Functional Implications In Different Immunogenetic Subsets of Chronic Lymphocytic Leukemia," Molecualr Medicine, Apr. 19, 2013: 115-123.

\* cited by examiner

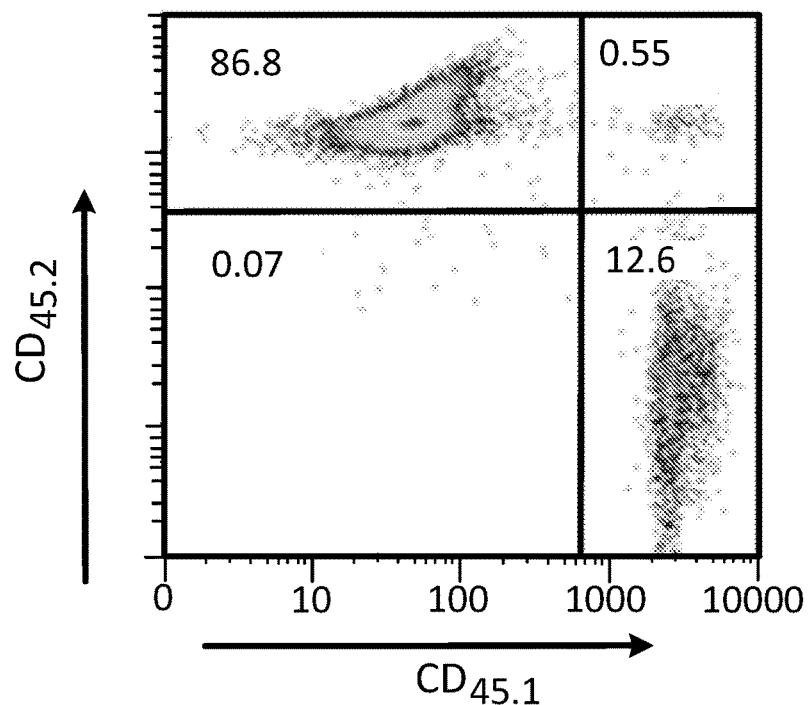
FIG. 1E
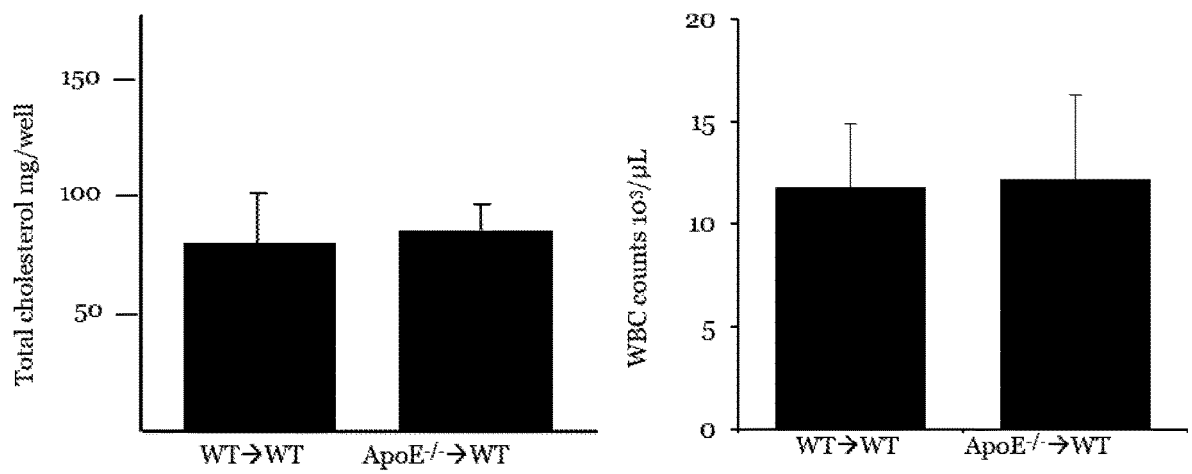
FIG. 1F
FIG. 1G

FIG. 3E                                FIG. 3F

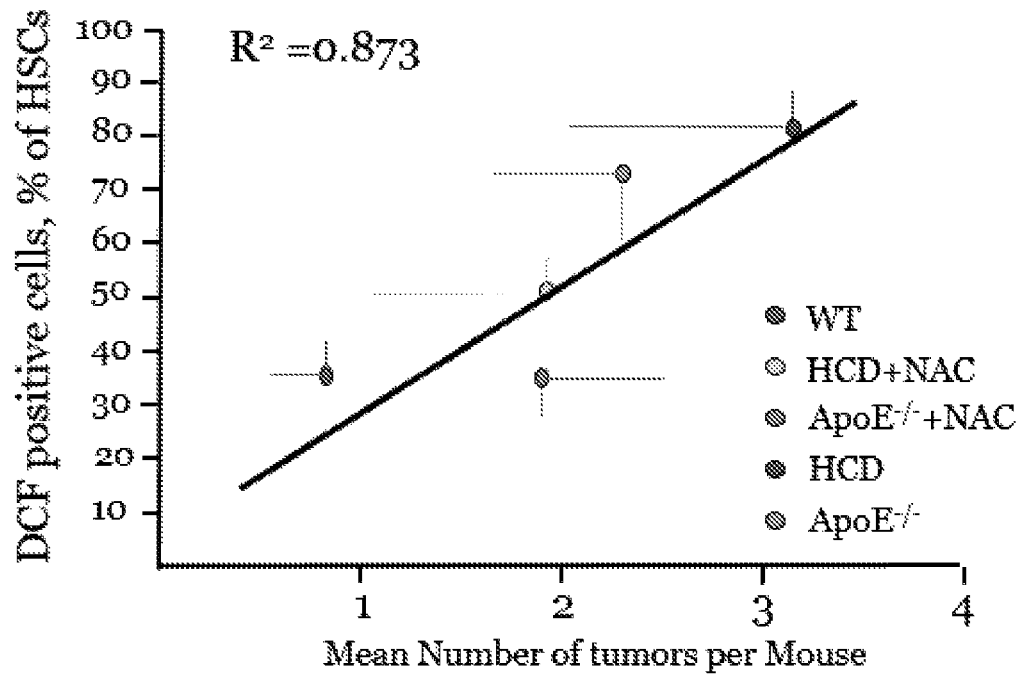
FIG. 4G
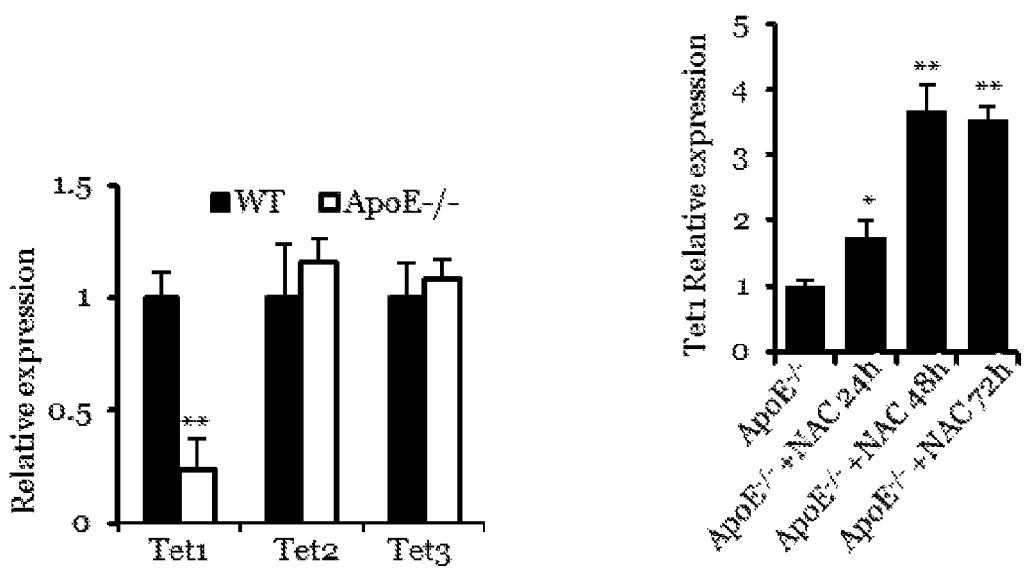
FIG. 5A
FIG. 5B

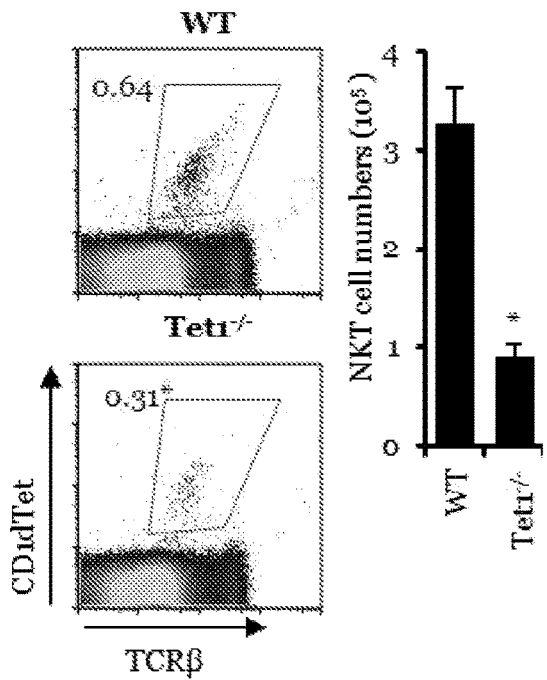
FIG. 5C
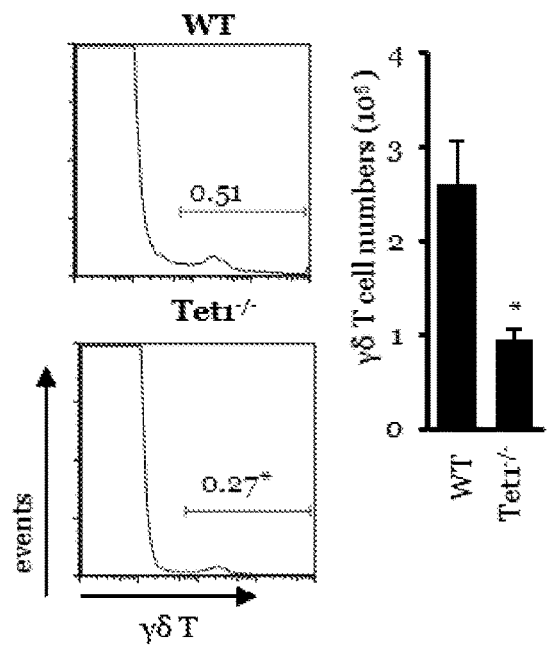
FIG. 5D
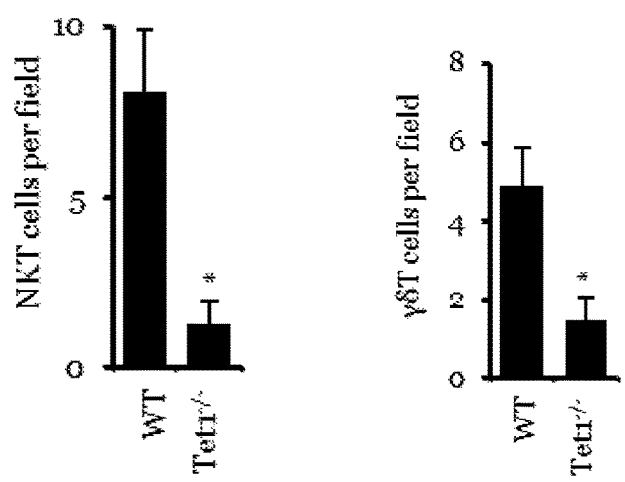
FIG. 5E
FIG. 5F
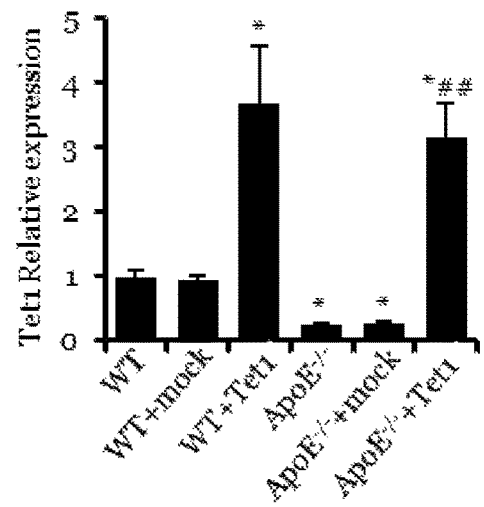
FIG. 5G

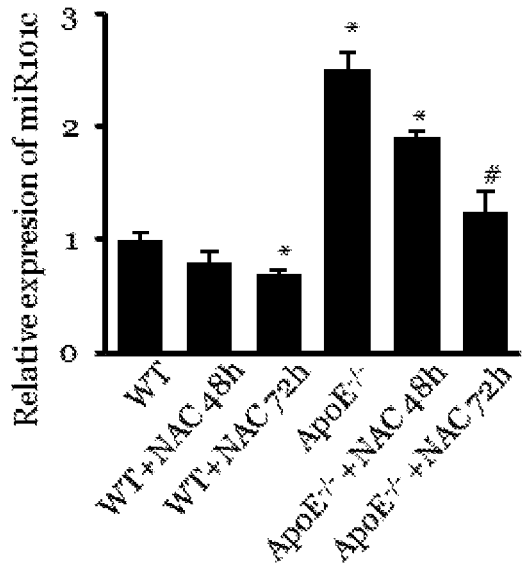
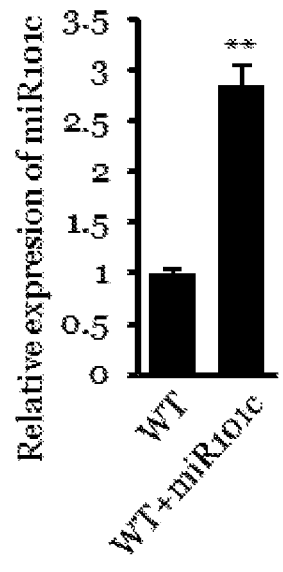
FIG. 8A                FIG. 8B
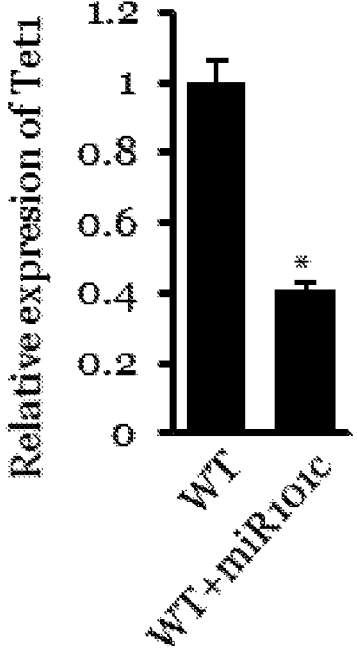
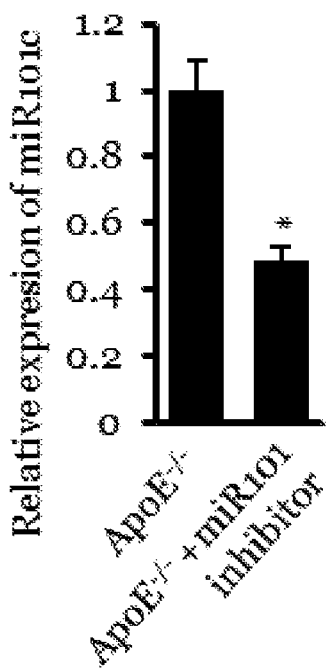
FIG. 8C                FIG. 8D

TARGETING MICRORNA-101-3P IN CANCER THERAPY

CLAIM OF PRIORITY

This application is a National Phase application under 35 U.S.C. § 371 of PCT International Application number PCT/US2017/059367, filed Oct. 31, 2017 which claims the benefit of U.S. Provisional Patent Application Ser. No. 62/415,269, filed on Oct. 31, 2016. The entire contents of the forgoing are hereby incorporated by reference.

FEDERALLY SPONSORED RESEARCH OR DEVELOPMENT

This invention was made with Government support under Grant No. HL075353 awarded by the National Institutes of Health. The Government has certain rights in the invention.

TECHNICAL FIELD

The invention relates, at least in part, to methods of treating cancer, e.g., colorectal cancer, using a miR-101-3p inhibitor.

BACKGROUND

Obesity will soon surpass smoking as the most preventable cause of cancer (Koene, et al. Circulation. 2016; 133:1104-14; and Hennekens, et al. Am J Med 2013; 126: 97-8). Obesity increases the incidence and mortality rates of several types of cancers, including colorectal, breast, prostate and lung cancer. Studies to determine which metabolic disorder or combination of disorders in obese people increases their cancer risk have been inconclusive (Font-Burgada, et al Cell Metab 2016; 23:48-62). Hypercholesterolemia, a common metabolic disorder in obese people, has been shown to increase cancer risk and substantial epidemiologic evidence links hypercholesterolemia to an increased risk of colorectal cancer (Notarnicola, et al. Oncology 2005; 68:371-374). It was originally proposed that hypercholesterolemia exerts a systemic, conditional influence that affects immunosurveillance against colorectal cancer. The mechanism by which hypercholesterolemia reduces the number and function of innate immune cells is unknown.

SUMMARY

The present invention is based, at least in part, on the discovery that hypercholesterolemia increases the incidence and pathological severity of colorectal cancer in two independent mouse models by inducing an oxidant-stress dependent increase in miR-101-3p that downregulates Tet1 in hematopoietic stem cells (HSCs), reducing the expression of genes critical to natural killer T cell (NKT) and γδT cell differentiation. These effects reduce the number and function of terminally differentiated NKT and γδT cells in the thymus, the colon submucosa and during early tumorigenesis. These results suggest a novel mechanism by which a metabolic disorder induces oxidant stress-dependent epigenetic mechanisms that reduce lineage priming of HSCs towards innate immune cells and thereby compromises immunosurveillance against cancer. Reducing levels of miR-101-3p abrogates this effect and restores anti-cancer immunocompetence.

Thus, provided herein are methods for treating cancer in a subject, comprising administering to the subject a therapeutically effective amount of a miR-101-3p inhibitory nucleic acid.

Also provided herein are methods for treating cancer in a subject, comprising administering to the subject a therapeutically effective amount of hematopoietic stem cells (HSCs) expressing a miR-101-3p inhibitory nucleic acid.

In some embodiments, the miR-101-3p inhibitory nucleic acid downregulates levels of Ten-eleven translocation methylcytosine dioxygenase 1 (Tet1).

In some embodiments, the miR-101-3p inhibitory nucleic acid is an oligonucleotide.

In some embodiments, the miR-101-3p inhibitory nucleic acid is an antisense molecule, a small interfering RNA, an antagomir, or a small hairpin RNA which are specific for a nucleic acid encoding SEQ ID NO:3.

In some embodiments, the miR-101-3p inhibitory nucleic acid is a nucleic acid comprising a sequence that is complementary to a contiguous sequence of at least 5 nucleotides present in miR-101-3p.

In some embodiments, the subject is human.

In some embodiments, the subject has, or is at risk of having hypercholesterolemia.

In some embodiments, the subject has a carcinoma, a sarcoma, a myeloma, a leukemia, or a lymphoma.

In some embodiments, the cancer is colorectal cancer, ovarian cancer, prostate cancer, lymphoid malignancies, myeloma, renal cell carcinoma, breast cancer or malignant glioma.

In some embodiments, the methods include administering to the subject one or more anti-cancer therapies. In some embodiments, the one or more anti-cancer therapies is selected from the group consisting of surgical resection with cold instruments or lasers, radiation therapy, phototherapy, biologic therapy, radiofrequency ablation (RFA), radioembolisation, chemotherapy, and immunotherapy.

Further provided herein are methods for reducing the risk of cancer in a subject who has, or is at risk of having hypercholesterolemia, comprising administering to the subject a therapeutically effective amount of a miR-101-3p inhibitory nucleic acid.

In some embodiments, the miR-101-3p inhibitory nucleic acid downregulates expression of Ten-eleven translocation methylcytosine dioxygenase 1 (Tet1).

In some embodiments, the miR-101-3p inhibitory nucleic acid is an oligonucleotide.

In some embodiments, the miR-101-3p inhibitory nucleic acid is an antisense molecule, a small interfering RNA, an antagomir, or a small hairpin RNA which are specific for a nucleic acid encoding SEQ ID NO:3.

In some embodiments, the miR-101-3p inhibitory nucleic acid is a nucleic acid comprising a sequence that is complementary to a contiguous sequence of at least 5 nucleotides present in miR-101-3p.

In some embodiments, the cancer is a carcinoma, a sarcoma, a myeloma, a leukemia, or a lymphoma.

In some embodiments, the cancer is colorectal cancer, ovarian cancer, prostate cancer, lymphoid malignancies, myeloma, renal cell carcinoma, breast cancer or malignant glioma.

In some embodiments, the method increases the number of NKT and γδT cells in blood or within in the cancer.

In some embodiments, the method restores cytotoxicity of NKT and γδT cells as compared to NKT and γδT cells of a subject who does not have hypercholesterolemia.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-G. Hypercholesterolemia increases average tumor number and histopathologic stage of colorectal cancer through a hematopoietic stem cell (HSC) autonomous manner. A, Average tumor number per mouse from WT, ApoE$^{-/-}$, and HCD mice. B, Histopathologic stages of the tumors from WT, ApoE$^{-/-}$, and HCD mice. n=12, *, p<0.05; **, p<0.01, vs. WT. C, Average tumor number from WT recipient mice reconstituted with HSCs from WT or ApoE$^{-/-}$ mice. D, Histopathologic stages of the tumors from WT recipient mice reconstituted with HSCs from WT or ApoE$^{-/-}$ mice. n=12, *, p<0.05; **, p<0.01, vs. WT. E, Proportion of thymocytes derived from donor HSCs (CD45.1–CD45.2+). F. Serum cholesterol levels of WT recipient mice reconstituted with HSCs from WT or ApoE$^{-/-}$ mice. G. White blood cell counts of WT recipient mice reconstituted with HSCs from WT or ApoE$^{-/-}$ mice.

FIGS. 3A-H. Hypercholesterolemia reduces the frequency and alters specific subsets and maturation of NKT and γδ T cells in the thymus. A, Frequency and number of NKT cells in thymus of WT and HCD mice. n=6, *, p<0.05, vs. WT. B, Frequency and number of γδ T cells in thymus of WT and HCD mice. n=6, *, p<0.05, vs. WT. C, DN1 (CD44$^+$CD25$^-$ DN), DN2 (CD44$^+$CD25$^+$ DN), and DN3 (CD44$^-$ CD25$^+$DN) populations in thymus of WT, ApoE$^{-/-}$ and HCD mice. n=8, *, p<0.05, vs. WT. D, DP (CD4$^+$CD8$^+$), DN (CD4$^-$CD8$^-$), CD4$^+$ and CD8$^+$ T cell populations in thymus of WT, ApoE$^{-/-}$ and HCD mice. n=8, *, p<0.05, vs. WT. E, Stage 0 (CD44-NK1.1$^-$), Stage 1 (CD44-NK1.1$^-$) and Stage 2 (CD44$^+$NK1.1$^+$) of NKT cells in thymus of WT and ApoE$^{-/-}$ mice. F, CD4$^+$ and CD4$^-$CD8$^-$ subsets of NKT cells in thymus of WT and ApoE$^{-/-}$ mice. n=5, *, p<0.05, vs. WT. G, Frequency of B cells, NK cells, CD3e$^+$, CD4$^+$ and CD8$^+$ cells in peripheral blood of WT, ApoE$^{-/-}$ and HCD mice. n=5, *, p<0.05, vs. WT. H, NK cells (CD45$^+$CD3e$^-$NKp46$^+$), CD11b$^-$ dendritic cells (CD11c$^+$CD11b$^-$CD103$^+$F4/80$^-$), CD11b$^+$ dendritic cells (CD11c$^+$CD11b$^+$CD103$^+$F4/80$^-$), CD11c macrophages (CD11c$^-$CD11b$^+$CD103$^-$F4/80$^+$) and CD11c$^+$ macrophages (CD11c$^+$CD11b$^+$CD103$^-$F4/80$^+$) in the colon of WT, ApoE$^{-/-}$ and HCD mice. n=5, *, p<0.05, vs. WT.

FIGS. 4A-G. Hypercholesterolemia-induced oxidant stress in HSCs positively correlates with AOM-induced colorectal cancer. A, Frequency and total number of NKT cells in thymus of ApoE$^{-/-}$ and N-Acetyl Cysteine (NAC) treated ApoE$^{-/-}$ mice. n=8, *, p<0.05, vs. ApoE$^{-/-}$. NAC was given in drinking water for 8 weeks (150 mg/kg/day). B, Frequency and total number of γδT cells in thymus of ApoE$^{-/-}$ and NAC treated ApoE$^{-/-}$ mice. n=8, *, p<0.05, vs. ApoE$^{-/-}$. C, Average tumor number and histopathologic stages of tumors isolated from ApoE$^{-/-}$ and NAC treated ApoE$^{-/-}$ mice. n=12, *, p<0.05, vs. ApoE$^{-/-}$. D, Average tumor number and histopathologic stages of tumors isolated from High Cholesterol Diet (HCD) and NAC treated HCD mice. n=12, *, p<0.05, vs. HCD. E, NKT cell infiltration in tumors from ApoE$^{-/-}$ and NAC treated ApoE$^{-/-}$ mice. n=6, *, p<0.05, vs. ApoE$^{-/-}$. F, γδT cell infiltration in tumors from ApoE$^{-/-}$ and NAC treated ApoE$^{-/-}$ mice. n=12, *, p<0.05, vs. ApoE$^{-/-}$. G, Regression analysis between oxidant stress in HSCs and tumor number.

FIGS. 5A-I. Hypercholesterolemia induced oxidant stress downregulates the expression of Tet1 in HSCs that impairs their differentiation towards NKT and γδT cells. A, Expression of Tet1, Tet2 and Tet3 in HSCs from WT and ApoE$^{-/-}$ mice. n=6, **, p<0.01, vs. WT. B, Oxidant stress dependent downregulation of Tet1 expression in HSCs from ApoE$^{-/-}$ mice. n=6, *p<0.05; **, p<0.01, vs. ApoE$^{-/-}$. C, Frequency and number of NKT cells in thymus of WT and Tet1$^{-/-}$ mice. n=5. *, p<0.05, vs. WT. D, Frequency and number of γδT cells in thymus of WT and Tet1$^{-/-}$ mice. n=5. *, p<0.05, vs. WT. E, Frequency of submucosal NKT cells in colon of WT and Tet1$^{-/-}$ mice. n=5, *, p<0.05, vs WT. F, Frequency of submucosal γδT cells in colon of WT and Tet1$^{-/-}$ mice. n=5, *, p<0.05, vs WT. G, Tet1 relative expression following its overexpression in WT and ApoE$^{-/-}$ HSCs. n=6, *, p<0.05; **, p<0.01, vs. WT; #, p<0.05; ##, p<0.01, vs. ApoE$^{-/-}$. H, Frequency of NKT cells in thymus of recipient mice transplanted with WT HSCs, ApoE$^{-/-}$ HSCs, Tet1 overexpressing WT HSCs or Tet1 overexpressing ApoE$^{-/-}$ HSCs. n=6, *, p<0.05; **, p<0.01, vs. WT; #, p<0.05, vs. ApoE$^{-/-}$. I, Frequency of γδT cells in thymus of recipient mice transplanted with WT HSCs, ApoE$^{-/-}$ HSCs, Tet1 overexpressing WT HSCs or Tet1 overexpressing ApoE$^{-/-}$ HSCs. n=6, *, p<0.05; **, p<0.01, vs. WT; #, p<0.05, vs. ApoE$^{-/-}$.

FIGS. 7A-G. Reconstitution of lethally irradiated WT mice with ApoE$^{-/-}$ HSCs that overexpress Tet1 restores immunosurveillance against colorectal cancer. A, Frequency of cells derived from Tet1 overexpressing HSCs. The transplantation of Tet1 overexpressing WT HSCs was supported with WT HSCs and the transplantation of Tet1 overexpressing ApoE$^{-/-}$ HSCs was supported with ApoE$^{-/-}$ HSCs, both at the ratio of 3:1. n=8, *, p<0.05; **, p<0.01, vs. WT+mock; ##, p<0.01, vs. ApoE$^{-/-}$+mock. B. Frequency and total number of NKT cells in thymus of the recipients after transplantation with WT HSCs, ApoE$^{-/-}$ HSCs, Tet1-overexpressing WT HSCs+WT HSCs, or Tet1-overexpressing ApoE$^{-/-}$ HSCs+ApoE$^{-/-}$ HSCs. n=8, *, p<0.05, vs. WT→WT; #, p<0.05, vs. ApoE$^{-/-}$→WT. C, Frequency and total number of γδT cells in thymus of the recipients. n=8, *, p<0.05, vs. WT→WT; #, p<0.05, vs. ApoE$^{-/-}$ 4WT. D, Frequency of NKT cells in colon submucosa of the recipients. n=8, , p<0.01, vs. WT→WT; #, p<0.05, vs. ApoE$^{-/-}$→WT. E, Frequency of γδT cells in colon submucosa of the recipients. n=8, , p<0.01, vs. WT→WT; #, p<0.05, vs. ApoE$^{-/-}$→WT. F, Average tumor number per mouse in the recipients. n=12, *, p<0.05, vs. WT→WT; #, p<0.05, vs. ApoE$^{-/-}$→WT. G, Histopathologic stages of tumors. n=12, *, p<0.05, **, p<0.01 vs. WT→WT; #, p<0.05, ##, p<0.01, vs. ApoE$^{-/-}$→WT.

FIGS. 8A-H. MiR101c mediates the downregulation of Tet1 in HSCs isolated from hypercholesterolemic mice. A, Oxidant stress dependent upregulation of miR101c in HSCs from ApoE$^{-/-}$ mice. n=6, *p<0.05; **, p<0.01, vs. WT. #p<0.05, vs. ApoE$^{-/-}$. B, Expression of miR101c mimics in WT HSCs. C, Expression of Tet1 in WT HSCs after transfection of miR101c mimics. n=6, *, p<0.05, vs WT control. D, Expression of miR101c in HSCs from ApoE$^{-/-}$ mice after transfection of miR101c inhibitor. E, Expression of Tet1 in HSCs from ApoE$^{-/-}$ mice after transfection of miR101c inhibitor. n=6, *, p<0.05, vs ApoE$^{-/-}$ control. F, Detection of direct binding between miR101c and Tet1 3' UTRs by luciferase reporter assay. C1=Construct1, C2=Construct2, M1=Mutant1, M2=Mutant2. G, Microarray profiling analysis in HSCs from WT and ApoE$^{-/-}$ mice. n=4. H, Oxidant stress dependent upregulation of miR-101c expression in HSCs from HCD fed mice. n=4, *, p<0.05, vs WT control; #, p<0.05, vs HCD control.

DETAILED DESCRIPTION

Figure 1A:
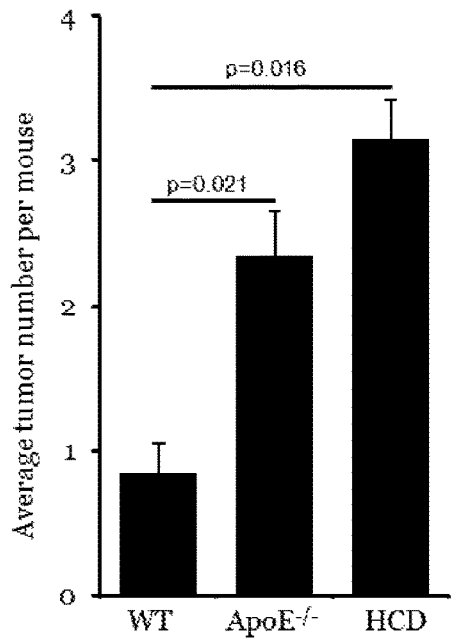

Hypercholesterolemia, a co-morbidity of obesity, has been shown to increase the risk of mortality, including an increased risk of death from thirteen different cancers (Orkin, S H. et al. 2003; Corpuz, T M. Et al. 2016). Without wishing to be bound by theory, the present results provide evidence that hypercholesterolemia increases the incidence and pathologic severity of colorectal cancer by inducing an oxidant stress dependent downregulation of Tet1 via miR101c, the mouse ortholog of human miR-101-3p, in HSCs that impairs their differentiation towards NKT and γδT cells. This reduction of Tet1 expression downregulates genes critical to the differentiation of HSCs towards NKT and γδT cells in large part by loss of activating histone H3K4me3 modifications and gain of repressive DNA methylation marks near the promoters of the key differentiation genes. These Tet1 induced effects on HSC differentiation reduce the number and function of terminally differentiated NKT and γδ T cells in the circulation, the submucosa of the gut, and finally within the early stages of tumor development. These findings reveal a novel mechanism by which innate immunity can be modulated by a metabolic abnormality at the level of HSC rather than at terminally differentiated immune cells.

Emerging evidence suggests that Tet1 functions as a critical tumor suppressor in multiple human cancers, including colorectal cancer (Cimmino et al. (2015)). The analysis of tumor methylomes showed that Tet1, as a methylated target, is frequently methylated and downregulated in cell lines and primary tumors of multiple carcinomas and lymphomas, including gastric and colorectal carcinomas (Chapman et al. (2015), Li et al. (2016), Neri et al. (2015)). The expression of the Tet1 catalytic domain is able to inhibit the CpG methylation of tumor suppressor gene promoters and reactivate their expression (Li et al. (2016)). The downregulation of Tet1 leads to the repression of the DKK gene and to the constitutive activation of the WNT pathway, resulting in the initiation of tumorigenesis in the colon. In addition, the re-expression of Tet1 in colon cancer cells inhibits their proliferation and the growth of tumor xenografts even at late stages (Neri et al. (2015)). These studies provide convincing evidence that Tet1 is a critical regulator in preventing the malformation and transformation of colon cells. We found that Tet1, by increasing the differentiation from HSCs towards NKT and γδ T cells, also functions as a critical regulator of innate immunity against colorectal cancer. Our findings provide new evidence for understanding how tumors escape immunosurveillance in the context of hypercholesterolemia.

Although genome wide chromatin immunoprecipitation (ChIP) studies established the central role of epigenetic modifications in HSC fate decision (van Galen et al. (2014), Guo et al. (2013), Mercer et al. (2011) and Orkin (2003)), little is known of how the epigenetic regulators of lineage priming are linked to a given lineage specification. Very recently, Cimmino and colleagues have shown that Tet1 activity in HSCs plays a critical role in preventing malignant transformation of HSCs into lymphomas, especially B cell lymphomas, in mice and humans (Cimmino, L. et al. 2015). Tet1 has also been shown to be a tumor suppressor in colon adenocarcinoma cells (Chapman, C G. et al. 2015). As shown herein, the inhibition of Tet1 in HSCs imposed repressive modification of the genes that controls their differentiation towards γδT cells and NKT cells. In contrast, overexpression of Tet1 reduced the methylation of these genes and thereby greatly increased the differentiation of HSCs towards NKT and γδT cells both in vivo and in vitro. These finding indicate that Tet1 is a master epigenetic regulator of HSC differentiation towards NKT and γδT cells.

As shown herein, the pathological consequences of hypercholesterolemia-induced HSC oxidant stress on immunosurveillance against colorectal cancer are funneled through a miR-101c downregulation of Tet1. It is the first evidence of miR-101c altering expression of specific protein in vivo. Frank and colleagues showed that miR101c, the mouse ortholog of human miR-101-3p affected the parasite clearance rates of bone marrow derived mononuclear cells but no specific protein(s) target was identified (Frank, B. et al. 2015). The relationship of the oxidant stress dependent increase in expression of miR101c and Tet1 is a compelling example of such a powerful regulatory network that controls the development of NKT and γδT cells.

In general, NKT and γδT cells are critical components of innate immunity against cancer and initiate the cascade of immune reactions to recognize and eliminate transformed cells in the early stage of immunosurveillance (Koene, R J. et al. 2016). NKT and γδT cells are unconventional T cell populations that are derived from HSCs (Dunn, G P. et al. 2002; Vantourout, P. et al. 2013). They are distributed in various tissues such as the colon submucosa and integrate into local immunosurveillance. Suppression of the T cell response to tumors has been observed frequently in cancer patients; specifically, NKT and γδT cells have been shown to be decreased or functionally hyporeactive in both cancer bearing mice and humans (Strid, J. et al. 2008; Bendelac, A. et al. 2007; Dhodapkar, M V. et al. 2003). In agreement with these studies, both NKT and γδT cells of hypercholesterolemic mice were decreased in the colon submucosa and during early stages of tumorigenesis. The overexpression of Tet1 significantly increased the differentiation of HSCs towards NKT and γδT cells both in vivo and in vitro. Despite reconstituting less than 10% of the T cells in the thymus of the transplanted recipient mice, γδT cell and NKT cell numbers in the thymus and most importantly in the submucosa of the colon were normal. The clinical implications of these findings are important.

Hematopoietic stem cells (HSCs) are multipotent, self-renewing cells that develop from mesodermal hemangioblast cells and give rise to all of the differentiated blood cells from the lymphoid and myeloid lineages. During development, HSCs colonize hematopoietic niches including the fetal liver, thymus, spleen and bone marrow, giving rise to sequential generations of blood cells. Adult HSC with multilineage differentiation potential are contained within a self-renewable pool in vertebrate bone marrow, liver, spleen and other sites. HSC differentiation is regulated by lineage specific epigenetic mechanisms and activation of genes for each successive generation of hematopoietic cells. See, e.g., Dieterlen-Lievre, Current Biology 8:R727-R730 (1998).

The Immunoscore (see US20150153349) is a more accurate predictor of tumor free survival in patients who have colorectal cancer than is the classical Dukes Classification or the TMN score (Themeli, M. et al. 2013). Although weak immune infiltrates have been postulated to be due to a defect in the host immune response, no etiology for this impaired host immune response has heretofore been identified (Galon, J. et al. 2012). Thus, the identification of a new level of regulation of innate immunity by oxidant stress-dependent epigenetic regulation of HSC differentiation may provide a context to understand why patients are found to have lower Immunoscores in their tumors. Creation of chimeric WT mice that received either ApoE$^{-/-}$ or WT HSCs that overexpressed Tet1 had a substantial effect on both the pathological stage and number of the tumors. In the lethally irradiated WT recipients of ApoE−/− HSCs that overexpressed Tet1, both the tumor number and their pathological severity were significantly reduced. Moreover, even the WT recipients of WT HSCs that overexpressed Tet1 showed a reduction in the pathologic stages of the tumors whereby no tumor progressed to the carcinoma stage.

Thus, a miR101-3p-Tet1 based HSC immunotherapy might not only be effective in patients found to have hypercholesterolemia but also in patients who do not have hypercholesterolemia.

The relationship between cardiovascular risk factors and cancer incidence is being actively investigated and sometimes referred to as CardioOncology (1). Cardiovascular disease and cancer share many similar risk factors. The relationship of hypercholesterolemia and colorectal cancer has been studied for decades. Some studies found a direct relationship where patients with hypercholesterolemia had an increase incidence of colorectal cancer. And other studies found an inverse relationship between serum hypercholesterolemia and colorectal cancer that raised questions about the relationship. However, it was learned subsequently that colonic adenocarcinoma cells can aggressively metabolize cholesterol and so studies that look for the relationship between these variables in patients with established cancers can lead to an erroneous conclusion. An additional issue is the findings that serum levels of 27-hydroxycholesterol (1), a metabolite of cholesterol, is associated with many cancers, especially breast cancer.

As used herein, the term "cancer" refers to a myriad of diseases generally characterized as cells having the capacity for autonomous growth, i.e., an abnormal state or condition characterized by rapidly or excessive proliferating cell growth. Hyperproliferative and neoplastic disease states may be categorized as pathologic, i.e., characterizing or constituting a disease state, or may be categorized as non-pathologic, i.e., a deviation from normal but not associated with a disease state. In general, a cancer will be associated with the presence of one or more tumors, i.e., abnormal cell masses. The term "tumor" is meant to include all types of cancerous growths or oncogenic processes, metastatic tissues or malignantly transformed cells, tissues, or organs, irrespective of histopathologic type or stage of invasiveness. A tumor is defined as a population of heterogeneous cells, containing both normal or "non-cancerous" cells and "cancerous" or "cancer" cells. In some embodiments, a tumor comprises stromal cells and/or inflammatory/immune cells, collectively forming a mass of tissue in a subject (Li et al. 2007) Tumor microenvironment: the role of tumor stroma in cancer. Journal of Cellular Biochemistry 101 (4): 805-15; Turley, S. et al. (2015) Immunological hallmarks of stromal cells in the tumor microenvironment. Nature Reviews Immunology 15: 669-682; Kerkar, S. et al. (2012) Cellular constituents of immune escape within the tumor microenvironment. Cancer Research 72(13): 3125-30; Quail, D F and Joyce J A (2013) Microenvironmental regulation of tumor progression and metastasis. Nature Medicine 19(11): 1423-37). The presence of stromal cells in a tumor may be identified using routine methods, including, but not limited to, fluorescent microscopy, fluorescence activated cell-sorting (FACS), immunohistochemistry, RT-PCR. "Pathologic hyperproliferative" cells occur in disease states characterized by malignant tumor growth. In general, the methods described herein can be practiced on subjects with solid tumors. As used herein, "immunosurveillance" is defined the processes by which cells of the immune system look for and recognize pre-cancerous and cancerous cells in the body, as well as foreign pathogens, such as viruses and bacteria (Dunn, G. et al. (2002) Cancer immunoediting: from immunosurveillance to tumor escape. Nature Immunology 3:991-998; Dunn, G. et al. (2004) The immunobiology of cancer immunosurveillance and immunoediting. Immunity 21(2): 137-148). Immunoediting is the process by which tumors escape from the response of the immune system, resulting in the emergence of immune-resistant variants.

In some embodiments, a tumor further comprises specialized cancer cells called "cancer stem cells". Cancer stem cells or "tumor-initiating cells" or "cancer-initiating cells" are thought to represent a subset of specialized cancer cells that are responsible for tumorigenesis and contribute to cancer resistance (see, e.g., Guo et al. (2006) Pediatric Research 59:59R-64R; Boesch et al. (2016) Biochimica et biophysica acta: S0304-419, Pattabiraman and Weinberg, (2014) Nature Reviews Drug Discovery 13(7):497-512). Cancer stem cells can self-renew and give rise to many cell types that constitute the bulk of the tumor. Cancer stem cells can be identified by various stem cell markers, such as CD44 and CD133.

Tumors include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, cancers evaluated by the methods described herein include those that are particularly immunogenic, e.g., colorectal cancer, neuroblastoma, melanoma, and renal cell cancer.

In some embodiments, cancers evaluated by the methods described herein include epithelial cancers, such as a lung cancer (e.g., non-small-cell lung cancer (NSCLC)), breast cancer, colorectal cancer, head and neck cancer, or ovarian cancer. Epithelial malignancies are cancers that affect epithelial tissues.

As used herein, the term "hypercholesterolemia" is a condition that is characterized by high levels of low-density lipoprotein (LDL) cholesterol in blood (≥160 mg/dL), as per the guidelines of the Third Report of the National Cholesterol Educational Program (NCEP) of Detection, Evaluation of Treatment of high cholesterol in adults (see, Circulation, 2002; 106(25): 3143-421). According to this report, a subject with LDL cholesterol levels <100 mg/dL, has little to no risk of developing coronary heart disease. LDL-cholesterol levels <100 mg/dL are considered optimal. "Near optimal" or "above optimal" LDL-cholesterol concentrations are between 100-129 mg/dL; "borderline high" LDL-cholesterol concentrations are between 130-159 mg/dL; "high" levels of LDL-cholesterol concentrations are between 160-189 mg/dL; and "very high" levels of LDL-cholesterol concentrations are ≥190 mg/dL (see page 3164, right column, third paragraph). As used herein, a subject has or is at risk of having hypercholesterolemia has LDL-cholesterol levels that are greater than "above optimal" LDL-cholesterol levels, e.g., >100-129 mg/dL. The common medical causes of hypercholesterolemia are genetic, diets rich in saturated fat, high fructose and high transfats, obesity, lack of physical activity, stress, and type 2 diabetes mellitus. Hypercholesterolemia is implicated as a high risk factor of cardiovascular disease, including atherosclerosis, arteriosclerosis, and coronary artery disease, where excess cholesterol in the bloodstream is deposited in the walls of blood vessels and arteries, in particular coronary arteries. In some embodiments, hypercholesterolemia is familial hypercholesterolemia, characterized by low levels of low-density lipoproteins (LDL) receptors.

miR-101-3p

As described herein, mir101-3p is a microRNA that recognizes ten-eleven translation methylcytosine dioxygenase 1 (Tet1). miR101c, the mouse ortholog of human miR-101-3p, is upregulated in HSCs of hypercholesterolemic mice. This is the first demonstration of an in vivo target of miR101c.

Inhibitory nucleic acids useful in the present methods and compositions include those that are designed to target miR101-3p. SEQ ID NO:1 is an exemplary mature murine sequence of miR-101c: 5'-ACAGUACU-GUGAUAACUGA-3' (SEQ ID NO: 1) (miRBase accession number: M10016974; NCBI Gene: 100628572); Fehniger, et al. (2010) Genome Research 20(11): 1590-604). The human counterpart of murine miR101c is miR-101-3p. SEQ ID NO:2 is an exemplary mature human sequence of miR-101-3p: 5'-UACAGUACUGUGAUAACUGAA-3' (SEQ ID NO:2) (miRBase accession number: MIMAT0000099). The seed sequence of hsa-miR-101-3p is 5'-ACAGUACU-3' (SEQ ID NO:3) (see FIG. 1, Megiormi, et al. PLoS One 2011; 6(10): e26601).

Methods of Treatment

The present methods include the use of miR-101-3p inhibitors, for treating a cancer, e.g., a tumor, in a subject who is in need of, or who has been determined to be in need of, such treatment. In some embodiments, the subject has or is at risk of having hypercholesterolemia. In some embodiments, the subject had normal serum cholesterol levels. In some embodiments, the neoplasm is a tumor, e.g., a tumor that is sensitive to innate immunity against cancer or immunosurveillance, e.g., carcinoma, sarcoma, myeloma, leukemia, or lymphoma. In some embodiments, the neoplasm is colorectal cancer, ovarian cancer, prostate cancer, lymphoid malignancies, myeloma, renal cell carcinoma, breast cancer or malignant glioma.

The term "subject" refers to any mammal. In some embodiments, the subject or "subject suitable for treatment" may be a canine (e.g. a dog), feline (e.g. a cat), equine (e.g. a horse), ovine, bovine, porcine. caprine, primate, e.g., a simian (e.g. a monkey (e.g. marmoset, baboon) or an ape (e.g. a gorilla, chimpanzee, orangutan, or gibbon)) or a human; or rodent (e.g., a mouse, guinea pig, a hamster, or a rat). In some embodiments, the subject or "subject suitable for treatment" may be a non-human mammal, especially mammals that are conventionally used as models for demonstrating therapeutic efficacy in humans (e.g., murine, lapine, porcine, canine, or primate animals) may be employed.

These methods can be used to treat a subject, e.g., a subject with cancer, by administering to the subject a composition (e.g., as described herein) comprising an oligo that binds to a miR-101-3p. Examples of oligos and target sequences are provided herein.

As used herein, treating includes "prophylactic treatment" which means reducing the incidence of or preventing (or reducing risk of) a sign or symptom of a disease in a patient at risk for the disease, and "therapeutic treatment", which means reducing signs or symptoms of a disease, reducing progression of a disease, reducing severity of a disease, re-occurrence in a patient diagnosed with the disease.

As used in this context, to "treat" means to ameliorate at least one clinical parameter of the tumor. In some embodiments, the parameter is tumor size, pathological stage, tumor growth rate, recurrence, or metastasis. In some embodiments, treatment may include inhibiting tumor growth, including complete cancer remission, and/or inhibiting cancer metastasis. Indices for measuring an inhibition of tumor growth include, but are not limited to: a decrease in cancer cell survival, a delayed tumor growth, a decrease in tumor volume or morphology (as determined for example by imaging methods, such as computed tomographic (CT) scan and sonography), a decrease in the levels of tumor-specific antigens, a destruction of tumor vasculature. In some embodiments, inhibition of tumor growth comprises an increase in the number and function, including cytotoxicity of NKT and/or γδT cells. Restoring immunosurveillance in a subject may improve the capacity of the subject to resist cancer growth, in particular growth of a cancer already present in the subject and/or decrease the propensity for cancer growth in the subject. In some embodiments, the increase in HSC differentiation towards NKT and/or γδT cells is effective to reduce tumor progression and the pathological severity of the tumor. The presence of NKT and/or γδT cells causes tumor growth to be impeded, as a result of immunological depletion of the tumor.

Anti-Cancer Therapies

In some embodiments, the methods include administering one or more anti-cancer therapies to a subject. The terms "combination therapy" or "combined treatment" or "in combination" as used herein denotes any form of concurrent or parallel treatment with at least two distinct therapeutic agents, e.g., administration of miR-101-3p inhibitors and one or more anti-cancer therapies. In some embodiments, miR-101-3p inhibitors and one or more anti-cancer therapies are administered simultaneously, separately, or sequentially. In some embodiments, the one or more anti-cancer therapies are chemotherapeutic agents, apoptosis-inducing agents, anti-angiogenic agents, cell growth-arrest agents, differentiation inducing agents, or biologic agents, e.g., monoclonal antibodies, kinase inhibitors, inhibitors of growth factors and their receptors. In some embodiments, the one or more anti-cancer therapies is a monoclonal antibody. Examples of monoclonal antibodies include but are not limited to: trastuzumab (Herceptin), bevacizumab (Avastin), Rituximab (Mabthera), antibodies capable of binding cancer stem cell markers, such as CD133, CD24, CD44, antibodies capable of binding to cadherin-17 (Scott et al. (2012) Nature Reviews Cancer 12: 278-287).

Anti-cancer therapies include those known in the art, e.g., surgical resection with cold instruments or lasers, radiotherapy, phototherapy, biologic therapy, radiofrequency ablation (RFA), radioembolisation (e.g., with 90Y spheres), cell therapy, chemotherapy, and immunotherapy. The vast majority of chemotherapeutics can be divided into antimetabolites (e.g., fluorouracil), alkylating agents (e.g., cyclophosphamide), antibiotics (e.g., daunorubicin), plant alkaloids (e.g., paclitaxel), and their synthetic derivatives hormonal agents, topoisomerase inhibitors (e.g., topotecan). Non-limiting examples of chemotherapeutic agents include: amsacrine, azacitidine, axathioprine, bevacizumab (or an antigen-binding fragment thereof), bleomycin, busulfan, carboplatin, capecitabine, chlorambucil, cisplatin, cyclophosphamide, cytarabine, dacarbazine, daunorubicin, docetaxel, doxifluridine, doxorubicin, epirubicin, erlotinib hydrochlorides, etoposide, fiudarabine, floxuridine, fludarabine, fluorouracil, gemcitabine, hydroxyurea, idarubicin, ifosfamide, irinotecan, lomustine, mechlorethamine, melphalan, mercaptopurine, methotrxate, mitomycin, mitoxantrone, oxaliplatin, paclitaxel, pemetrexed, procarbazine, all-trans retinoic acid, streptozocin, tafluposide, temozolomide, teniposide, tioguanine, topotecan, uramustine, valrubicin, vinblastine, vincristine, vindesine, vinorelbine, and combinations thereof. Each possibility represents a separate embodiment. Additional examples of anti-cancer treatments are known in the art; see, e.g. the guidelines for therapy from the American Society of Clinical Oncology (ASCO), European Society for Medical Oncology (ESMO), or National Comprehensive Cancer Network (NCCN).

Immunotherapies

In some embodiments, the methods include administering an immunotherapy to a subject. Immunotherapies include those therapies that target tumor-induced immune suppression; see, e.g., Stewart and Smyth, Cancer Metastasis Rev. 2011 March; 30(1):125-40. Immunotherapies useful in the methods described herein include those therapies that specifically increase lineage specification of hematopoietic cells (HSCs) towards NKT and γδT cells, e.g., that include the administration of miR-101-3p inhibitors as described herein; therapies that non-specifically restore immunosurveillance, e.g., that may not specifically target miR-101-3p but still result in altered localization, or proliferation of NKT and γδT cells (referred to generically herein as "non-specific immunosurveillance restoring immunotherapy"); and therapies that do not deplete NKT and γδT cells (referred to herein as "non-NKT and and γδT cells depleting immunotherapy"). In some embodiments, the methods include co-administering an immunotherapy, e.g., a non-specific immunosurveillance restoring immunotherapy or a non-NKT and γδT cells depleting immunotherapy to the subject concurrently with or subsequent to the administration of miR-101-3p inhibitors.

Examples of immunotherapies include, but are not limited to, adoptive T cell therapies or cancer vaccine preparations designed to induce T lymphocytes to recognize cancer cells, as well as checkpoint inhibitors such as anti-CD137 (BMS-663513), anti-PD1 (e.g., Nivolumab, pembrolizumab/MK-3475, Pidilizumab (CT-011)), anti-PDL1 (e.g., BMS-936559, MPDL3280A), or anti-CTLA-4 (e.g., ipilumimab; see, e.g., Kruger et al., Histol Histopathol. 2007 June; 22(6):687-96; Eggermont et al., Semin Oncol. 2010 October; 37(5):455-9; Klinke D J., Mol Cancer. 2010 Sep. 15; 9:242; Alexandrescu et al., J Immunother. 2010 July-August; 33(6):570-90; Moschella et al., Ann N Y Acad Sci. 2010 April; 1194:169-78; Ganesan and Bakhshi, Natl Med J India. 2010 January-February; 23(1):21-7; Golovina and Vonderheide, Cancer J. 2010 July-August; 16(4):342-7.

In some embodiments, these immunotherapies may primarily target immunoregulatory cell types such as regulatory T cells (Tregs) or M2 polarized macrophages, e.g., by reducing number, altering function, or preventing tumor localization of the immunoregulatory cell types. For example, Treg-targeted therapy includes anti-GITR monoclonal antibody (TRX518), cyclophosphamide (e.g., metronomic doses), arsenic trioxide, paclitaxel, sunitinib, oxaliplatin, PLX4720, anthracycline-based chemotherapy, Daclizumab (anti-CD25); Immunotoxin eg. Ontak (denileukin diftitox); lymphoablation (e.g., chemical or radiation lymphoablation) and agents that selectively target the VEGF-VEGFR signaling axis, such as VEGF blocking antibodies (e.g., bevacizumab), or inhibitors of VEGFR tyrosine kinase activity (e.g., lenvatinib) or ATP hydrolysis (e.g., using ectonucleotidase inhibitors, e.g., ARL67156 (6-N,N-Diethyl-D-β,γ-dibromomethyleneATP trisodium salt), 8-(4-chlorophenylthio) cAMP (pCPT-cAMP) and a related cyclic nucleotide analog (8-[4-chlorophenylthio] cGMP; pCPT-cGMP) and those described in WO 2007135195, as well as mAbs against CD73 or CD39). Docetaxel also has effects on M2 macrophages. See, e.g., Zitvogel et al., Immunity 39:74-88 (2013).

In another example, M2 macrophage targeted therapy includes clodronate-liposomes (Zeisberger, et al., Br J Cancer. 95:272-281 (2006)), DNA based vaccines (Luo, et al., J Clin Invest. 116(8): 2132-2141 (2006)), and M2 macrophage targeted pro-apoptotic peptides (Cieslewicz, et al., PNAS. 110(40): 15919-15924 (2013)). Some useful immunotherapies target the metabolic processes of immunity, and include adenosine receptor antagonists and small molecule inhibitors, e.g., istradefylline (KW-6002) and SCH-58261; indoleamine 2,3-dioxygenase (IDO) inhibitors, e.g., Small molecule inhibitors (e.g., 1-methyl-tryptophan (1MT), 1-methyl-d-tryptophan (D1MT), and Toho-1) or IDO-specific siRNAs, or natural products (e.g., Brassinin or exiguamine) (see, e.g., Munn, Front Biosci (Elite Ed). 2012 Jan. 1; 4: 734-45) or monoclonal antibodies that neutralize the metabolites of IDO, e.g., mAbs against N-formyl-kynurenine.

In some embodiments, the immunotherapies may antagonize the action of cytokines and chemokines such as IL-10, TGF-beta, IL-6, CCL2 and others that are associated with immunosuppression in cancer. For example, TGF-beta neutralizing therapies include anti-TGF-beta antibodies (e.g. fresolimumab, Infliximab, Lerdelimumab, GC-1008), antisense oligodeoxynucleotides (e.g., Trabedersen), and small molecule inhibitors of TGF-beta (e.g. LY2157299), (Wojtowicz-Praga, Invest New Drugs. 21(1): 21-32 (2003)). Another example of therapies that antagonize immunosuppression cytokines can include anti-IL-6 antibodies (e.g. siltuximab) (Guo, et al., Cancer Treat Rev. 38(7):904-910 (2012). mAbs against IL-10 or its receptor can also be used, e.g., humanized versions of those described in Llorente et al., Arthritis & Rheumatism, 43(8): 1790-1800, 2000 (anti-IL-10 mAb), or Newton et al., Clin Exp Immunol. 2014 July; 177(1):261-8 (Anti-interleukin-10R1 monoclonal antibody). mAbs against CCL2 or its receptors can also be used. In some embodiments, the cytokine immunotherapy is combined with a commonly used chemotherapeutic agent (e.g., gemcitabine, docetaxel, cisplatin, tamoxifen) as described in U.S. Pat. No. 8,476,246.

In some embodiments, immunotherapies can include agents that are believed to elicit "danger" signals, e.g., "PAMPs" (pathogen-associated molecular patterns) or "DAMPs" (damage-associated molecular patterns) that stimulate an immune response against the cancer. See, e.g., Pradeu and Cooper, Front Immunol. 2012, 3:287; Escamilla-Tilch et al., Immunol Cell Biol. 2013 November-December; 91(10):601-10. In some embodiments, immunotherapies can agonize toll-like receptors (TLRs) to stimulate an immune response. For example, TLR agonists include vaccine adjuvants (e.g., 3M-052) and small molecules (e.g., Imiquimod, muramyl dipeptide, CpG, and mifamurtide (muramyl tripeptide)) as well as polysaccharide krestin and endotoxin. See, Galluzi et al., Oncoimmunol. 1(5): 699-716 (2012), Lu et al., Clin Cancer Res. Jan. 1, 2011; 17(1): 67-76, U.S. Pat. Nos. 8,795,678 and 8,790,655. In some embodiments, immunotherapies can involve administration of cytokines that elicit an anti-cancer immune response, see Lee & Margolin, Cancers. 3: 3856-3893 (2011). For example, the cytokine IL-12 can be administered (Portielje, et al., Cancer Immunol Immunother. 52: 133-144 (2003)) or as gene therapy (Melero, et al., Trends Immunol. 22(3): 113-115 (2001)). In another example, interferons (IFNs), e.g., IFN-gamma, can be administered as adjuvant therapy (Dunn et al., Nat Rev Immunol. 6: 836-848 (2006)).

In some embodiments, immunotherapies can antagonize cell surface receptors to enhance the anti-cancer immune response. For example, antagonistic monoclonal antibodies that boost the anti-cancer immune response can include antibodies that target CTLA-4 (ipilimumab, see Tarhini and Iqbal, Onco Targets Ther. 3:15-25 (2010) and U.S. Pat. No. 7,741,345 or Tremelimumab) or antibodies that target PD-1 (nivolumab, see Topalian, et al., NEJM. 366(26): 2443-2454 (2012) and WO2013/173223A1, pembrolizumab/MK-3475, Pidilizumab (CT-011)).

Some immunotherapies enhance T cell recruitment to the tumor site (such as Endothelin receptor-A/B (ETRA/B) blockade, e.g., with macitentan or the combination of the ETRA and ETRB antagonists BQ123 and BQ788, see Coffman et al., Cancer Biol Ther. 2013 February; 14(2):184-92), or enhance CD8 T-cell memory cell formation (e.g., using rapamycin and metformin, see, e.g., Pearce et al., Nature. 2009 Jul. 2; 460(7251):103-7; Mineharu et al., Mol Cancer Ther. 2014 Sep. 25. pii: molcanther.0400.2014; and Berezhnoy et al., Oncoimmunology. 2014 May 14; 3: e28811). Immunotherapies can also include administering one or more of: adoptive cell transfer (ACT) involving transfer of ex vivo expanded autologous or allogeneic tumor-reactive lymphocytes, e.g., dendritic cells or peptides with adjuvant; cancer vaccines such as DNA-based vaccines, cytokines (e.g., IL-2), cyclophosphamide, anti-interleukin-2R immunotoxins, Prostaglandin E2 Inhibitors (e.g., using SC-50) and/or checkpoint inhibitors including antibodies such as anti-CD137, anti-PD1, anti-PDL1, or anti-CTLA-4 antibody.

In some embodiments, the methods include administering a composition comprising tumor-pulsed dendritic cells, e.g., as described in WO2009/114547 and references cited therein. See also Shiao et al., Genes & Dev. 2011. 25: 2559-2572. In some embodiments, the methods described herein include administering a composition, e.g., a sterile composition, comprising an inhibitory nucleic acid that is complementary to miR-101-3p as described herein. Inhibitory nucleic acids for use in practicing the methods described herein are described below.

Inhibitory nucleic acids have been employed as therapeutic moieties in the treatment of disease states in animals, including humans. Inhibitory nucleic acids can be useful therapeutic modalities that can be configured to be useful in treatment regimens for the treatment of cells, tissues and animals, especially humans.

For therapeutics, an animal, preferably a human, having a cancer suspected of having a cancer, or at increased risk of developing a cancer (e.g., by virtue of family history, genetic testing, or presence of other identified risk factor), is treated by administering an inhibitory nucleic acid in accordance with this disclosure. For example, in one non-limiting embodiment, the methods comprise the step of administering to the animal in need of treatment a therapeutically effective amount of an inhibitory nucleic acid as described herein.

Inhibitory Nucleic Acids

The methods described herein can include the administration of inhibitory nucleic acids that hybridize specifically to miR-101-3p to treat a cancer, e.g., colorectal cancer, ovarian cancer, prostate cancer, lymphoid malignancies, myeloma, renal cell carcinoma, breast cancer or malignant glioma.

A nucleic acid that "specifically" binds primarily to the target, i.e., to miR-101-3p but not to other non-target RNAs. The specificity of the nucleic acid interaction thus refers to its function (e.g., inhibiting miR-101-3p) rather than its hybridization capacity. Oligos may exhibit nonspecific binding to other sites in the genome or other mRNAs, without interfering with binding of other regulatory proteins and without causing degradation of the non-specifically-bound RNA. Thus this nonspecific binding does not significantly affect function of other non-target RNAs and results in no significant adverse effects. Inhibitory agents useful in the methods of treatment described herein include inhibitory nucleic acid molecules that decrease the expression or activity of any of the miR-101-3p microRNAs (e.g., mature microRNA 101-3p or precursor microRNA 101-3p)

Inhibitory nucleic acids useful in the present methods and compositions include antisense oligonucleotides, ribozymes, siRNA compounds, single- or double-stranded RNA interference (RNAi) compounds, such as siRNA compounds, modified bases/locked nucleic acids (LNAs), antagomirs, and other oligomeric compounds, or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010/040112.

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29, or 30 nucleotides in length, or any range there within.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA: DNA or RNA: RNA hybrids. Chimeric inhibitory nucleic acids of the invention may be formed as composite structures of two or more oligonucleotides, modified oligonucleotides, oligonucleosides, and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2-amino, and 2' O-methyl modifications on the ribose of pyrimidines, abasic residues, or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligodeoxynucleotide—the modified oligos survive intact for a longer time than unmodified oligonucleotides. Specific examples of modified oligonucleotides include those comprising modified backbones, for example, phosphorothioates, phosphotriesters, methyl phosphonates, short-chain alkyl or cycloalkyl intersugar linkages, or short-chain heteroatomic or heterocyclic intersugar linkages. Most preferred are oligonucleotides with phosphorothioate backbones and those with heteroatom backbones, particularly $CH_2$—NHO—$CH_2$, CH~N($CH_3$)~O~CH2 (known as a methylene(methylimino) or MMI backbone], $CH_2$—O—N ($CH_3$)—$CH_2$, $CH_2$—N($CH_3$)—N($CH_3$)—$CH_2$ and O—N ($CH_3$)— $CH_2$—$CH_2$ backbones, wherein the native phosphodiester backbone is represented as O—P—O—CH); amide backbones (see De Mesmaeker et al., *Ace. Chem. Res.* 28:366-374, 1995); morpholino backbone structures (see U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 254: 1497, 1991). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050 (each of which is incorporated by reference).

Morpholino-based oligomeric compounds are described in Braasch et al., *Biochemistry* 41(14):4503-4510, 2002; Genesis, volume 30, issue 3, 2001; Heasman, J., *Dev. Biol.*, 243:209-214, 2002; Nasevicius et al., *Nat. Genet.* 26: 216-220, 2000; Lacerra et al., *Proc. Natl. Acad. Sci. U.S.A.* 97:9591-9596, 2000; and U.S. Pat. No. 5,034,506. Cyclohexenyl nucleic acid oligonucleotide mimetics are described in Wang et al., *J. Am. Chem. Soc.* 122, 8595-8602, 2000.

Modified oligonucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439 (each of which is herein incorporated by reference).

One or more substituted sugar moieties can also be included, e.g., one of the following at the 2' position: OH, SH, $SCH_3$, F, OCN, $OCH_3$, $OCH_3O(CH_2)n$ $CH_3$, $O(CH_2)n$ $NH_2$ or $O(CH_2)n$ $CH_3$, where n is from 1 to about 10; Ci to C10 lower alkyl, alkoxyalkoxy, substituted lower alkyl, alkaryl or aralkyl; Cl; Br; CN; $CF_3$; $OCF_3$; O—, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-$CH_2CH_2OCH_3$, also known as 2'-O-(2-methoxyethyl)] (Martin et al., *Helv. Chim. Acta* 78:486, 1995). Other preferred modifications include 2'-methoxy (2'-0-$CH_3$), 2'-propoxy (2'-$OCH_2$ $CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics, such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC, and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. See Kornberg, A., DNA Replication, W. H. Freeman & Co., San Francisco, 1980, pp 75-77; and Gebeyehu et al., Nucl. Acids Res. 15:4513, 1987. A "universal" base known in the art, e.g., inosine, can also be included. 5-Me-C substitutions have been shown to increase nucleic acid duplex stability by 0.6-1.2<0>C (Sanghvi, Y. S., in Crooke, S. T. and Lebleu, B., Eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science 254:1497-1500, 1991.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C), and uracil (U). Modified nucleobases comprise other synthetic and natural nucleobases, such as 5-methylcytosine (5-me-C), 5-hydroxymethyl cytosine, xanthine, hypoxanthine, 2-aminoadenine, 6-methyl, and other alkyl derivatives of adenine and guanine, 2-propyl and other alkyl derivatives of adenine and guanine, 2-thiouracil, 2-thiothymine, and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine, and 7-deazaadenine, and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., Ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines, and N-2, N-6 and 0-6 substituted purines, comprising 2-aminopropyladenine, 5-propynyluracil, and 5-propynylcytosine. 5-methylcytosine substitutions have been shown to increase nucleic acid duplex stability by 0.6-1.2° C. (Sanghvi, Crooke, and Lebleu, Eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175, 273; 5, 367,066; 5,432,272; 5,457,187; 5,459,255; 5,484,908; 5,502,177; 5,525,711; 5,552,540; 5,587,469; 5,596,091; 5,614,617; 5,750,692, and 5,681,941 (each of which is herein incorporated by reference).

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. U.S.A. 86:6553-6556, 1989), cholic acid (Manoharan et al., Bioorg. Med. Chem. Lett. 4:1053-1060, 1994), a thioether, e.g., hexyl-S-tritylthiol (Manoharan et al, Ann. N. Y. Acad. Sci. 660:306-309, 1992; Manoharan et al., Bioorg. Med. Chem. Lett. 3:2765-2770, 1993), a thiocholesterol (Oberhauser et al., Nucl. Acids Res. 20, 533-538, 1992), an aliphatic chain, e.g., dodecandiol or undecyl residues (Kabanov et al., FEBS Lett. 259:327-330, 1990; Svinarchuk et al., Biochimie 75:49-54, 1993), a phospholipid, e.g., di-hexadecyl-rac-glycerol or triethylammonium 1,2-di-O-hexadecyl-rac-glycero-3-H-phosphonate (Manoharan et al., Tetrahedron Lett. 36:3651-3654, 1995; Shea et al., Nucl. Acids Res. 18:3777-3783, 1990), apolyamine or a polyethylene glycol chain (Mancharan et al., Nucleosides & Nucleotides 14:969-973, 1995), or adamantane acetic acid (Manoharan et al., Tetrahedron Lett. 36:3651-3654, 1995), a palmityl moiety (Mishra et al., Biochim. Biophys. Acta 1264: 229-237, 1995), or an octadecylamine or hexylamino-carbonyl-t oxycholesterol moiety (Crooke et al., J. Pharmacol. Exp. Ther. 277:923-937, 1996). See also U.S. Pat. Nos. 4,828,979; 4,948,882; 5,218, 105; 5,525,465; 5,541,313; 5,545,730; 5,552, 538; 5,578, 717, 5,580,731; 5,580,731; 5,591,584; 5,109,124; 5,118, 802; 5,138,045; 5,414,077; 5,486, 603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082, 830; 5,112,963; 5,214,136; 5,082, 830; 5,112,963; 5,214,136; 5, 245,022; 5,254,469; 5,258, 506; 5,262,536; 5,272,250; 5,292,873; 5,317,098; 5,371, 241, 5,391, 723; 5,416,203, 5,451,463; 5,510,475; 5,512, 667; 5,514,785; 5, 565,552; 5,567,810; 5,574,142; 5,585, 481; 5,587,371; 5,595,726; 5,597,696; 5,599,923; 5,599, 928 and 5,688,941 (each of which is herein incorporated by reference).

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism, or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941 (each of which is incorporated by reference).

The inhibitory nucleic acids useful in the present methods are sufficiently complementary to the target miRNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a miRNA, then the bases are considered to be complementary to each other at that position. In some embodiments, 100% complementarity is not required. In some embodiments, 100% complementarity is required. Routine methods can be used to design an inhibitory nucleic acid that binds to the target sequence with sufficient specificity.

Target segments of 5, 6, 7, 8, 9, 10, 11, 12, 13, 14, 15, 16, 17 or more nucleotides in length comprising a stretch of at least five (5) consecutive nucleotides within the seed sequence 5'-ACAGUACU-3' (SEQ ID NO:3), or immediately adjacent thereto, are considered to be suitable for targeting as well. In some embodiments, target segments can include sequences that comprise at least the 5 consecutive nucleotides from the 5'-terminus of one of the seed sequence (the remaining nucleotides being a consecutive stretch of the same RNA beginning immediately upstream of the 5'-terminus of the seed sequence and continuing until the inhibitory nucleic acid contains about 5 to about 30 nucleotides). In some embodiments, target segments are represented by RNA sequences that comprise at least the 5 consecutive nucleotides from the 3'-terminus of one of the seed sequence (the remaining nucleotides being a consecutive stretch of the same miRNA beginning immediately downstream of the 3'-terminus of the target segment and continuing until the inhibitory nucleic acid contains about 5 to about 30 nucleotides). One having skill in the art armed with the sequences provided herein will be able, without undue experimentation, to identify further preferred regions to target. In some embodiments, an inhibitory nucleic acid contains a sequence that is complementary to at least 5, 6, 7, 8, 9, 10, 11, 12, 13, 14, 15, 16, 17, 18, 19, 20, 21, 22, 23, 24, or 25 continguous nucleotides present in the target (e.g., the target miRNA, e.g., mature or precursor hsa-miR-101-3p, or the target mRNA).

Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a miRNA molecule or an mRNA molecule, then the inhibitory nucleic acid and the miRNA or mRNA are considered to be complementary to each other at that position. The inhibitory nucleic acids and the miRNA or mRNA are complementary to each other when a sufficient number of corresponding positions in each molecule are occupied by nucleotides that can hydrogen bond with each other. Thus, "specifically hybridizable" and "complementary" are terms which are used to indicate a sufficient degree of complementarity or precise pairing such that stable and specific binding occurs between the inhibitory nucleic acid and the miRNA target. For example, if a base at one position of an inhibitory nucleic acid is capable of hydrogen bonding with a base at the corresponding position of a miRNA or a mRNA, then the bases are considered to be complementary to each other at that position. 100% complementarity is not required.

It is understood in the art that a complementary nucleic acid sequence need not be 100% complementary to that of its target nucleic acid to be specifically hybridizable. A complementary nucleic acid sequence for purposes of the present methods is specifically hybridizable when binding of the sequence to the target miRNA or mRNA molecule interferes with the normal function of the target miRNA or mRNA to cause a loss of expression or activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 370 C in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.10% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci. U.S.A. 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within a miRNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol. 215:403-410, 1990; Zhang and Madden, Genome Res. 7:649-656, 1997). Antisense and other compounds of the invention that hybridize to a miRNA or a mRNA are identified through routine experimentation. In general, the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to hsa-miR-101-3p. Thus, oligonucleotides are chosen that are sufficiently complementary to hsa-miR-101-3p, i.e., that hybridize sufficiently well and with sufficient specificity, to give the desired effect.

Modified Bases Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acid (LNA) molecules. Preferably, the modified nucleotides are locked nucleic acid molecules, including [alpha]-L-LNAs. LNAs comprise ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the base pairing reaction (Jepsen et al., Oligonucleotides 14:130-146, 2004). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., miRNAs and mRNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the miRNA or the mRNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34: e60, 2006; McTigue et al., Biochemistry 43:5388-405, 2004; and Levin et al., Nucl. Acids. Res. 34: e142, 2006. For example, "gene walk" methods, similar to those used to design antisense oligos, can be used to optimize the inhibitory activity of the LNA; for example, a series of oligonucleotides of 10-30 nucleotides spanning the length of a target miRNA or mRNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

In some embodiments, the LNA molecules can be designed to target a specific region of the miRNA. For example, a specific functional region can be targeted, e.g., a region comprising a seed sequence. Alternatively, or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol. 215:403-410, 1990; Zhang and Madden, Genome Res. 7:649-656, 1997), e.g., using the default parameters.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 2010/0267018; 2010/0261175; and 2010/0035968; Koshkin et al., Tetrahedron 54:3607-3630, 1998; Obika et al., Tetrahedron Lett. 39:5401-5404, 1998; Jepsen et al., Oligonucleotides 14:130-146, 2004; Kauppinen et al., Drug Disc. Today 2(3):287-290, 2005; and Ponting et al., Cell 136(4):629-641, 2009, and references cited therein.

Antagomirs

In some embodiments, the antisense is an antagomir. Antagomirs are chemically-modified antisense oligonucleotides that target a microRNA (e.g., target hsa-miR-101-3p). For example, an antagomir for use in the methods described herein can include a nucleotide sequence sufficiently complementary to hybridize to a miRNA target sequence of about 12 to 25 nucleotides, preferably about 15 to 23 nucleotides.

In general, antagomirs include a cholesterol moiety, e.g., at the 3-end. In some embodiments, antagomirs have various modifications for RNase protection and pharmacologic properties such as enhanced tissue and cellular uptake. For example, in addition to the modifications discussed above for antisense oligos, an antagomir can have one or more of complete or partial 2-O-methylation of sugar and/or a phosphorothioate backbone. Phosphorothioate modifications provide protection against RNase activity and their lipophilicity contributes to enhanced tissue uptake. In some embodiments, the antagomir can include six phosphorothioate backbone modifications; two phosphorothioates are located at the 5'-end and four at the 3'-end. See, e.g., Krutzfeldt et al., Nature 438:685-689, 2005; Czech, N. Engl. J. Med. 354:1194-1195, 2006; Robertson et al., Silence 1:10, 2010; Marquez and McCaffrey, Human Gene Ther. 19(1): 27-38, 2008; van Rooij et al., Circ. Res. 103(9):919-928, 2008; and Liu et al., Int. J. Mol. Sci. 9:978-999, 2008.

Antagomirs useful in the present methods can also be modified with respect to their length or otherwise the number of nucleotides making up the antagomir. In general, the antagomirs are about 20-21 nucleotides in length for optimal function, as this size matches the size of most mature microRNAs. The antagomirs must retain specificity for their target, i.e., must not directly bind to, or directly significantly affect expression levels of, transcripts other than the intended target.

In some embodiments, the inhibitory nucleic acid is locked and includes a cholesterol moiety (e.g., a locked antagomir).

siRNA

In some embodiments, the nucleic acid sequence that is complementary to a target miRNA or a target mRNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, 2002; Lee et al., Nature Biotechnol., 20, 500-505, 2002; Miyagishi and Taira, Nature Biotechnol. 20:497-500, 2002; Paddison et al., Genes & Dev. 16:948-958, 2002; Paul, Nature Biotechnol. 20, 505-508, 2002; Sui, Proc. Natl. Acad. Sci. U.S.A., 99(6):5515-5520, 2002; Yu et al., Proc. Natl. Acad. Sci. U.S.A. 99:6047-6052, 2002.

The target RNA cleavage reaction guided by siRNAs is highly sequence specific. In general, siRNA containing a nucleotide sequences identical to a portion of the target nucleic acid (i.e., a target region comprising the seed sequence of a miR-101-3p, e.g., a target region comprising SEQ ID NO:3) are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general, the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, *Ann. Rep. Med. Chem.* 30:285-294, 1995; Christoffersen and Marr, *J. Med. Chem.* 38:2023-2037, 1995). Enzymatic nucleic acid molecules can be designed to cleave specific miRNA or mRNA targets within the background of cellular RNA (Suryawanshi, et al. Molecular Biosystems. 6(10): 1807-9, 2010). Such a cleavage event renders the miRNA or mRNA non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its activity. After an enzymatic nucleic acid has bound and cleaved its RNA target, it is released from that RNA to search for another target and can repeatedly bind and cleave new targets.

Several approaches such as in vitro selection (evolution) strategies (Orgel, *Proc. R. Soc. London*, B 205:435, 1979) have been used to evolve new nucleic acid catalysts capable of catalyzing a variety of reactions, such as cleavage and ligation of phosphodiester linkages and amide linkages, (Joyce, *Gene*, 82, 83-87, 1989; Beaudry et al., *Science* 257, 635-641, 1992; Joyce, *Scientific American* 267, 90-97, 1992; Breaker et al., *TIBTECH* 12:268, 1994; Bartel et al., *Science* 261:1411-1418, 1993; Szostak, *TIBS* 17, 89-93, 1993; Kumar et al., *FASEB J.*, 9:1183, 1995; Breaker, *Curr. Op. Biotech.*, 1:442, 1996). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 rnM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Making and Using Inhibitory Nucleic Acids Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g., in vitro, bacterial, fungal, mammalian, yeast, insect, or plant cell expression systems.

Nucleic acid sequences of the invention (e.g., any of the inhibitory nucleic acids or sense nucleic acids described herein) can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)).

As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, herpes virus, adenovirus, adeno-associated virus, pox virus, or alphavirus. The recombinant vectors (e.g., viral vectors) capable of expressing the nucleic acids of the invention can be delivered as described herein, and persist in target cells (e.g., stable transformants). For example, such recombinant vectors (e.g., a recombinant vector that results in the expression of an antisense oligomer that is complementary to hsa-miR-101-3p can be administered into (e.g., injection or infusion into) the cerebrospinal fluid of the subject (e.g., intracranial injection, intraparenchymal injection, intraventricular injection, and intrathecal injection, see, e.g., Bergen et al., Pharmaceutical Res. 25:983-998, 2007). A number of exemplary recombinant viral vectors that can be used to express any of the nucleic acids described herein are also described in Bergen et al. (supra). Additional examples of recombinant viral vectors are known in the art.

The nucleic acids provided herein (e.g., the inhibitory nucleic acids) can be further be complexed with one or more cationic polymers (e.g., poly-L-lysine and poly(ethylenimine), cationic lipids (e.g., 1,2-dioleoyl-3-trimethylammonium propone (DOTAP), N-methyl-4-(dioleyl)methylpyridinium, and 3β-[N—(N',N'-dimethylaminoethane)-carbamoyl] cholesterol), and/or nanoparticles (e.g., cationic polybutyl cyanoacrylate nanoparticles, silica nanoparticles, or polyethylene glycol-based nanoparticles) prior to administration to the subject (e.g., injection or infusion into the cerebrospinal fluid of the subject). Additional examples of cationic polymers, cationic lipids, and nanoparticles for the therapeutic delivery of nucleic acids are known in the art. The therapeutic delivery of nucleic acids has also been shown to be achieved following intrathecal injection of polyethyleneimine/DNA complexes (Wang et al., Mol. Ther. 12:314-320, 2005). The methods for delivery of nucleic acids described herein are non-limiting. Additional methods for the therapeutic delivery of nucleic acids to a subject are known in the art.

In some embodiments, the inhibitory nucleic acids (e.g., one or more inhibitory nucleic acids targeting hsa-miR-101-3p) can be administered systemically (e.g., intravenously, intaarterially, intramuscularly, subcutaneously, or intraperitoneally) or intrathecally (e.g., epidural administration). In some embodiments, the inhibitory nucleic acid is administered in a composition (e.g., complexed with) one or more cationic lipids. Non-limiting examples of cationic lipids that can be used to administer one or more inhibitory nucleic acids (e.g., any of the inhibitory nucleic acids described herein) include: Lipofectamine, the cationic lipid molecules described in WO 97/045069, and U.S. Patent Application Publication Nos. 2012/0021044, 2012/0015865, 2011/0305769, 2011/0262527, 2011/0229581, 2010/0305198, 2010/0203112, and 2010/0104629 (each of which is herein incorporated by reference). Nucleic acid sequences used to practice this invention can be synthesized in vitro by well-known chemical synthesis techniques, as described in, e.g., Adams, J. Am. Chem. Soc. 105:661, 1983; Belousov, Nucleic Acids Res. 25:3440-3444, 1997; Frenkel, Free Radic. Biol. Med. 19:373-380, 1995; Blommers, Biochemistry 33:7886-7896, 1994; Narang, Meth. Enzymol. 68:90, 1994; Brown, Meth. Enzymol. 68:109, 1979; Beaucage, Tetra Lett. 22:1859, 1981; and U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2-modified nucleotide, e.g., a 2'-deoxy, 2'-deoxy-2'-fluoro, 2'-O-methyl, 2'-O-methoxyethyl (2'-O-MOE), 2-O-aminopropyl (2-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290, 2005; Koshkin et al., J Am. Chem. Soc., 120(50):13252-13253, 1998). For additional modifications see US 2010/0004320, US 2009/0298916, and US 2009/0143326 (each of which is incorporated by reference).

Techniques for the manipulation of nucleic acids used to practice this invention, such as, e.g., subcloning, labeling probes (e.g., random-primer labeling using Klenow polymerase, nick translation, amplification), sequencing, hybridization, and the like are well described in the scientific and patent literature, see, e.g., Sambrook et al., Molecular Cloning; A Laboratory Manual 3d ed. (2001); Current Protocols in Molecular Biology, Ausubel et al., Eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, Ed. Elsevier, N.Y. (1993).

Pharmaceutical Compositions

The methods described herein can include the administration of pharmaceutical compositions and formulations comprising any one or more (e.g., two, three, four, or five) of the inhibitory nucleic acids targeting hsa-miR-101-3p. In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives, and antioxidants can also be present in the compositions. In some embodiments, one or more cationic lipids, cationic polymers, or nanoparticles can be included in compositions containing the one or more inhibitory nucleic acids (e.g., compositions containing one or more inhibitory nucleic acids targeting hsa-miR-101-3p.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect.

Pharmaceutical formulations of this invention can be prepared according to any method known to the art for the manufacture of pharmaceuticals. Such drugs can contain sweetening agents, flavoring agents, coloring agents, and preserving agents. A formulation can be admixtured with nontoxic pharmaceutically acceptable excipients which are suitable for manufacture. Formulations may comprise one or more diluents, emulsifiers, preservatives, buffers, excipients, etc., and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., inhibitory nucleic acids or sense nucleic acids described herein) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth, and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long-chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame, or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as *arachis* oil, olive oil, sesame oil, or coconut oil, or in a mineral oil such as liquid paraffin; or a mixture of these.

See e.g., U.S. Pat. No. 5,716,928, describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin, or cetyl alcohol. Sweetening agents can be added to provide a palatable oral preparation, such as glycerol, sorbitol, or sucrose. These formulations can be preserved by the addition of an antioxidant such as ascorbic acid. As an example of an injectable oil vehicle, see Minto, J. Pharmacol. Exp. Ther. 281:93-102, 1997.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters, or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate, and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi, *J. Clin. Pharmacol.* 35:1187-1193, 1995; Tjwa, *Ann. Allergy Asthma Immunol.* 75:107-111, 1995). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao, *J. Biomater Sci. Polym. Ed.* 7:623-645, 1995; as biodegradable and injectable gel formulations, see, e.g., Gao, *Pharm. Res.* 12:857-863, 1995; or, as microspheres for oral administration, see, e.g., Eyles, *J. Pharm. Pharmacol.* 49:669-674, 1997.

In some embodiments, the pharmaceutical compounds can be parenterally administered, such as by intravenous (IV) administration or administration into a body cavity, a lumen of an organ, or into the cranium (e.g., intracranial injection or infusion) or the cerebrospinal fluid of a subject. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose, any bland fixed oil can be employed including synthetic mono- or diglycerides. In addition, fatty acids, such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate, and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid or a sense nucleic acid can be made by lyophilizing a solution comprising a pharmaceutical of the invention and a bulking agent, e.g., mannitol, trehalose, raffinose, and sucrose, or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5, but less than 6.5. See, e.g., US2004/0028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989.

The formulations of the invention can be administered for prophylactic and/or therapeutic treatments. In some embodiments, for therapeutic applications, compositions are administered to a subject who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to reduce the number of symptoms or reduce the severity, duration, or frequency of one or more symptoms of a neurodegenerative disorder in a subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age, and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones, J. Steroid Biochem. Mol. Biol. 58:611-617, 1996; Groning, Pharmazie 51:337-341, 1996; Fotherby, Contraception 54:59-69, 1996; Johnson, J. Pharm. Sci. 84:1144-1146, 1995; Rohatagi, Pharmazie 50:610-613, 1995; Brophy, Eur. J. Clin. Pharmacol. 24:103-108, 1983; Remington: The Science and Practice of Pharmacy, 21st ed., 2005). The state of the art allows the clinician to determine the dosage regimen for each individual patient, active agent, and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, and the like. The formulations should provide a sufficient quantity of active agent to effectively treat, prevent or ameliorate conditions, diseases, or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray, or inhalation. Actual methods for preparing parenterally or non-parenterally administrable formulations will be known or apparent to those skilled in the art and are described in more detail in such publications as Remington: The Science and Practice of Pharmacy, 21st ed., 2005.

Various studies have reported successful mammalian dosing using complementary nucleic acid sequences. For example, Esau C., et al., Cell Metabolism, 3(2):87-98, 2006, reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST $\frac{3}{4}$ 45, ALT $\frac{3}{4}$ 35) for all doses with the exception of the 75 mg/kg dose of miR-122 ASO, which showed a very mild increase in ALT and AST levels. They concluded that 50 mg/kg was an effective, non-toxic dose. Another study by Krutzfeldt J., et al., Nature 438, 685-689, 2005, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen et al., Nature 452, 896-899, 2008, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., any of the treatments of a cancer described herein. In some embodiments, the methods described herein can include administering to a subject a therapeutically effective amount of hematopoietic stem cells (HSCs) expressing a miR-101-3p inhibitory nucleic acid.

Recombinant Expression Vectors, Host Cells and Genetically Engineered Cells

Described herein are methods for generating HSCs that express a miR-101-3p inhibitory nucleic acid. In some embodiments, the HSCs expressing a miR-101-3p inhibitory nucleic acid have downregulated levels of Tet1. The present inventors found that Tet1 overexpression in HSCs dramatically increases the differentiation of HSCs towards NKT and γδT cells and restores the impaired immunosurveillance against colorectal cancer in hypercholesterolemic and WT mice. Based on these findings, the present methods can be used to provide human HSCs expressing a miR-101-3p inhibitory nucleic acid for cancer immunotherapy by manipulating Tet1, a master epigenetic regulator of HSC differentiation towards NKT and γδT cells. In some embodiments, the HSCs are obtained from a subject who is in need of, or who has been determined to be in need of, such treatment, i.e., the cells are autologous; alternatively, they can be allogeneic. Methods for obtaining enriched populations of HSC are known in the art and include cell sorting based on expression of one or more cell surface markers; in some embodiments, the HSC used in the present methods are CD34+; in some embodiments, the cells are CD34+, Thy-1+; in some embodiments, the cells are CD34+, CD59+, Thy1/CD90+, CD38lo/−, C-kit/CD117+, and/or lin−. For example, primary human CD34+-enriched cells can be obtained from peripheral blood, e.g., after treatment of the donor with a mobilizing cytokine such as granulocyte-colony stimulating factor (GCSF). Other sources of HSC include bone marrow and umbilical cord blood. A number of methods are known in the art for preparing enriched populations of HSC, e.g., as described in Rector et al., Methods Mol Biol. 2013; 976:1-15. For example, the cells can be sorted, e.g., using columns (e.g., the MiniMACS LS+separation columns (Miltenyi Biotec, Auburn, Calif.)), e.g., using commercially available kits, e.g., the CD34-progenitor cell isolation kit (StemCell Technologies, Vancouver, BC, Canada), according to the manufacturer's protocol. A population of cells that is enriched for HSCs is at least 20% HSC, e.g., is at least 30%, 40%, 50%, 60%, 70%, 80%, 90%, or 95% HSCs. In some embodiments, the HSCs used in the present methods are obtained by enriching for cells that are CD34+; in some embodiments, the cells are obtained by enriching for cells that are CD34+, Thy-1+; in some embodiments, the cells are obtained by enriching for cells that are CD34+, CD59+, Thy1/CD90+, CD38lo/−, C-kit/CD117+, lin−.

Generally speaking, the HSCs are engineered to express a miR-101-3p inhibitory nucleic acid by transduction with a nucleic acid, e.g., expression vectors, containing a nucleic acid encoding a miR-101-3p inhibitory polypeptide described herein. As used herein, the term "vector" refers to a nucleic acid molecule capable of transporting another nucleic acid to which it has been linked and can include, e.g., a plasmid, cosmid or viral vector. The vector can be capable of autonomous replication or it can integrate into a host DNA. Viral vectors include, e.g., replication defective retroviruses, recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or CaPO$_4$ precipitation carried out in vivo.

A preferred approach for introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors can provide effective delivery of genes into cells. Whereas the transgene within a retroviral vector is typically stably integrated into the chromosomal DNA of the host, the transgene of an AAV vector usually exists as extrachromosomal episomes within the cytoplasm of infected cells. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, Blood 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology*, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

Typically, an expression vector includes the nucleic acid in a form suitable for expression of the miR-101-3p inhibitory nucleic acid in a HSC. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the level of expression of protein desired and whether regulated or inducible expression is desired. The expression vectors can be introduced into HSCs. The expression vector is preferably a vector suitable for expression in mammalian cells, and the expression vector's control functions can be provided by viral regulatory elements. For example, commonly used promoters are derived from polyoma, Adenovirus 2, cytomegalovirus and Simian Virus 40. See, e.g., Wang et al., Exp Hematol. 2008 July; 36(7):823-31.

In another aspect the invention provides HSC that include and optionally express a miR-101-3p inhibitory nucleic acid described herein, e.g., a miR-101-3p inhibitory nucleic acid molecule within a recombinant expression vector or a miR-101-3p inhibitory nucleic acid containing sequences which allow it to homologously recombine into a specific site of the HSC's genome. The term HSC refers not only to the particular subject cell that is transduced but to the progeny or potential progeny of such a cell that contain the miR-101-3p inhibitory nucleic acid. Because certain modifications may occur in succeeding generations due to either mutation or environmental influences, such progeny may not, in fact, be identical to the parent cell, but are still included within the scope of the term as used herein.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

In another aspect, the invention features an HSC cell or purified preparation of HSCs that express miR-101-3p inhibitory nucleic acids or express miR-101-3p inhibitory nucleic acids in response to a stimulus.

The methods can also include identifying, selecting, and/or purifying those cells that express miR-101-3p inhibitory nucleic acids, or that express miR-101-3p inhibitory nucleic acids over a desired level.

The HSCs expressing a miR-101-3p inhibitory nucleic acid can be used for administration to a subject, can be frozen or otherwise stored for later administration to a subject, or can be maintained under conditions such that the HSC differentiate into NKT and γδ T cells. These conditions can include those previously described. For example, c-kit+ Sca-1+Lin− (KSL) HSCs can be seeded, e.g., at $4\times10^3$ cells/well into 12-well tissue culture plates, containing a confluent monolayer of OP9-DL1 cells; see, e.g., Holmes and Zuniga-Pflucker, Cold Spring Harb Protoc 2009(2009)). In some embodiments, the cultures are performed in the presence of one or more cytokines or growth factors, e.g., 5 ng/mL IL-2, 10 ng/mL GM-CSF (Stem cell Technology), 5 ng/mL, IL-7, and 5 ng/mL mFLT3 (Peprotech).

NKT cells can be identified by methods known in the art, e.g., by the presence of TCRβ and NK1.1 or CD1d-tet (see, e.g. Godfrey et al., Nature Reviews Immunology 4, 231-237 (2004)); γδ T cells can be identified by methods known in the art, e.g., by the presence of γδ TCR (see, e.g., Holtmeier and Kabelitz, Chemical Immunology and Allergy 86: 151-83 (2005)). The cells can be maintained in culture until a desired number of cells, e.g., of HSC or NKT and γδ T cells, is obtained, and then harvested for use or freezing. The methods can also include purifying the NKT and/or γδ T cells away from the HSC expressing a miR-101-3p inhibitory nucleic acid, to provide purified populations of NKT and/or γδ T cells.

EXAMPLES

The invention is further described in the following examples, which do not limit the scope of the invention described in the claims.

Example 1. Materials and Methods

The following materials and methods were used in the examples set forth herein.

Mice

All mice were purchased from Jackson Laboratories (Bar Harbor, Me.) and were maintained in a mouse barrier facility. Care of mice was in accordance with NIH guidelines and the Institutional Animal Care and Use Committee of the University of Massachusetts Medical School approved all protocols. Mice were kept on a 12 hr day/night schedule and were allowed free access to chow and water. ApoE$^{-/-}$ and WT mice were fed standard mouse chow (5.4 g fat/100 g diet, 0% cholesterol). HCD mice were fed a diet with 10 g fat/100 g diet, 11.25 g cholesterol/100 g diet (Research Diets, New Brunswick, N.J.). NAC was given for 8 weeks (150 mg/kg/day via drinking water).

Cell Lines 293T (CRL-3216) cell lines were obtained from the ATCC repository. Cell line characterization by ATCC is conducted by STR analysis. OP9-DL1 cells were kindly provided by Dr. Juan Carlos Zúñiga-Pflücker (University of Toronto, Toronto, Canada). Upon receiving the cell lines, frozen stocks were prepared within one to five passages and new stocks were thawed frequently. The cell lines were passaged for less than 3 months after receipt or resuscitation. Cells were authenticated by morphology, phenotype, and growth, routinely screened for *mycoplasma*.

Tumor Induction and Analysis

The colorectal cancer was performed as described in previous publications 14. Three month old mice were subcutaneously (s.c.) injected with a solution of Azoxymethane (AOM) at a dose rate of 15 mg/kg body weight, once weekly for 3 successive weeks. 2% DSS was given in the drinking water over five days in the last week. Mice were sacrificed ten weeks after the last injection of AOM. Colons were removed and flushed with PBS. Sections (5 μm) were cut stepwise (200 μm) through the complete block and stained with H&E. Tumor counts were performed in a blinded fashion. To determine the histopathologic stages of tumors, the sections of tumors were read by cancer pathologists in a blind fashion.

Flow Cytometry and HSC Isolation

Cells were stained with monoclonal antibodies conjugated to various fluoroprobes. These antibodies included: cKit (2B8), Sca-1 (E13-161.7), CD4 (L3T4), CD8 (53-6.72), CD90.1, CD25, CD44, TCRβ, NK1.1, γβTCR, CD45.1, CD45.2. The lineage cocktail consisted of CD4, CD8, B220 (RA3-6B2), TER-119, Mac-1 (MI/70), and Gr-1 (RB6-8C5). All antibodies were purchased from BD Bioscience (San Diego, Calif.). CD1d-GalCer tetramer was obtained from the NIH Tetramer facility. FACS analysis was carried out on a FACS Diva or MoFlow. HSCs were isolated from the bone marrow and defined as cKit+ sca-1+ CD90.1lo/− Lin−, (KTLS).

Lentiviral Particle Preparation and Transduction

The Tet1 specific and control shRNA plasmids were both purchased from Santa Cruz (CA, USA). The plasmid with Tet1 catalytic domain (pTYF-U6-shCONT-EF1-Puro-2A-CD1) was a gift from Dr Yi Zhang (Boston Children's Hospital, Boston, Mass.). The envelope and helper plasmids were purchased from ABM (Toronto, Canada). The lentiviral particles were prepared according to the kit instructions. The lentivirus-containing supernatant was harvested 2 days post-transfection. Fresh isolated KSL cells were transduced with lentivirus for 24 hours and then selected with puromycin (2 μg/ml) (Santa Cruz Biotechnology, CA, USA) for 72 hours.

Preparation of oxLDL

Figure 12A:
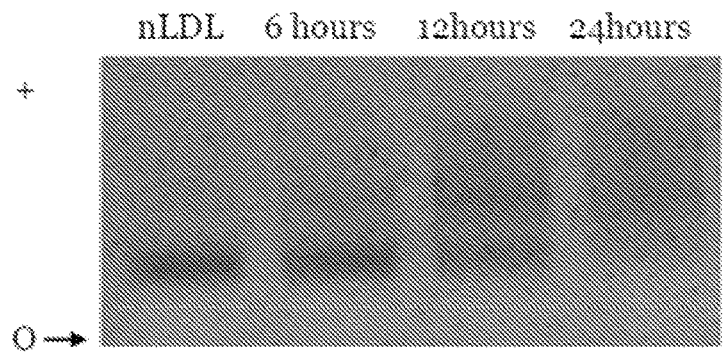
FIGS. 12A-B. WT recipient mice reconstituted with HSCs from hypercholesterolemic ApoE$^{-/-}$ mice have normal serum cholesterol levels and white blood cell counts. A, The mobility of nLDL and oxLDL preparations oxidized with CuSO4 for 6 hours, 12 hours and 24 hours. O is the place for loading. B, TBARS levels in nLDL and oxLDL preparations oxidized with CuSO4 for 6 hours, 12 hours and 24 hours.
Figure 12B:
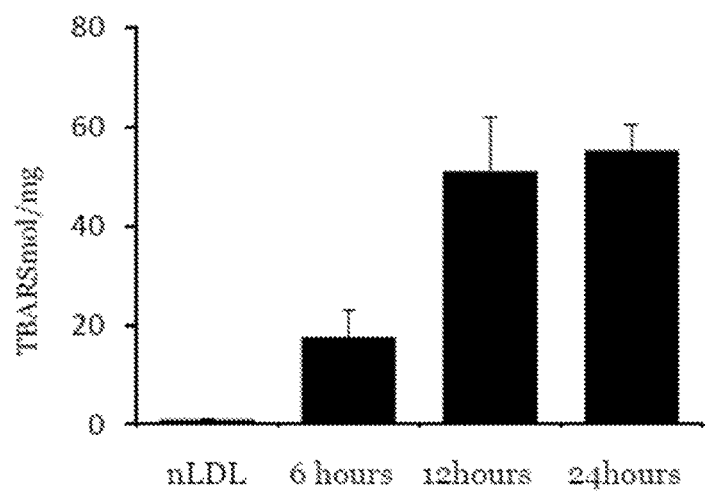

Native LDL (nLDL) was purchased from Sigma. OxLDL was prepared by incubating nLDL with 10 μM CuSO4 at 37° C. for 24 hours. The material was dialyzed against a sterile solution (150 mM NaCl, 1 mM EDTA, 100 μg/ml polymyxin B, pH7.4) and then sterilized by filtration. The extent of LDL oxidation was estimated by agarose gel electrophoresis and by measuring the amount of thiobarbituric acid reactive substances generated (FIGS. 12A, B).

HSCs and OP9 Cell Co-Culture

The co-culture was performed as described 15, 16. KSL (cKit+sca-1+CD90.1lo/−Lin−) cells were seeded at 4×103 cells/well into 12-well tissue culture plates containing a confluent monolayer of OP9-DL1 cells. OP9-DL1 cells were a kind gift from Dr. Juan Carlos Zuniga-Pflucker (University of Toronto). All cultures were performed in the presence of 5 ng/mL IL-2, 10 ng/mL GM-CSF (Stem cell Technology), 5 ng/mL IL-7, 5 ng/mL mFLT3 (Peprotech). Co-cultures were harvested by forceful pipetting at the indicated time points.

Immunohistochemistry

We used a standard protocol to detect NKT and γδT cells in colon and tumor tissues. The antibodies were purchased from BD Biosciences (MA, USA). For indirect immunohistochemistry, we used rabbit-specific IgG conjugated with FITC or PE (Chemicon) as a secondary antibody. For nuclear staining, we treated specimens with DAPI (Molecular Probes). Fluorescent images were obtained using a confocal laser scanning microscope (Carl Zeiss LSM 510 system; Carl Zeiss).

Chromatin Immunoprecipitation (ChIP)

ChIP was performed as following: approximately $1 \times 10^6$ HSCs were incubated for 10 min at room temperature with 1% formaldehyde. After cross-linking, the reaction was quenched with 0.25 M glycine for 10 min at room temperature. Proteins were initially cross-linked to DNA and nuclei were then pelleted and sonicated to 200-500 bp fragments (Bioruptor, Diagenode). The cross-linked DNA was immunoprecipitated with H3K4me3 antibody (Millipore, USA) overnight at 4° C. with rotation. DNA-Antibody complexes were bound to ChIP beads, pulled down, washed and then eluted from beads. Following reversal of cross-linkage, purified DNA was used for Quantitative PCR using ChIP PCR primers which were purchased from IDT (MA, USA). Immunoprecipitation efficiency was calculated by normalizing sample CT values against control IgG values and calculating ratios of sample CT values relative to input values.

qRT-PCR

We reverse transcribed cDNAs from total RNA isolated from each cell fraction using RNAqueous-Micro kit (Ambion). Transcription to cDNA was performed using SuperScript III (Invitrogen). All PCRs were carried out in triplicate using an Eppendorf Mastercycler (Eppendorf).

DNA Extraction, Bisulfite Conversion and Pyrosequencing

Genomic DNA was extracted from hematopoietic stem cells using standard phenol/chloroform extraction followed by isopropanol precipitation and ethanol wash and quantified by NanoDrop Spectrophotometer. 500 ng of DNA was used in the bisulfite conversion reactions where unmethylated cytosines were converted to uracil with the EZ DNA Methylation Gold™ kit (Zymo Research) according to manufacturer's instructions. Briefly, DNA was mixed with CT conversion reagents and the conversion was run in a thermocycler (Biometra, Goettingen, Germany) at the recommended cycle conditions. Converted DNA was purified on a spin column and eluted into a total of 10 μl Buffer EB. PCR and pyrosequencing Primer sets with one biotin-labelled primer were used to amplify the bisulfite converted DNA. New primers for each gene were designed using PyroMark Assay Design software version 2.0.1.15 (Qiagen). The size of the amplicons was around 100-200 bp.

PCRs were performed using a converted DNA by 2×HiFi Hotstart Uracil+Ready Mix RCR kit (Kapa Biosystems). Briefly, 5 μl master mix, 5 pmol of each primer, 20 ng genomic DNA and ultra-pure water to a final volume of 10 μl were mixed for each reaction and run at thermal cycling conditions: 95° C. for 3 min and then 50 cycles: 20 sec at 98° C.; 15 sec at the optimized primer-specific annealing temperature; 15 sec at 72° C. and a final extension for 1 min at 72° C. The amplified DNA was confirmed by electrophoresis in a 2% agarose gel. 2 μl streptavidin beads (GE Healthcare, Buckinghamshire, UK), 40 μl PyroMark binding buffer, 10 μl PCR product and 28 μl water were mixed and incubated for 10 min on a shaking table at 1300 rpm. Using the Biotage Q96 Vacuum Workstation, amplicons were separated, denatured, washed and added to 25 μl annealing buffer containing 0.33 μM of pyrosequencing primer. Primer annealing was performed by incubating the samples at 80° C. for 2 min and allowed to cool to room temperature prior to pyrosequencing. PyroGold reagents were used for the pyrosequencing reaction and the signal was analyzed using the PSQ 96MA system (Biotage, Uppsala, Sweden). Target CGs were evaluated by instrument software (PSQ96MA 2.1) which converts the pyrograms to numerical values for peak heights and calculates percentage of methylation at each base as a C/T ratio.

MiRNA Microarray Expression Profiling

HSCs were isolated as described. Total RNA was isolated using the mirVana miRNA isolation kit according to manufacturer's instructions (Applied Biosystems). RNA quality and quantity were analyzed by NanoDrop ND-1000 spectrophotometer and PicoRNA kit (Invitrogen). miRNA expression was measured by Affymetrix miRNA 3.0 array (Affymetrix, Santa Clara, Calif., USA). The sample labeling, microarray hybridization and washing were performed based on manufacturer's standard protocols. Briefly, total RNA were tailed with Poly A and then labeled with Biotin. Afterwards, the labeled RNAs were hybridized onto the microarray. Having washed and stained the slides, the arrays were scanned by the Affymetrix Scanner 3000 (Affymetrix). The scanned images were analyzed using Expression Console software (version 1.3.1 Affymetrix). According to microarray results and literature, candidate miRNAs were chosen for further validation with qRT-PCR.

Probe summarization and normalization were calculated from raw.cel files according to manufacturer's recommendations using miRNA QC Tool v 1.1.1.0. Data quality was also checked using Box- and Whisker-plots that showed expected normalized means and standard deviations among the datasets, except for five probes identified as outliers, which were removed from further analysis. MiRNAs were first filtered so that analysis was performed with only well measured genes, i.e. those that contained expression in at least 2 samples. Then for unsupervised analysis (principle component analysis or 2-way hierarchical clustering) three different ranking and filtering methods were used to identify a list of miRNAs that contained the most variance: 1. Coefficient of variation (CV); 2. Standard deviation; 3. Filtering for at least 2-3 samples with 1-2 standard deviations above and below the mean. After filtering, data was log 2 transformed, and Pearson's correlations were iteratively calculated between all miRNA expression values for all probes and samples for 2-way hierarchical clustering. For supervised analysis, a Student's t-test was used to identify differentially expressed miRNAs. The False Discovery Rate or q values were calculated using the Storey method to adjust for type 1 errors with a predicted false discovery rate of <20%. The microarray data are MIAME compliant and have been deposited into the NCBI gene expression Omnibus. Data can be accessed through autonomous.ncbi.nlm.nih.gov/geo (GSE79361).

miRNA Target Prediction

The predicted target genes of differentially expressed miRNAs were obtained using the following tools: TargetScan v6.2 and miRDB. The search was performed on the 3'-UTR regions of target mRNAs with a P value of 0.05 defining the probability distribution of random matches set in the software with a minimum miRNA seed length of 7.

mRNA 3'-UTR Cloning and Luciferase Reporter Assay

HEK293T cells grown in 96-well plates were transfected with pmirGLO vector tagged with Tet1 3' UTRs that includes miR101c binding sites co-transfected with or without miR101c by using Lipofectamine (Invitrogen). The Firefly and Renilla luciferase activities in the cell lysates were assayed with a Dual-Luciferase Reporter Assay System (Promega) at 48h post-transfection. To generate the mutant variants, point mutations in the binding sites of miR101c in 3'-UTR of Tet1 were introduced by PCR according to the site mutation protocol from Agilent.

Statistical Analysis

All data were shown as means±sd. Statistical analyses were carried out with either GraphPad Prism (GraphPad Software) or SPSS v19 (IBM) software. Statistical significance was evaluated by using a one- or two-way analysis of variance (ANOVA) or an unpaired t-test. Significance was established for P values of at least <0.05.

Example 2. Hypercholesterolemia Increases the Incidence and Histopathologic Severity of Colorectal Cancer by an HSC-Autonomous Mechanism We first induced colorectal cancer with azoxymethane (AOM) in two common mouse models of hypercholesterolemia, the ApoE$^{-/-}$ mouse and the C57BL/6 mouse fed a high cholesterol diet (HCD). The average tumor number was almost two fold higher in hypercholesterolemic mice than in WT mice (FIG. 1A).

Figure 1B:
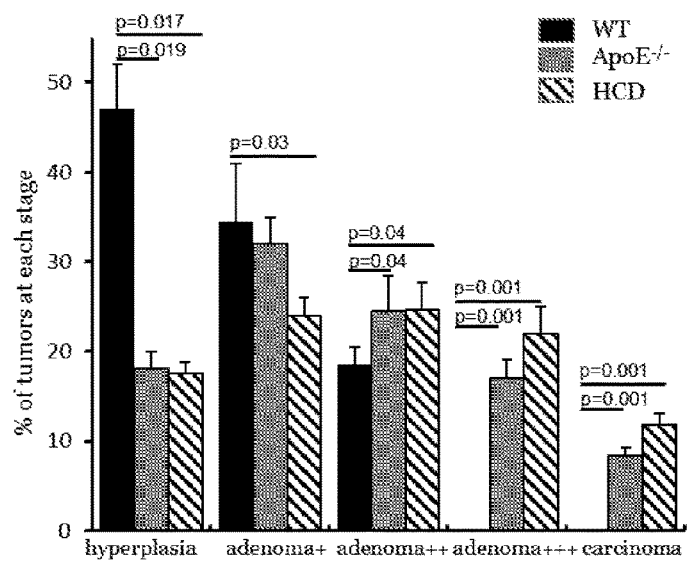

The tumors in the hypercholesterolemic mice were at a more advanced histopathological stage than those in WT mice. In hypercholesterolemic mice more tumors advanced to the adenoma+++ and carcinoma. The tumors at late stages of tumorigenesis were not found in WT control mice, but constituted more than 10% of the tumors found in hypercholesterolemic mice. Meanwhile the tumors at the early stages of tumorigenesis, including hyperplasia and adenoma+, were dramatically reduced in hypercholesterolemic mice (FIG. 1B). These results confirm that hypercholesterolemia increases the incidence and pathological severity of colorectal cancer in two independent mouse models of hypercholesteremia.

In order to determine if hypercholesterolemia-induced oxidant stress causes an HSC-autonomous defect that increases the incidence of colorectal cancer by impairing HSC lineage specification towards NKT and γδT cells, we induced colorectal cancer in a chimeric model whereby hematopoiesis was reconstituted in lethally irradiated WT recipient mice (CD45.1) with HSCs (cKit$^+$sca-1$^+$CD90.1$^{lo/-}$ Lin$^-$, KTLS) from either ApoE$^{-/-}$ or WT mice. In the lethally irradiated recipient WT mice that received HSCs from hypercholesterolemic mice, the thymus was repopulated with immune cells that were derived from the donor (CD45.2) HSCs (FIG. 1E). As expected, the serum cholesterol and white blood cell counts of the recipient mice were normal and comparable to those of WT mice (FIGS. 1F, G).

Figure 1C:
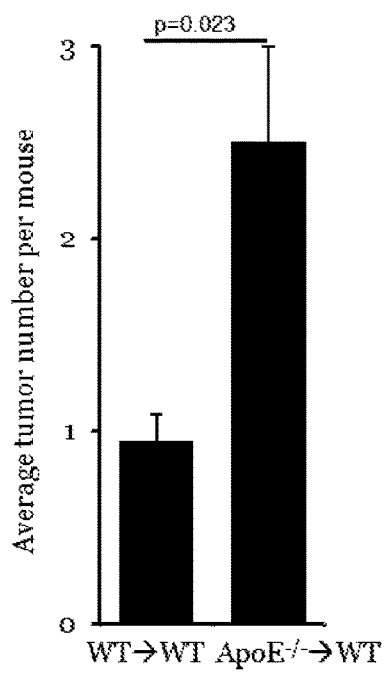
Figure 1D:
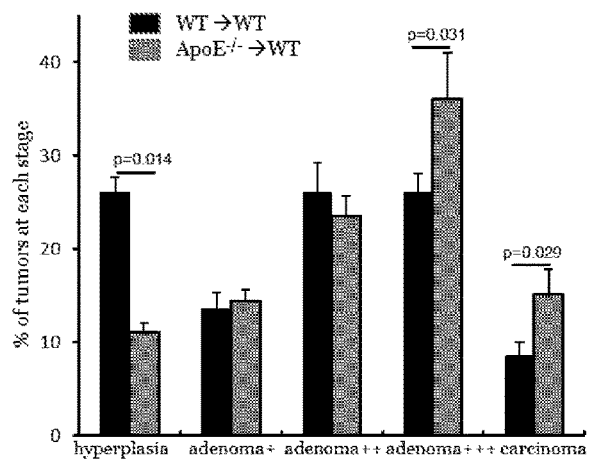

Despite normal serum cholesterol levels, the average tumor number and their histopathologic severity was significantly greater in lethally irradiated WT recipients when transplanted with HSCs from ApoE$^{-/-}$ mice than in those that received HSCs from WT mice (FIGS. 1C, D). Thus, both chimeric models in which lethally irradiated WT mice received HSCs from ApoE$^{-/-}$ mice recapitulated the increased tumor incidence and greater histopathologic severity seen in hypercholesterolemic mice, despite the absence of hypercholesterolemia. These results show that the increased incidence of colorectal cancer in hypercholesterolemic mice is due to a HSC-autonomous mechanism.

Example 3. The Differentiation of HSCs Towards NKT and γδT Cells is Reduced in Hypercholesterolemic Mice Upon TCR activation, NKT and γδT cells rapidly secrete a variety of cytokines that are critical for the anti-tumor functions of cytotoxic T cells. In addition to the cytokines produced by antigen-presenting cells with which NKT and γδT cells interact, these cytokines recruit and stimulate the anti-tumor functions of cytotoxic T cells, boosting innate as well as adaptive anti-tumor responses. Activated NKT and γδT cells both have strong cytotoxic effector activity (Chien Y H. et al. 2014; Taniguchi M. et al 2003; Todaro, M. et al. 2009). In this context, NKT and γδT cells function as major participants in tumor immunosurveillance.

Figure 2A:
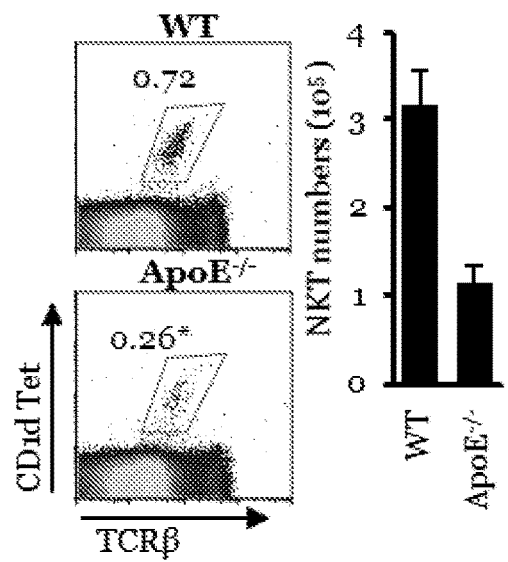
FIGS. 2A-J. Hypercholesterolemia significantly impairs the differentiation of HSCs towards NKT and γδT cells that are critical components of innate immunity against colorectal cancer. A, Frequency and total number of NKT cells in thymus of WT and ApoE$^{-/-}$ mice. n=8, *, p<0.05, vs. WT. B, Frequency and total number of γδT cells in thymus of WT and ApoE$^{-/-}$ mice. n=8, *, p<0.05, vs. WT. C, Frequency and total number of NKT cells in thymus of lethally irradiated WT recipients reconstituted with HSCs from WT or ApoE$^{-/-}$ mice. n=8, *, p<0.05, vs. WT→WT. D, Frequency and total number of γδT cells in thymus of lethally irradiated WT recipients reconstituted with HSCs from WT or ApoE$^{-/-}$ mice. n=8, *, p<0.05, vs. WT→WT. E, Frequency of submucosal NKT cells in colon of WT and ApoE$^{-/-}$ mice. n=8, , p<0.01, vs. WT. F, Frequency of submucosal γδT cells in colon of WT and ApoE$^{-/-}$ mice. n=8, , p<0.01, vs. WT. G, Average tumor number and histopathologic stage of AOM induced colorectal cancer in CD1d$^{-/-}$ mice. n=10, *, p<0.05; **, p<0.01, vs. WT BalbC or WT C57BL6. H, Average tumor number and histopathologic stages of AOM induced colorectal cancer in Tcrd$^{-/-}$ mice. n=10, *, p<0.05; **, p<0.01, vs. WT BalbC or WT C57BL6. I, Frequency of NKT cells in the tumors from WT and ApoE$^{-/-}$ mice. n=8, *, p<0.05; **, p<0.01, vs. WT. J, Frequency of γδT cells in the tumors from WT and ApoE$^{-/-}$ mice. n=8, *, p<0.05; **, p<0.01, vs. WT.
Figure 2B:
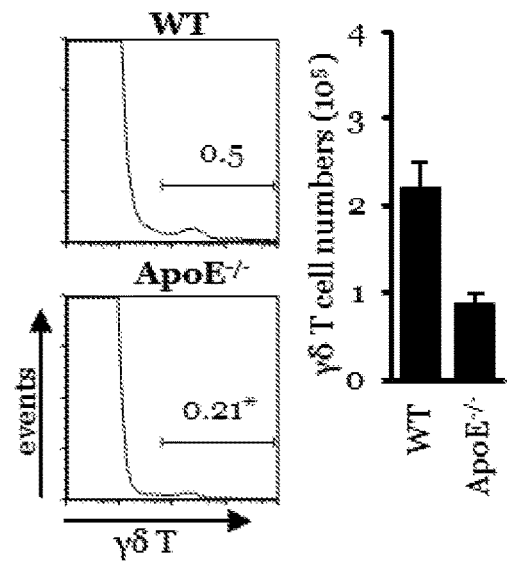
Figure 2C:
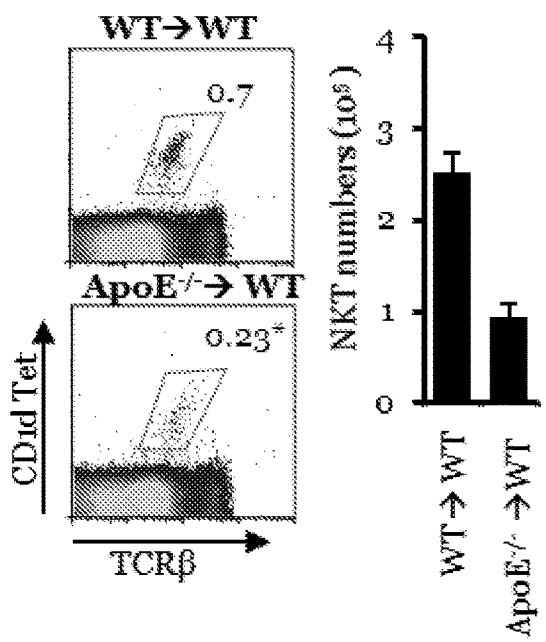
Figure 2D:
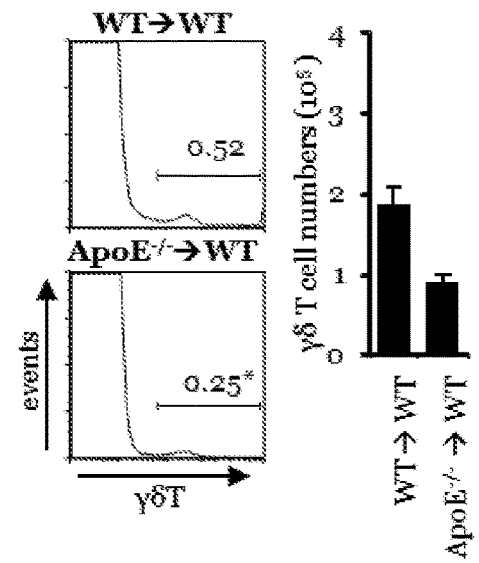
Figure 3A:
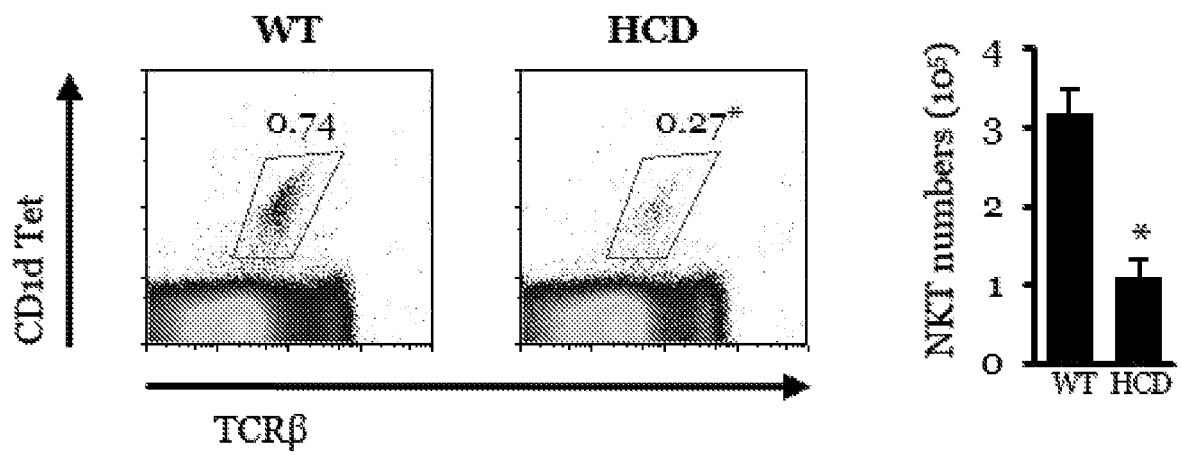
Figure 3B:
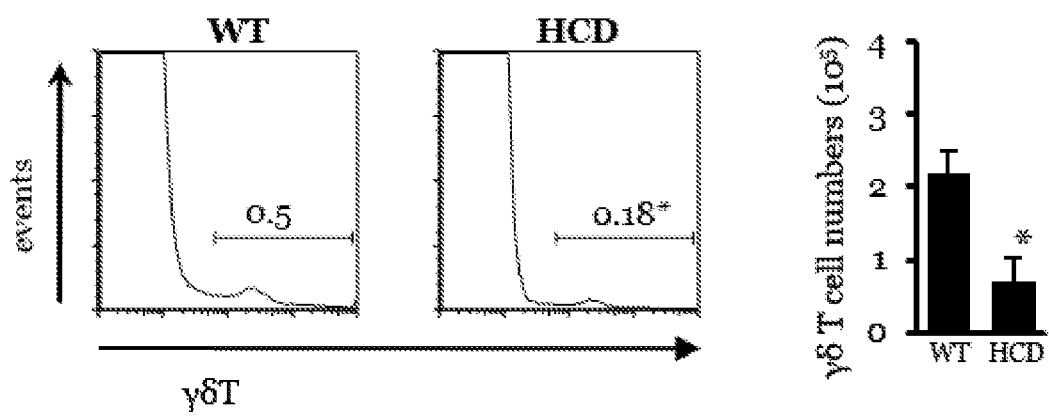
Figure 3C:
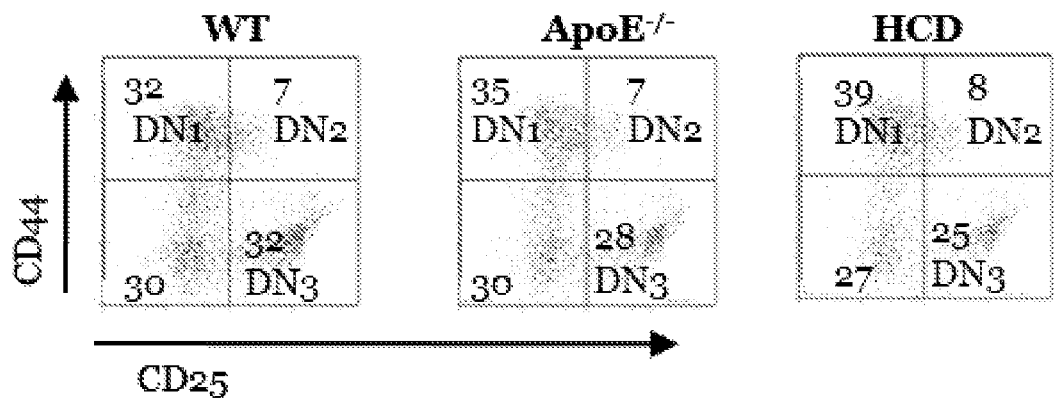
Figure 3D:
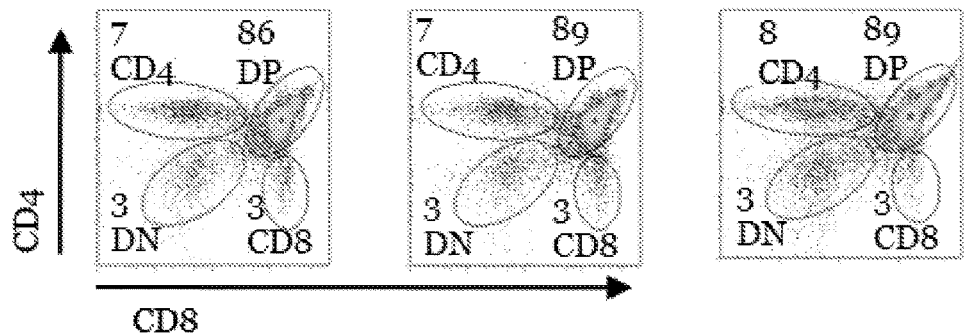
Figure 3G:
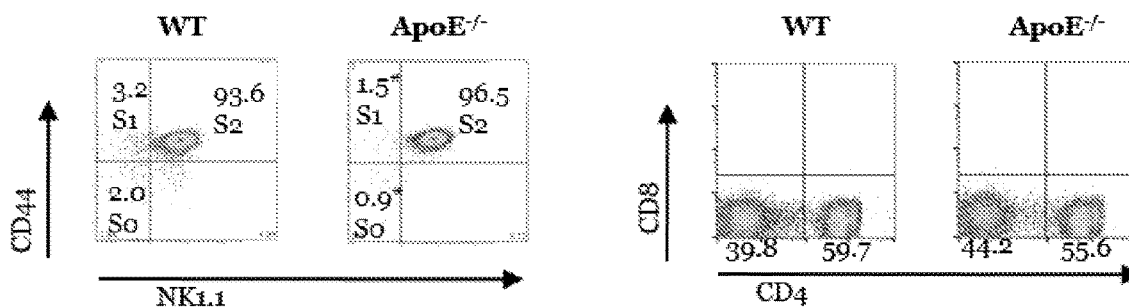
Figure 3G:
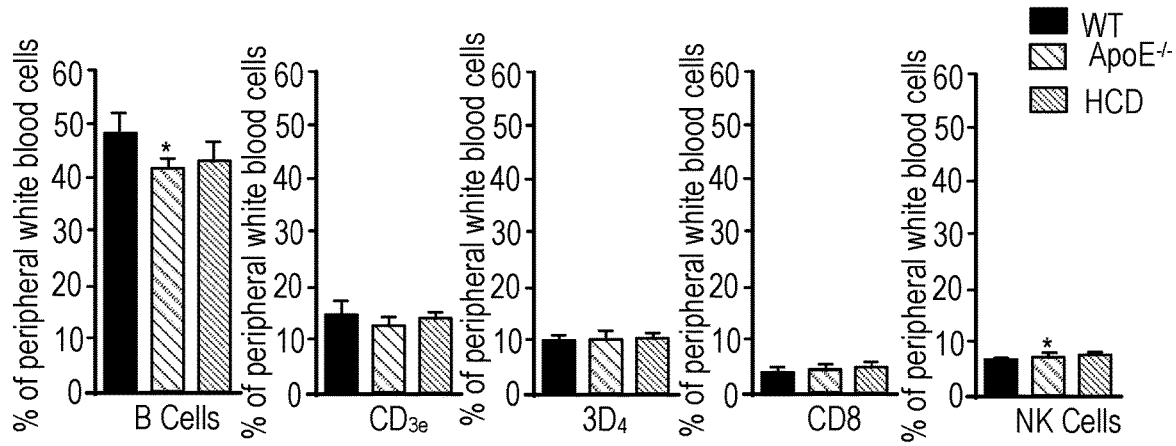

The populations of γδT cells and NKT cells in the thymus were significantly lower in hypercholesterolemic mice than in WT mice (FIGS. 2A, B; FIGS. 3A, B). In contrast, γδT cell developmental intermediates were similar to WT mice in all groups (FIG. 3C, D). Similarly, intrathymic NKT cell development in ApoE$^{-/-}$ mice was identical to WT at phases 1 (CD44-NK1.1$^-$) and 2 (CD44$^+$NK1.1$^-$) (FIG. 3E) as well as the CD4 subsets of NKT cells (FIG. 3F). Except for a slight decrease in B cells and a slight increase in NK cells, FACS analysis did not show any significant change in CD3e$^+$, CD4$^+$ and CD8$^+$ T cell populations in peripheral blood of hypercholesterolemic mice (FIG. 3G). In the thymus of WT recipient mice reconstituted with HSCs from ApoE$^{-/-}$ mice, we observed a nearly identical decrease in differentiation toward NKT and γδ T cells as that seen in ApoE$^{-/-}$ mice (FIGS. 2C, D). These results indicated that hypercholesterolemia specifically induced a cell-autonomous reduction in lineage specification of HSCs towards NKT and γδ T cells.

Figure 2E:
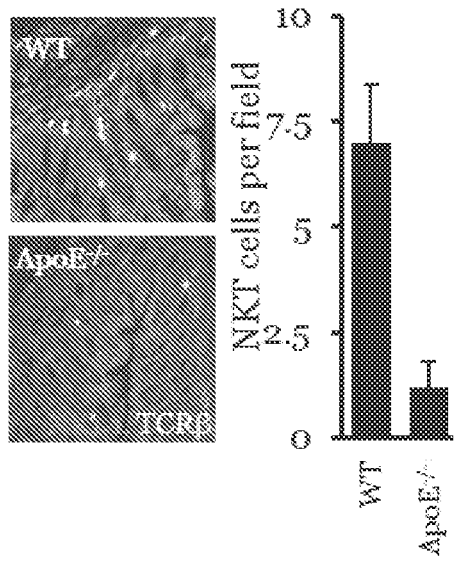
Figure 2F:
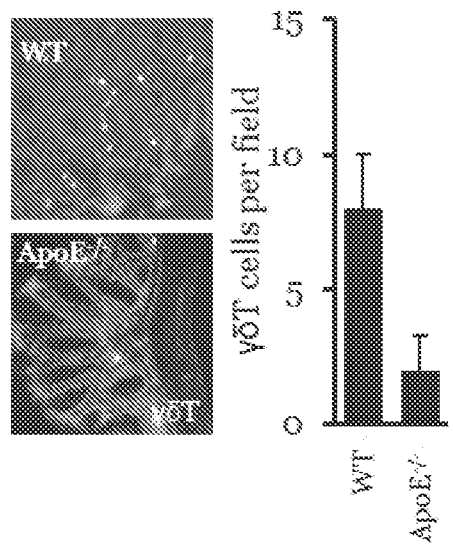
Figure 2G:
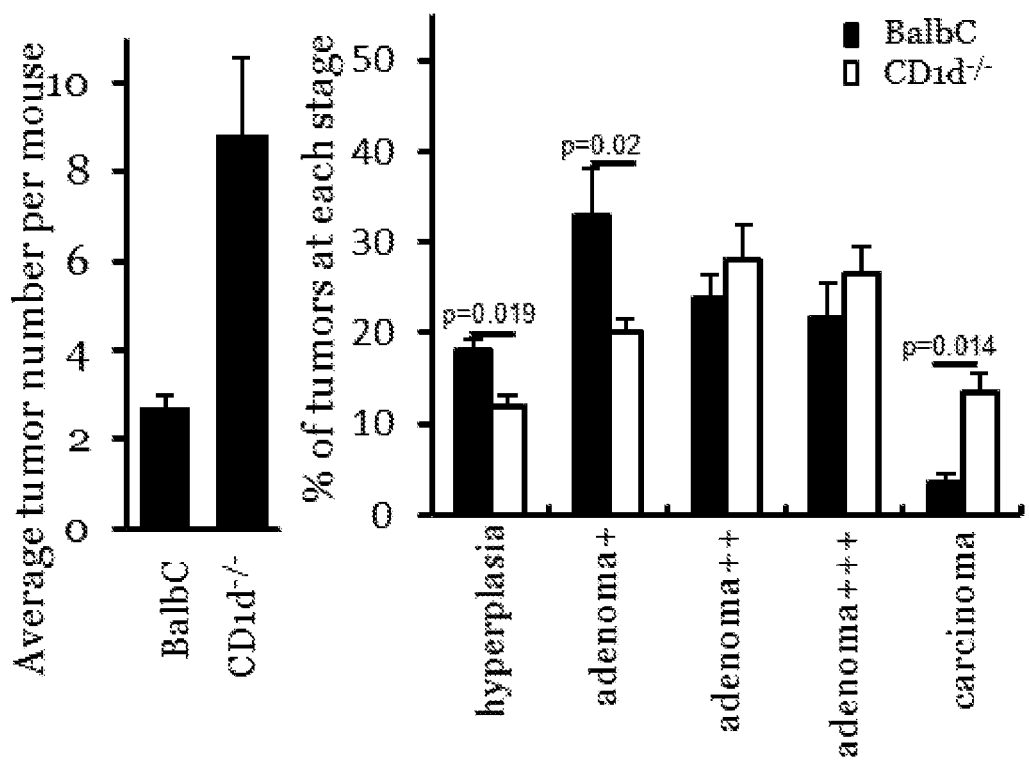
Figure 2H:
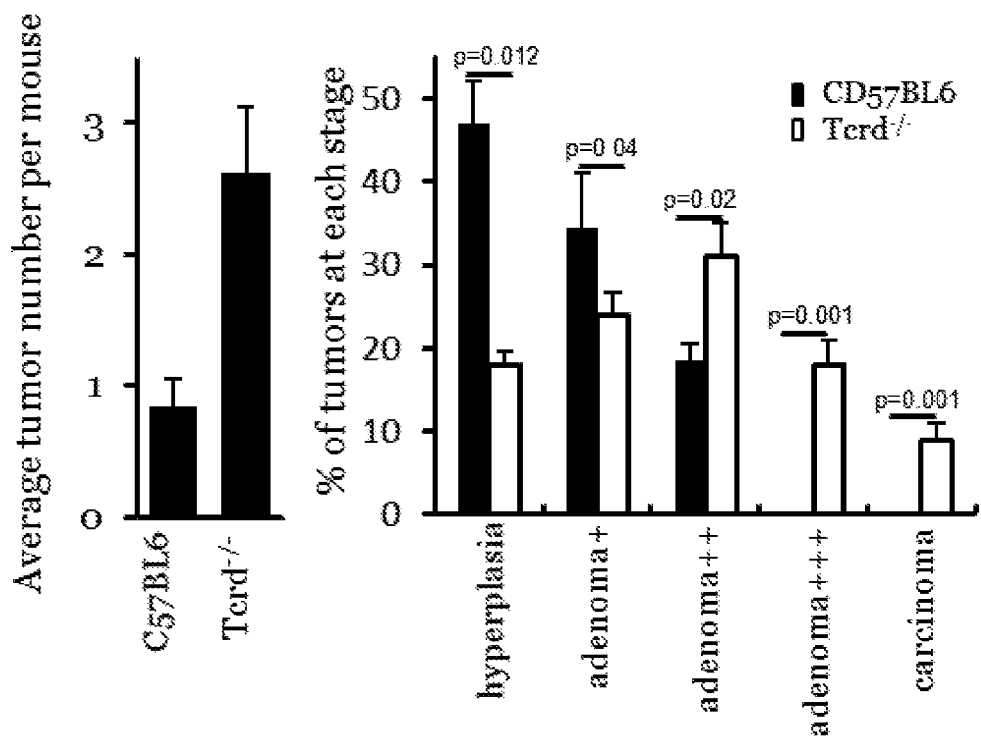
Figure 2I:
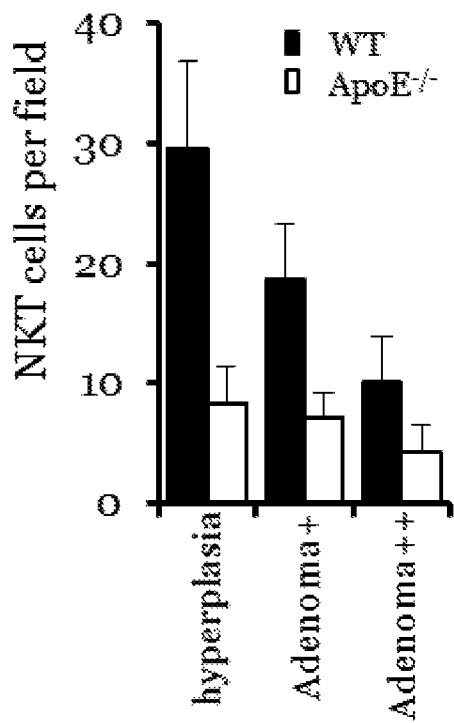
Figure 2J:
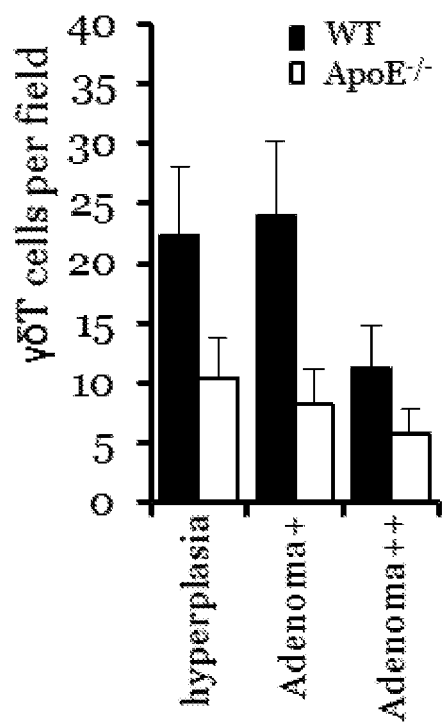
Figure 3H:
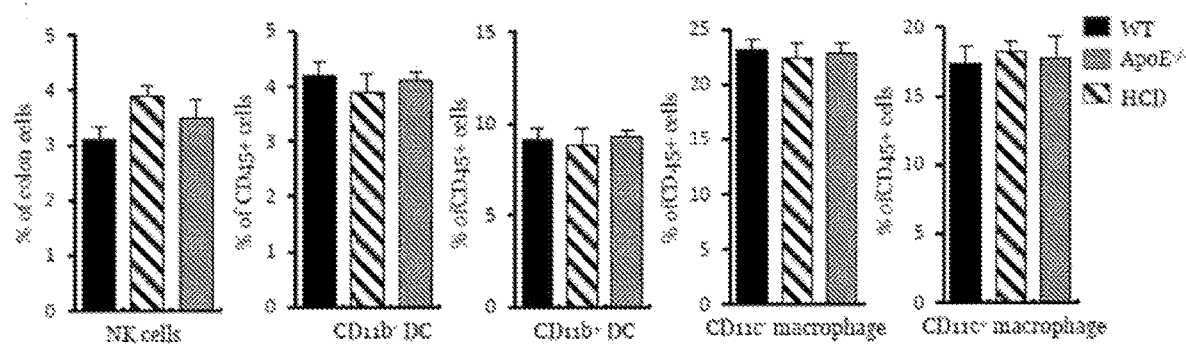

Example 4. NKT and γδT Cells are Critical Components of Immunosurveillance Against Colorectal Cancer Induced by AOM NKT cells and γδT cells that reside in the gut mucosa and submucosa are pivotal components of the gut-associated innate immune system. Consistent with the reduction of NKT and γδ T cell maturation in the thymus, we found a substantial 6-fold decrease in NKT cells and a 3-fold decrease in γδ T cells in the submucosa of the colon of ApoE$^{-/-}$ mice (FIGS. 2E, F). Meanwhile, the other major cellular components of cancer immunosurveillance, including NK cells, CD11b$^-$ dendritic cells, CD11b$^+$ dendritic cells, CD11c macrophages and CD11c$^+$ macrophages in the colon of hypercholesterolemic mice, did not show significant changes (FIG. 3H). To confirm that this substantial reduction of NKT and γδT cells impairs tumor immunosurveillance, we determined the incidence of AOM-induced colorectal cancer in Tcrd$^{-/-}$ mice, which lack γδT cells, and CD1d$^{-/-}$ mice, which lack NKT cells. Both mouse strains showed a significantly higher incidence and greater histopathologic severity of colorectal cancer than their control strains (FIGS. 2G, H). In addition, we also found significantly fewer NKT and γδT cells infiltrated into the early but not later stages of tumor progression from hypercholesterolemic mice than in those from WT mice (FIGS. 2I, J) Together, these results indicate that hypercholesterolemia reduces the differentiation of HSCs towards NKT and γδT cells, and thereby impairs tumor immunosurveillance against colorectal cancer.

Figure 4A:
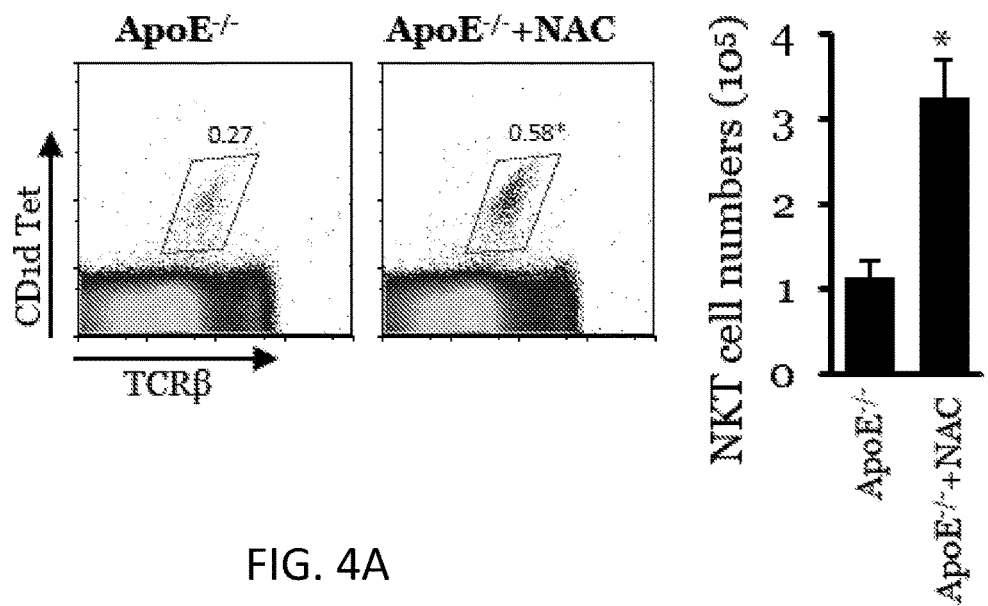
Figure 4B:
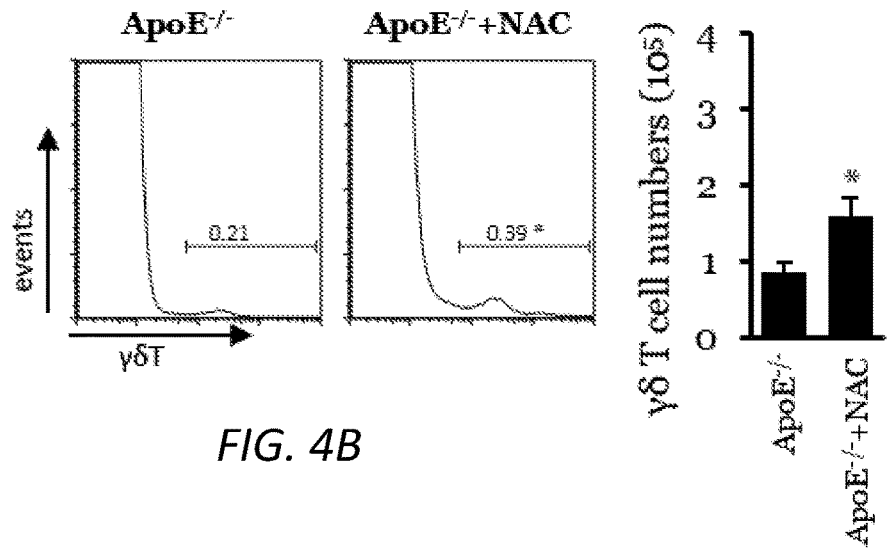
Figure 4C:
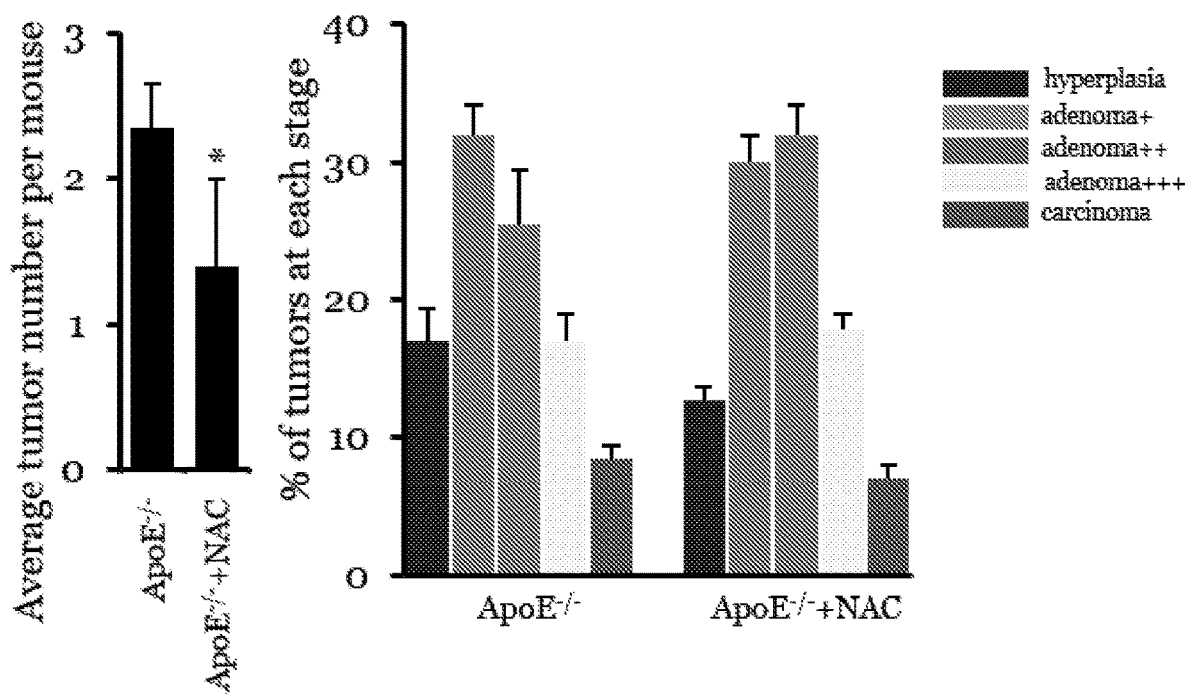
Figure 4D:
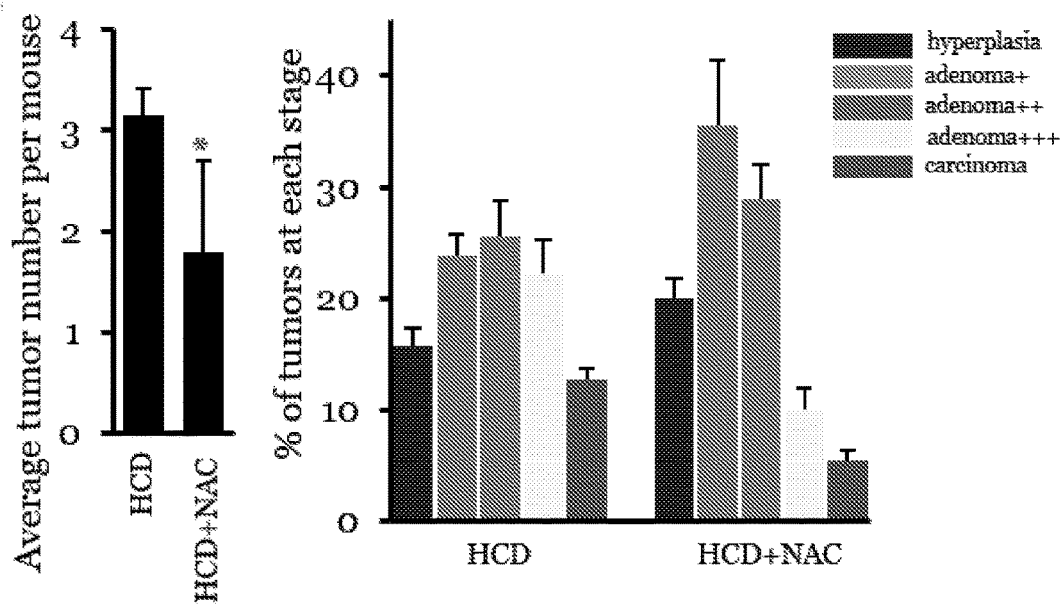
Figure 4E:
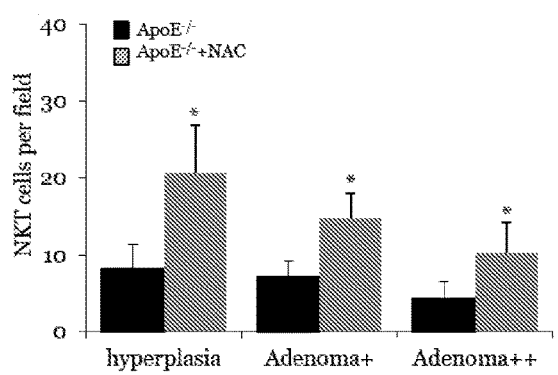
Figure 4F:
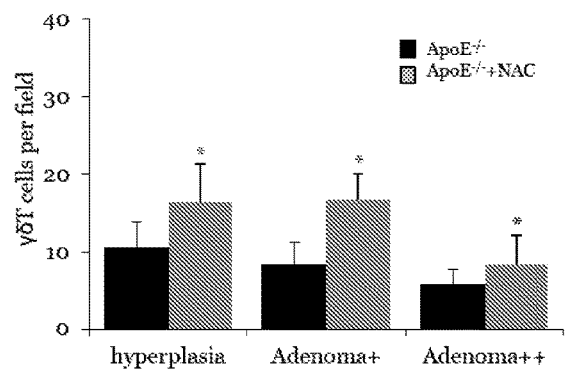

Example 5. The Incidence of Colorectal Cancer is a Linear Function of Hypercholesterolemia-Induced HSC Oxidant Stress We previously showed that hypercholesterolemia induces an oxLDL dependent increase in oxidant stress in HSCs that accelerated their ageing and impaired their repopulation capacity, both of which were reversed by the antioxidant N-acetylcysteine (NAC) (Tie G. et al. 2014). Interestingly, NAC administration rescued the otherwise impaired differentiation of HSCs toward NKT and γδ T cells in hypercholesterolemic mice (FIGS. 4A, B). NAC also significantly decreased the average tumor number in ApoE$^{-/-}$ and HCD mice. While NAC reduced significantly the histopathologic severity of tumors in HCD mice, the reduction in the histopathologic severity of tumors in ApoE$^{-/-}$ mice did not reach statistical significance (FIGS. 4C, D). Finally, NAC increased significantly the infiltration of NKT and γδ T cells in early stages of tumor development in both ApoE$^{-/-}$ and HCD mice (FIGS. 4E,F). Regression analysis between the degree of HSC oxidant stress and the number of tumors per mouse revealed a remarkable linear correlation between these variables ($R^2$=0.87) (FIG. 4G). Together, these findings show that hypercholesterolemia-induced HSC oxidant stress directly mediates the reduction of HSC differentiation toward NKT and γδ T cells and the consequent increase in tumor number and histopathologic severity.

Figures 5H, 5I:
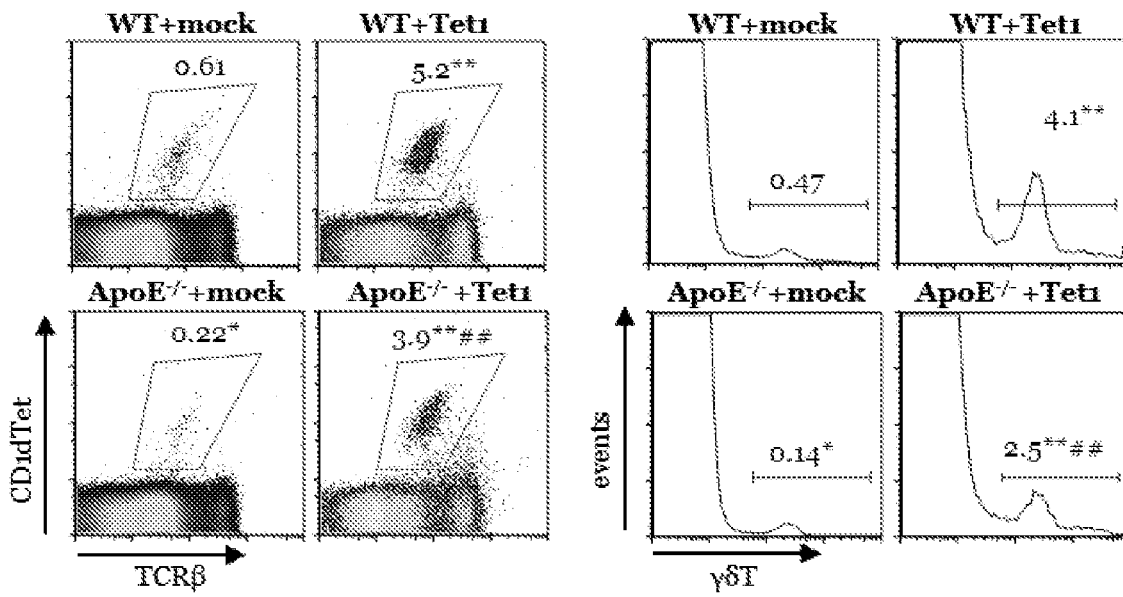

Example 6. Hypercholesterolemia-Induced Downregulation of Tet1 in HSCs Impairs their Differentiation Towards NKT and γδT Cells The cell autonomous defect in HSC differentiation caused by hypercholesterolemia-induced oxidant stress raised the possibility that oxidant stress disrupted an epigenetic regulatory pathway necessary for proper HSC differentiation to NKT and γδT cells. To test this possibility, we first assessed whether the expression levels of major epigenetic regulatory factors were altered in hypercholesterolemic mice. We observed an oxidant stress-dependent reduction in the expression of Tet1 in HSCs from hypercholesterolemic mice (FIGS. 5A, B).

The Tet family, includes Tet1, Tet2 and Tet3 which demethylate genomic DNA (Ito, S. et al. 2010; Ko, M. et al. 2010; Ito, S. et al. 2011). Within the Tet family, Tet2 has been shown to have a critical role in regulating the self-renewal, proliferation and differentiation of HSCs (Ko, M. et al. 2010; Ko, M. et al. 2011), whereas the role of Tet1 in HSC differentiation is as yet unknown. In our experiments, we found an oxidant stress-dependent downregulation of Tet1 in HSCs from hypercholesterolemic mice (FIG. 5A, B).

Figure 6A:
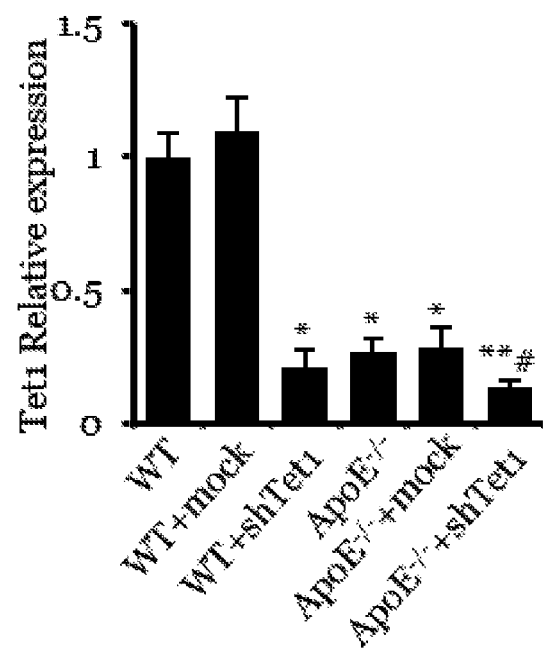
FIGS. 6A-L. The expression of Tet1 determines the differentiation of HSCs towards NKT and γδT cells in vitro. A, Downregulation of Tet1 by shRNA in HSCs. n=6, *, p<0.05; **, p<0.01, vs. WT; #, p<0.05, vs. ApoE$^{-/-}$. B, Differentiation of HSCs towards NKT cells in vitro following Tet1 downregulation C, Differentiation of HSCs towards γδT cells in vitro following Tet1 downregulation. n=6, *, p<0.05; **, p<0.01, vs. WT; #, p<0.05, vs. ApoE$^{-/-}$. D, Differentiation of HSCs towards NKT cells in vitro following Tet1 overexpression. E, Differentiation of HSCs towards γδT cells in vitro following Tet1 overexpression. n=6, *, p<0.05; **, p<0.01, vs. WT; #, p<0.05, vs. ApoE$^{-/-}$. F, CCR6+ cells in γδT cells derived from WT and Tet1$^{-/-}$ thymus. G, IL-17V population in γδT cells derived from WT and Tet1$^{-/-}$ thymus. n=5, *, p<0.05, vs. WT+mock. H, CCR6+ population in γδT cells derived from recipient mice; I, IL-17$^+$ cells in γδT cells derived from recipient mice. n=8, *, p<0.05, vs. WT+mock; #, p<0.05, vs. ApoE$^{-/-}$+mock. J, DN1 (CD44CD25 DN), DN2 (CD44'CD2S'DN) and DN3 (CD44$^-$CD25$^+$DN) populations in thymus of recipient mice transplanted with WT HSCs or Tet1 overexpressing WT HSCs. n=6, *, p<0.05, vs. WT+mock. K, DP (CD4$^+$CD8$^+$), DN (CD4$^-$CD8$^-$), CD4$^+$ and CD8$^+$ populations in thymus of recipient mice transplanted with WT HSCs or Tet1 overexpressing WT HSCs. n=6, *, p<0.05, vs. WT. L, Frequency of B cells, NK cells, CD3e$^+$, CD4$^+$ and CD8$^+$ cells in peripheral blood of recipient mice transplanted with WT HSCs or Tet1 overexpressing WT HSCs. n=6, *, p<0.05, vs. WT.
Figure 6B:
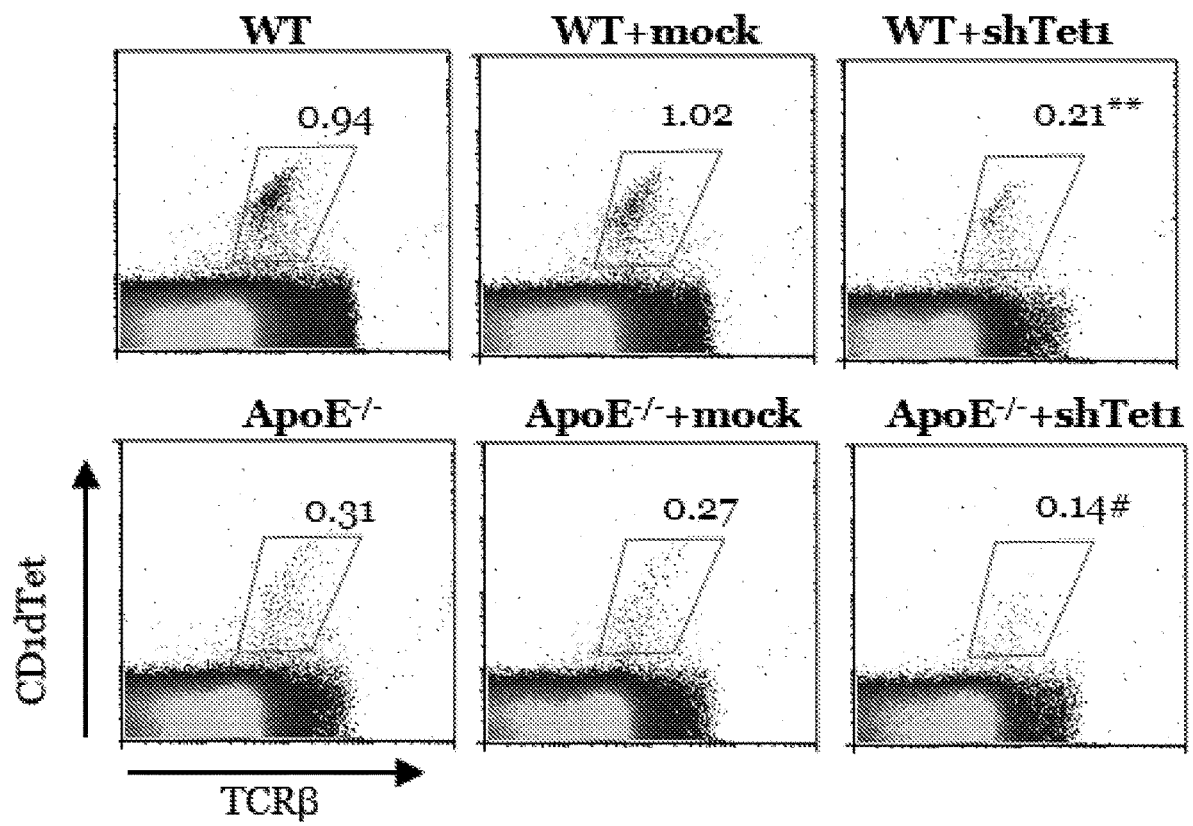
Figure 6C:
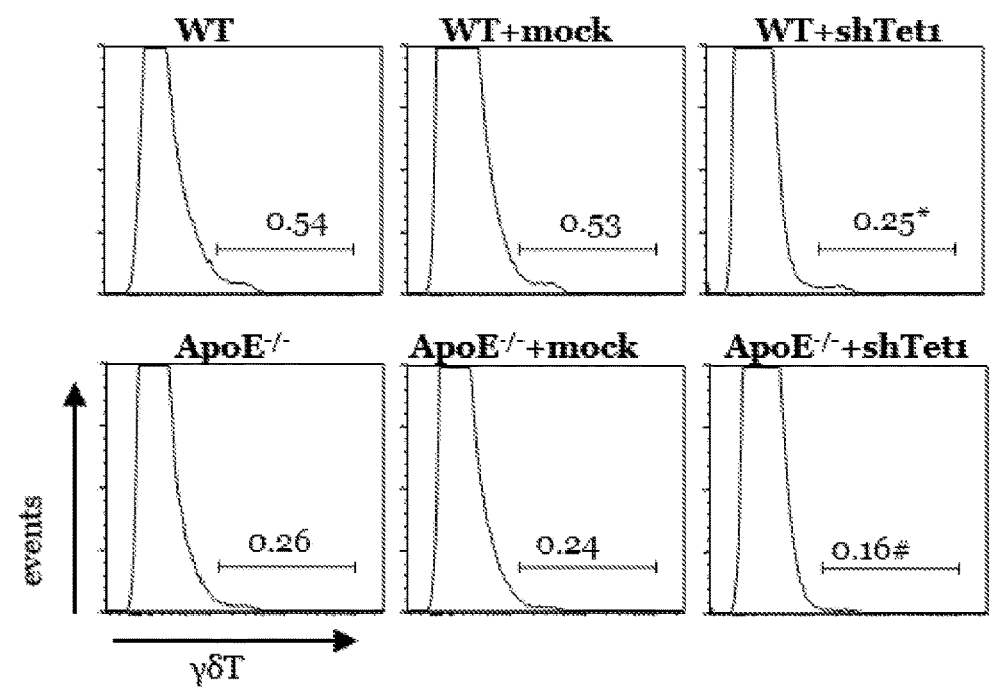
Figure 6D:
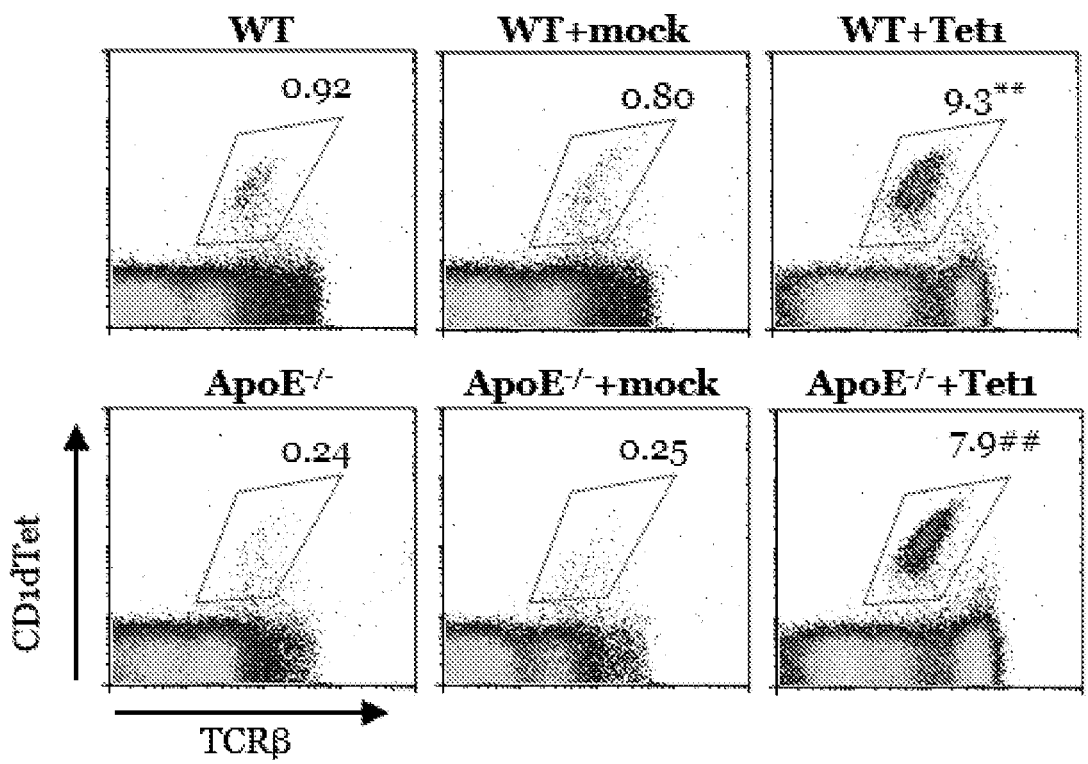
Figure 6E:
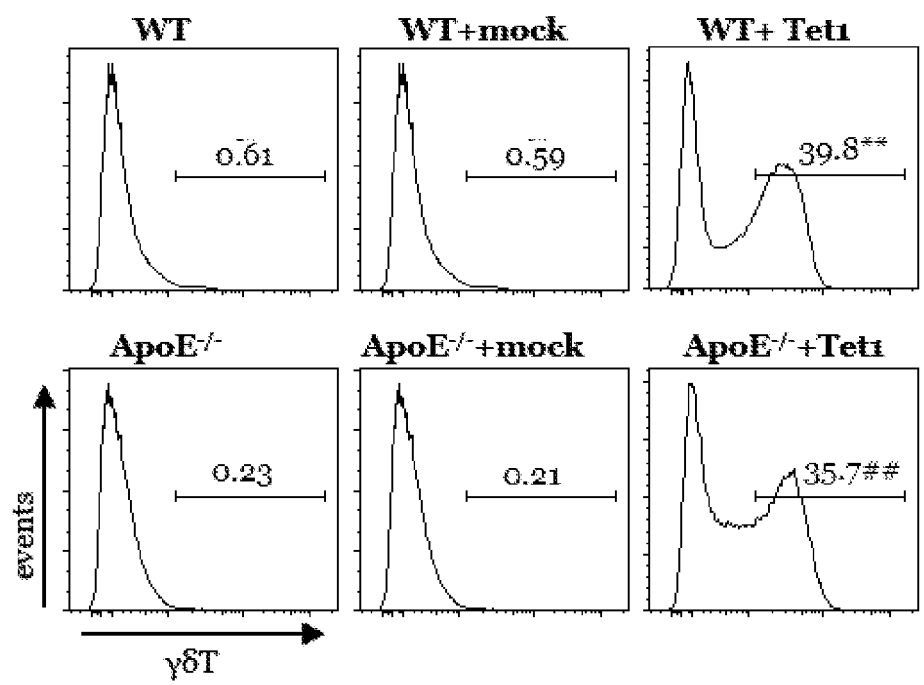
Figure 13A:
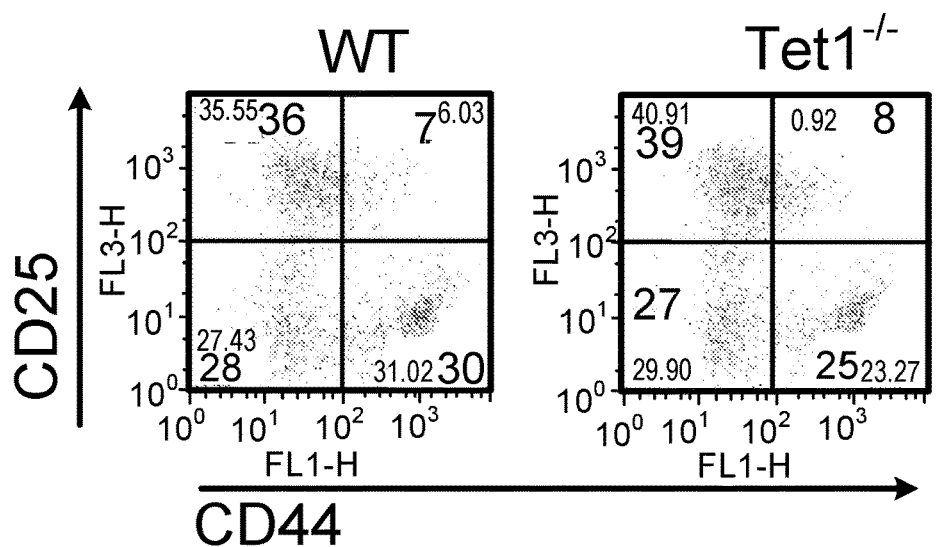
FIGS. 13A-D. The frequency of T cell intermediate populations in thymus, the cellular components related to cancer immunosurveillance in peripheral blood and colon of WT and Tet$^{-/-}$ mice. A, DN1 (CD44$^+$CD25$^-$DN), DN2 (CD44$^+$CD25$^+$DN), and DN3 (CD44$^-$CD25$^+$DN) populations in thymus of WT and Tet1$^{-/-}$. n=6, *, p<0.05, vs. WT. B, DP (CD4$^+$CD8$^+$), DN (CD4$^-$CD8$^-$), CD4$^+$ and CD8$^+$ populations in thymus of WT and Tet1$^{-/-}$ mice. n=6, *, p<0.05, vs. WT. C, Frequency of B cells, NK cells, CD3e$^+$, CD4$^+$ and CD8$^+$ cells in peripheral blood of WT and Tet1$^{-/-}$ mice. n=6, * p<0.05, vs. WT. D, NK cells (CD45$^+$CD3e$^-$NKp46$^+$), CD11b$^-$ dendritic cells (CD11c$^+$CD11b$^-$CD103$^+$F4/80$^-$), CD11b$^+$ dendritic cells (CD11c$^+$CD11b$^+$CD103$^+$F4/80$^-$), CD11c$^-$ macrophages (CD11c-CD11b$^+$CD103$^-$F4/80$^+$) and CD11c$^+$ macrophages (CD11c$^+$CD11b$^+$CD103$^-$F4/80$^+$) in the colon of WT and Tet1$^{-/-}$ mice. n=6, *, p<0.05, vs. WT.
Figure 13B:
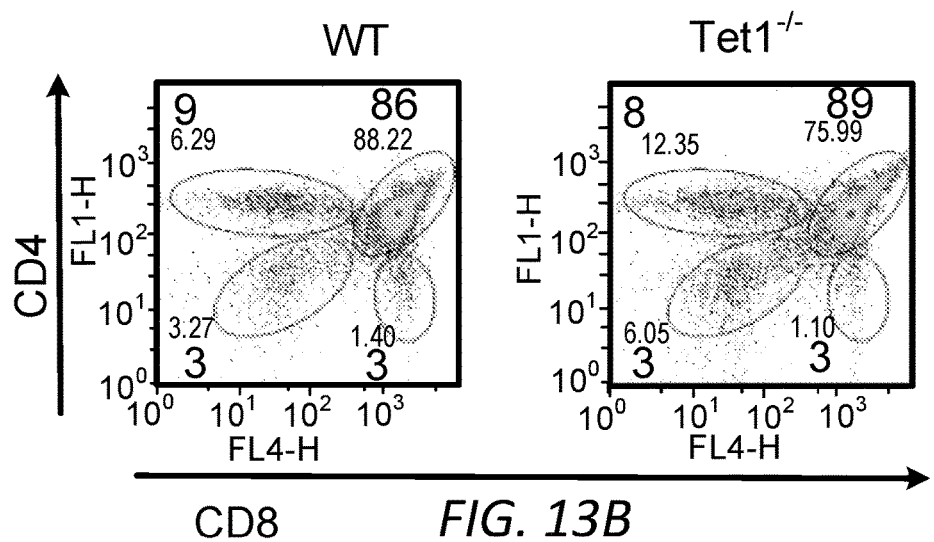
Figure 13C:
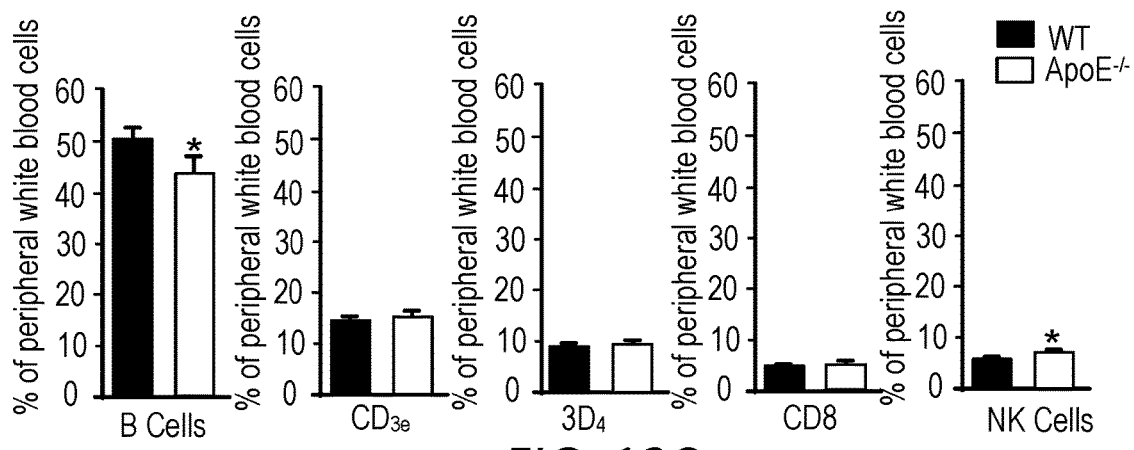
Figure 13D:
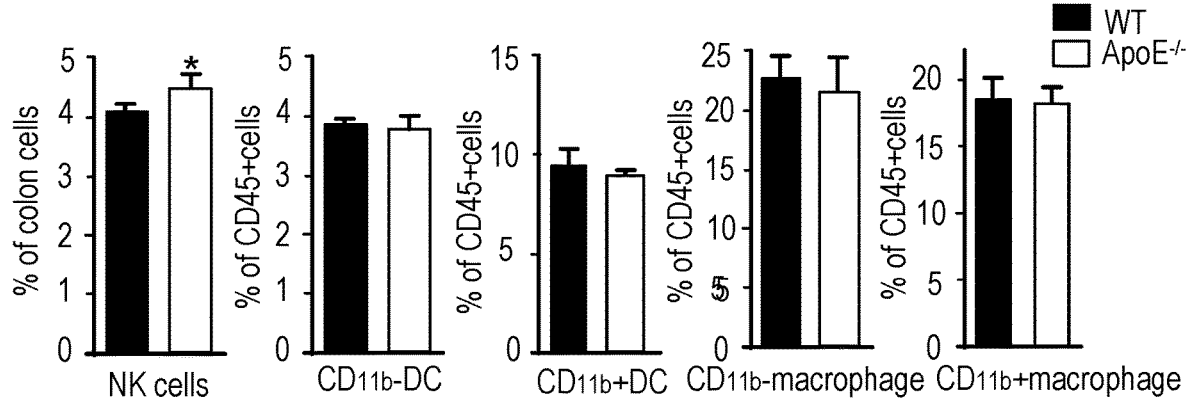
Figure 14A:
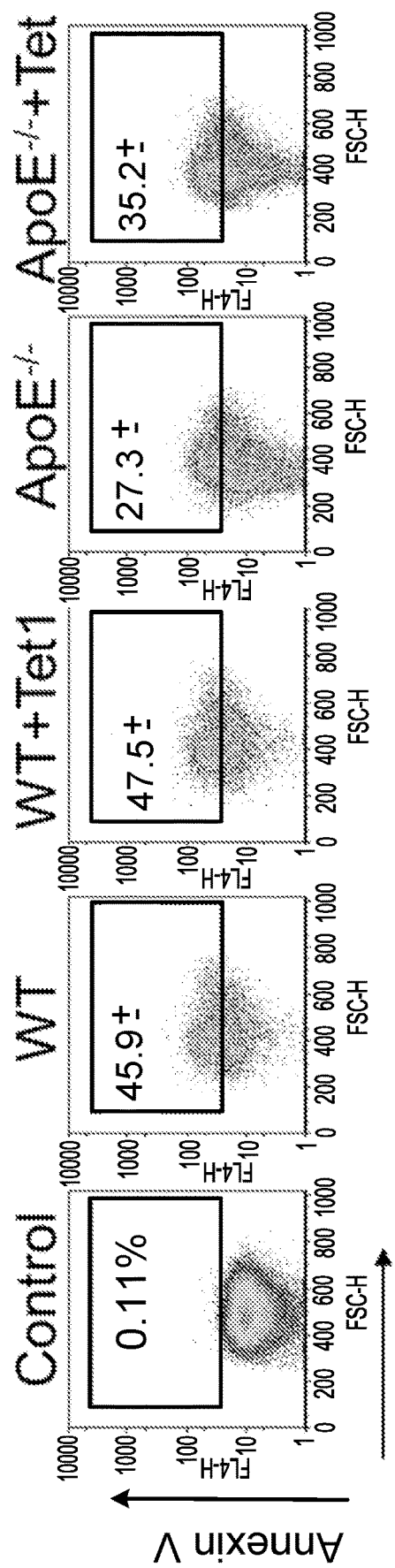
FIGS. 14A-B. NKT mediated cytotoxicity. A, FACS plots of annexin V staining of C57BL6 murine colon adenocarcinoma MC38 cells that had been co-cultured with WT NKT cells, WT NKT cells overexpressing Tet1, ApoE$^{-/-}$ NKT cells or ApoE$^{-/-}$ NKT cells overexpressing Tet1 for 24 hours. B, Bar graph showing percentage of apoptotic MC38 cells that were cultured under the same experimental conditions as in A. *, p<0.05 FIGS. 14 C-D. γδT cell mediated cytotoxicity. C, FACS plots of annexin V staining of C57BL6 murine colon adenocarcinoma MC38 cells that had been co-cultured with WT γδT cells, WT NKT cells overexpressing Tet1, ApoE$^{-/-}$ γδT cells or ApoE$^{-/-}$ γδT cells overexpressing Tet1 for 24 hours. D, Bar graph showing percentage of apoptotic MC38 cells that were cultured under the same experimental conditions as in C. *, p<0.05
Figure 14B:
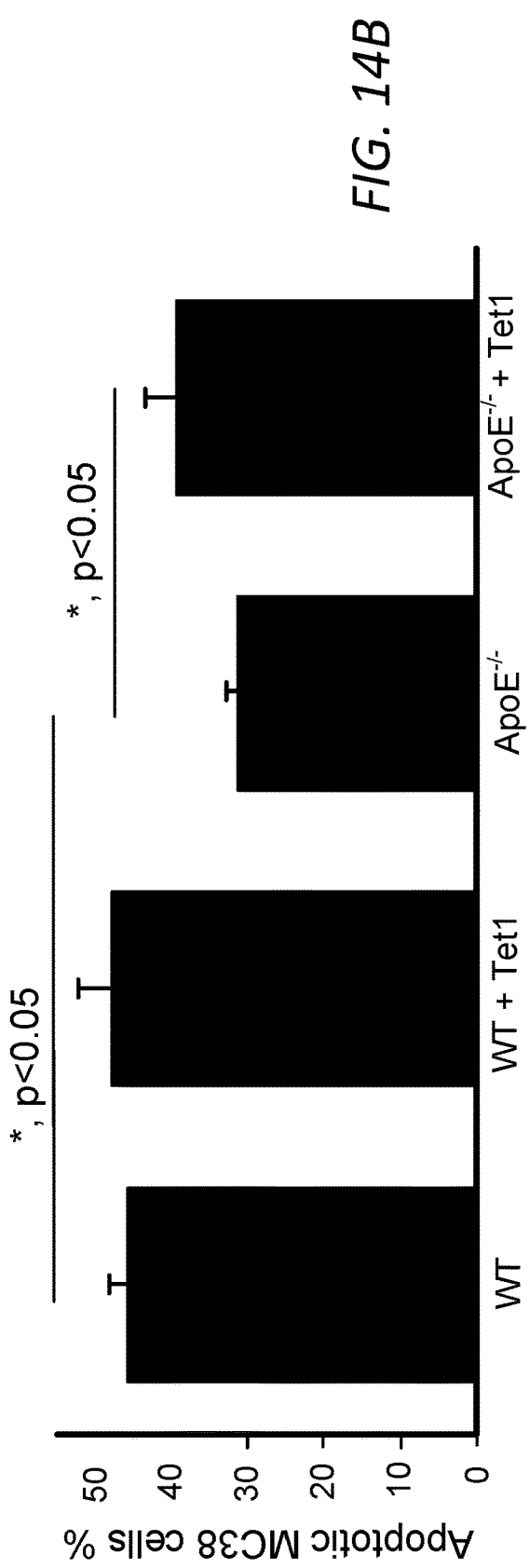
Figure 14C:
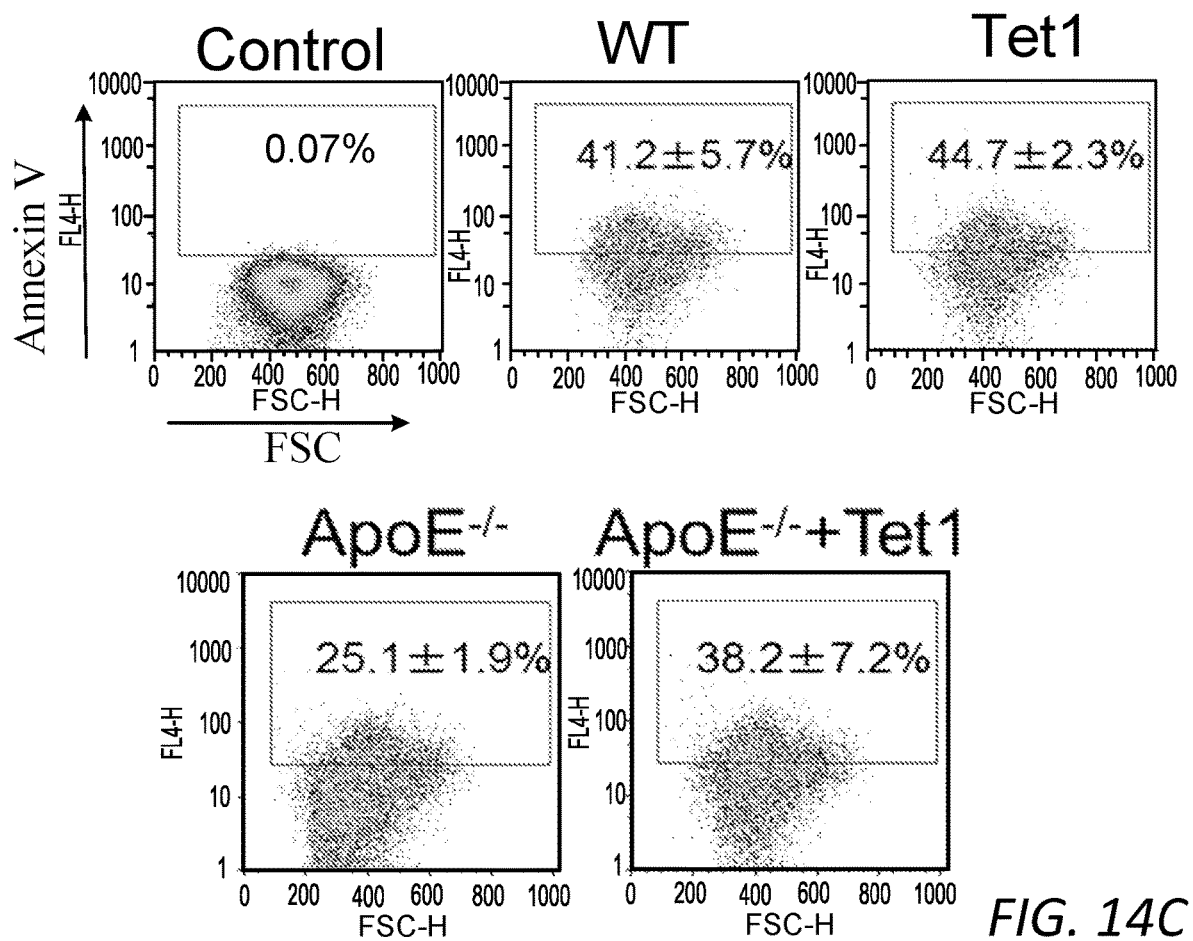
Figure 14D:
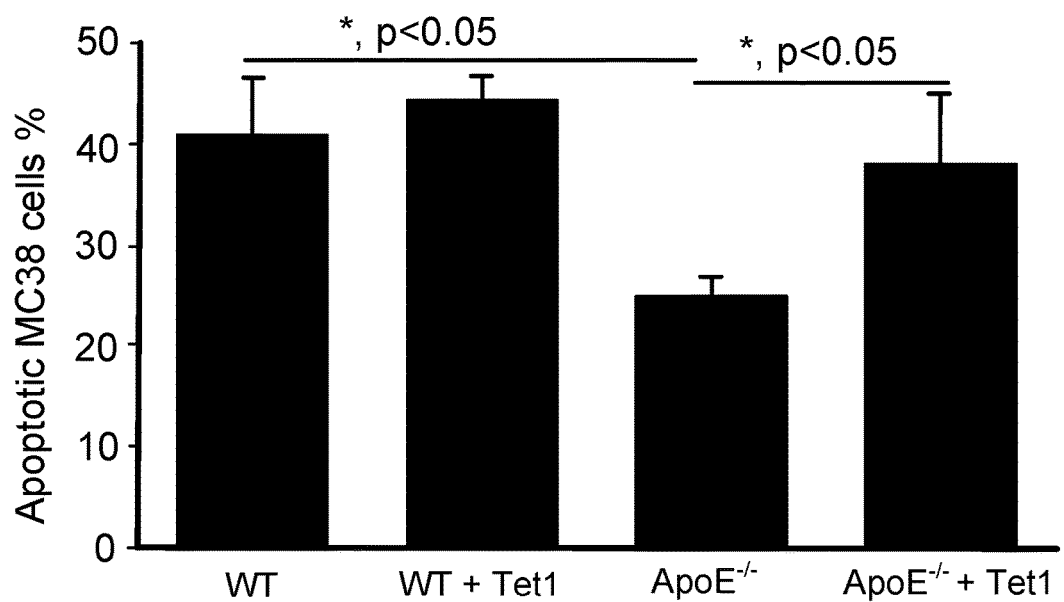

In order to determine if this reduction of Tet1 expression is directly responsible for the decrease in NKT and γδT cells and the impairment of tumor immunosurveillance in hypercholesterolemic mice, we measured the percentage and total number of NKT and γδT cells in the thymus of WT and Tet1$^{-/-}$ mice. Consistent with our findings in hypercholesterolemic mice, the percentage and total number of NKT and γδT cells in the thymus was significantly lower in Tet1$^{-/-}$ mice than WT mice (FIGS. 5C, D). Similar to the decrease in total thymocytes in Tet1$^{-/-}$ mice, the percentage and number of NKT and γδT cells was also decreased in the colon submucosa of Tet1$^{-/-}$ mice (FIGS. 5E, F). Meanwhile, Tet1$^{-/-}$ mice did not show significant changes in T cell intermediate populations in the thymus (FIG. 13A, B), similar to that seen in hypercholesterolemic mice. With the exception of a slight increase in NK cells and a slight decrease in B cells, we did not find significant changes in CD3e$^+$, CD4$^+$ and CD8$^+$ cells in peripheral blood of Tet1$^{-/-}$ mice (FIG. 13C). The other major cellular components of cancer immunosurveillance, including NK cells, CD11b$^-$ dendritic cells, CD11b$^+$ dendritic cells, CD11c$^-$ macrophages and CD11c$^+$ macrophages did not show significant changes in the colon of Tet1$^{-/-}$ mice (FIG. 13D). In an in vitro HSC differentiation assay, knockdown of Tet1 expression in HSCs from either WT or ApoE$^{-/-}$ mice greatly reduced their differentiation towards NKT and γδT cells (FIGS. 6A-C).

Figure 6F:
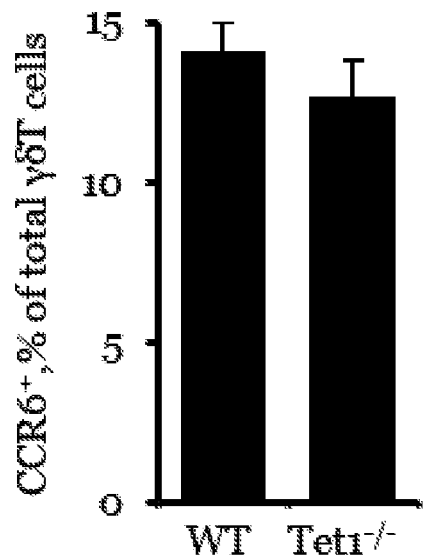
Figure 6G:
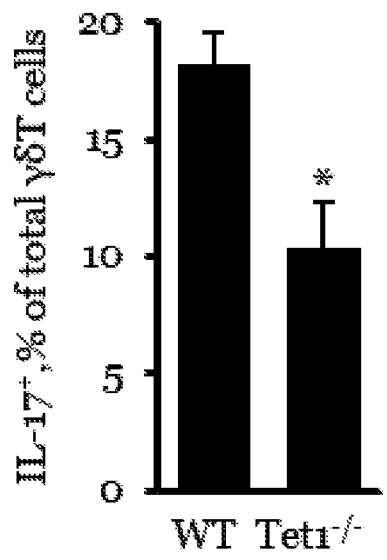
Figure 6H:
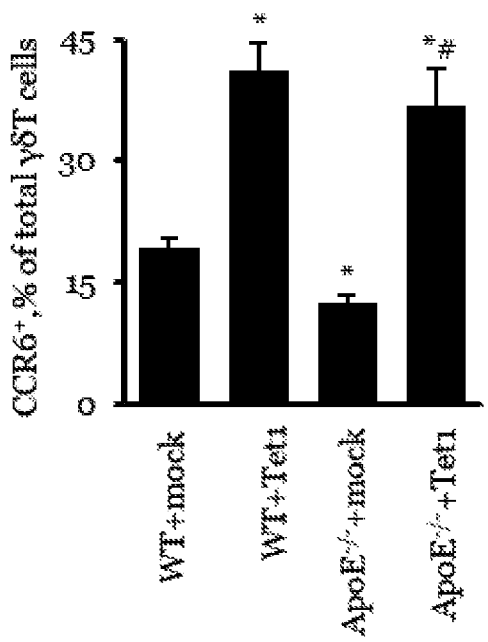
Figure 6I:
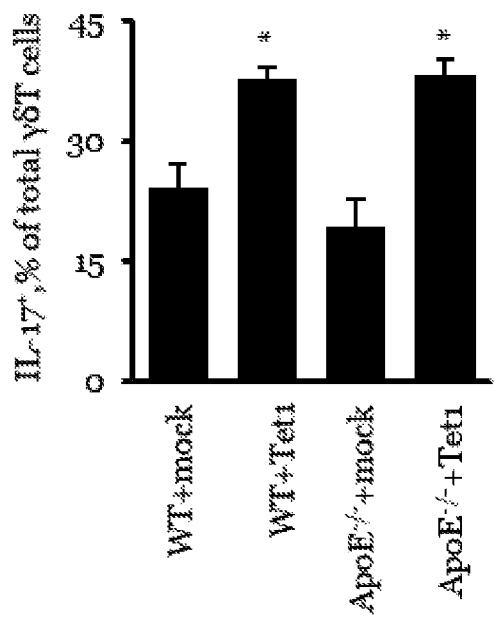
Figure 6J:
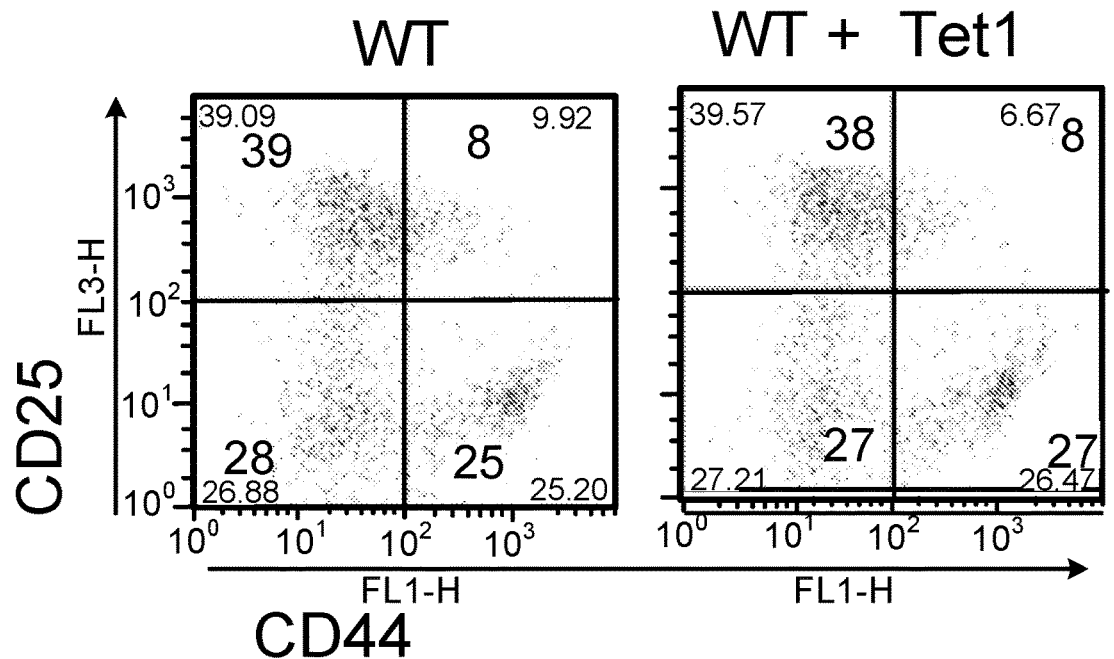
Figure 6K:
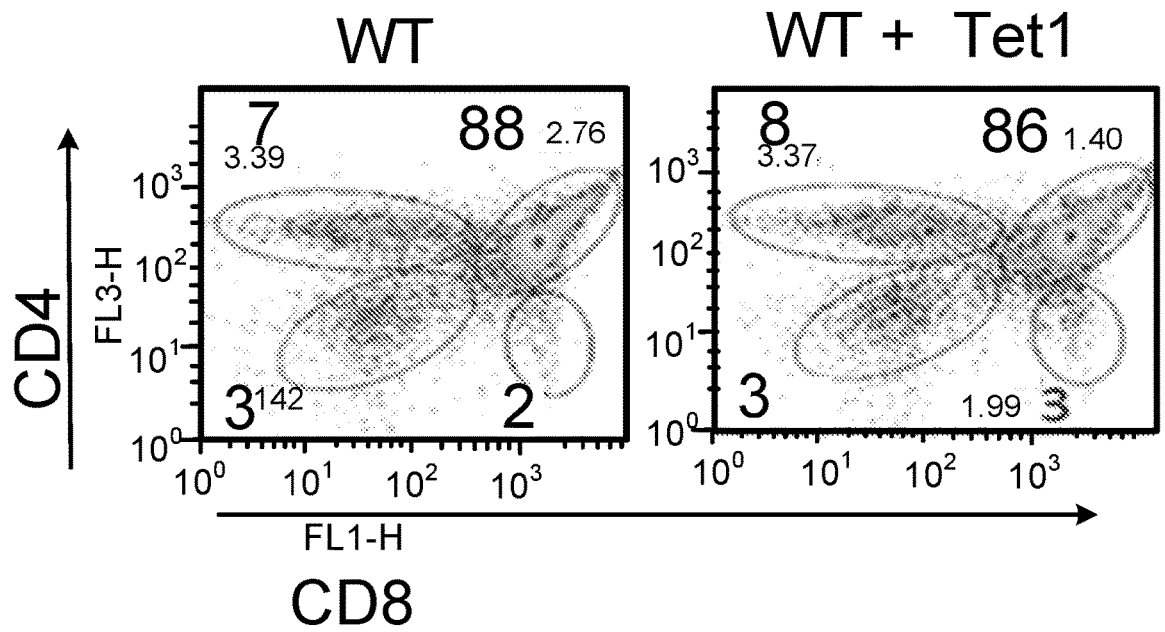
Figure 6L:
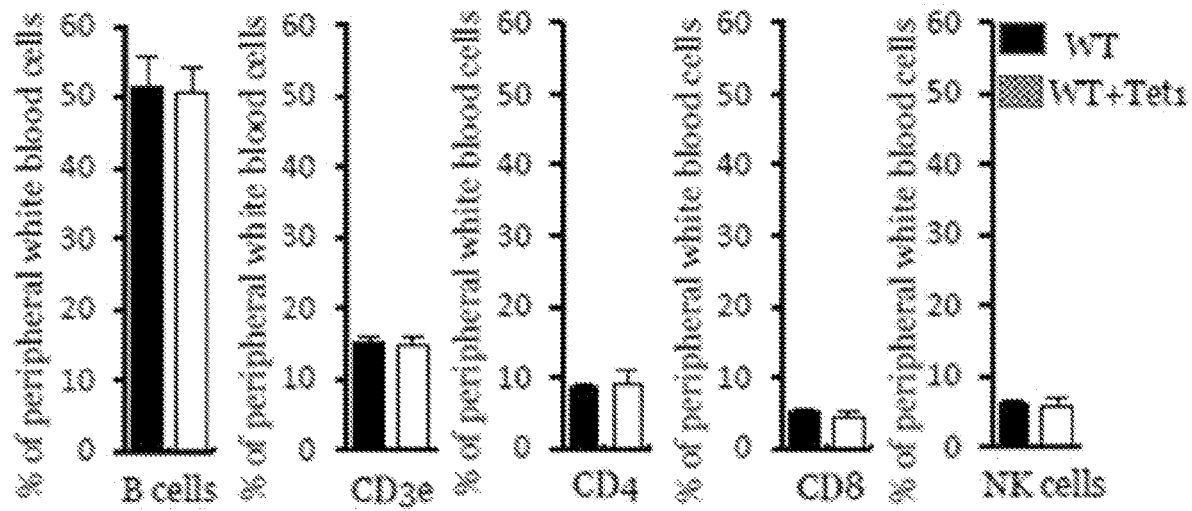

In that same in vitro HSC differentiation assay, the overexpression of Tet1 in HSCs from WT or ApoE$^{-/-}$ mice caused a 7-fold increase in WT and almost 20-fold increase in ApoE$^{-/-}$ mice in HSC differentiation towards NKT cells both in vitro and in vivo. The overexpression of Tet1 in HSCs also caused a 10-fold increase in WT and 20-fold increase in ApoE$^{-/-}$ mice in HSC differentiation towards γδT cells (FIGS. 5G-I; FIGS. 6A, D, E). The overexpression of Tet1 in HSCs did not affect the daughter T cell intermediate populations in thymus as well as B cells, NK cells, CD3e+, CD4+ and CD8+ cells in peripheral blood of recipient mice (FIGS. 6J, K, L). These results further support the role of Tet1 in HSCs lineage specification towards NKT and γδT cells.

In addition to Tet1's effect on HSC differentiation towards NKT and γδT cells, we sought to determine whether Tet1 was also necessary for the function of terminally differentiated NKT and γδT cells. IL-17 is a critical cytokine in both innate and adaptive immunity. IL-17 has numerous roles including activation of signaling cascades that recruit immune cells and neutrophils to the site of the tumor. CCR6 regulates the migration and recruitment of T cells during inflammatory and immunological responses (Corpuz, T M. Et al. 2016; Shibata, S. et al. 2015: Wilson, R P et al 2015; Zarin, P. et al. 2015). γδT cells from ApoE$^{-/-}$ mice also showed significant decreases in the production of IL-17 (FIGS. 6F, G). Interestingly, γδT cells derived from Tet1 overexpressing HSCs also displayed greater expression of CCR6 and IL-17 than WT mice (FIGS. 6H, I). These increases in IL-17 γδT cells and CCR6 γδT cells predicted the results of the effects of Tet1 overexpression on cytotoxicity. Overexpression of Tet1 in ApoE$^{-/-}$ HSCs restored there cytotoxicity to WT levels (14A-D) These changes support the critical role of Tet1 in the reduction in tumor number as well as their histopathologic severity in hypercholesterolemic mice. These results also indicate that Tet1 expression in HSCs is a pivotal determinant not only of the lineage specification of HSCs towards NKT and γδT cells but also of the function of terminally differentiated NKT and γδT cells.

Figure 7A:
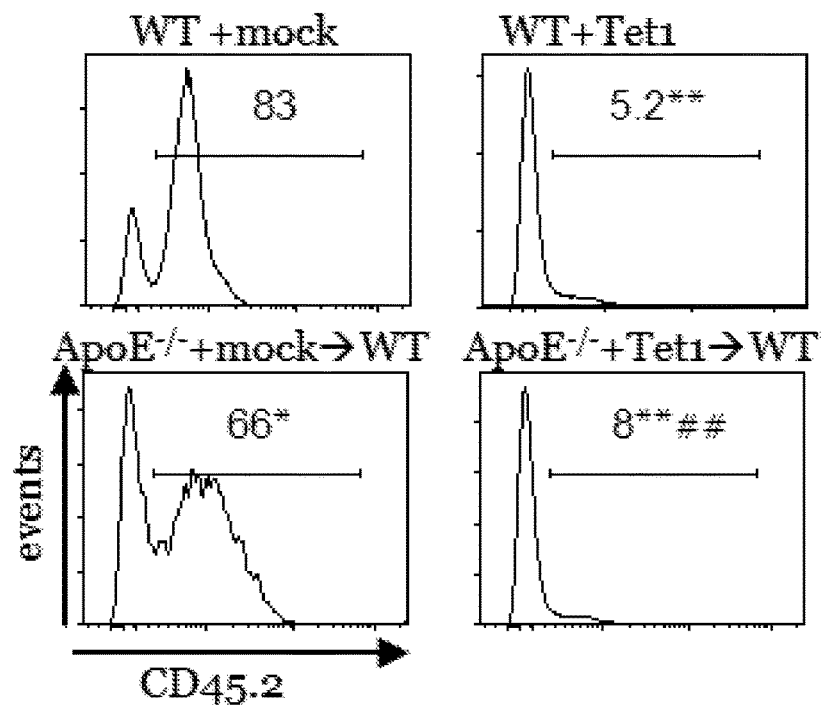
Figure 7B:
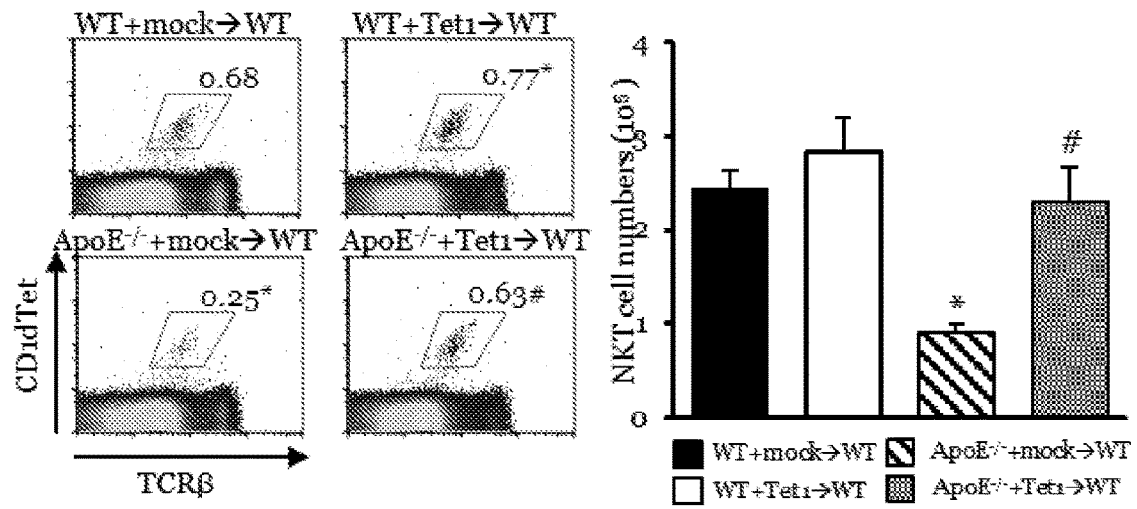
Figure 7C:
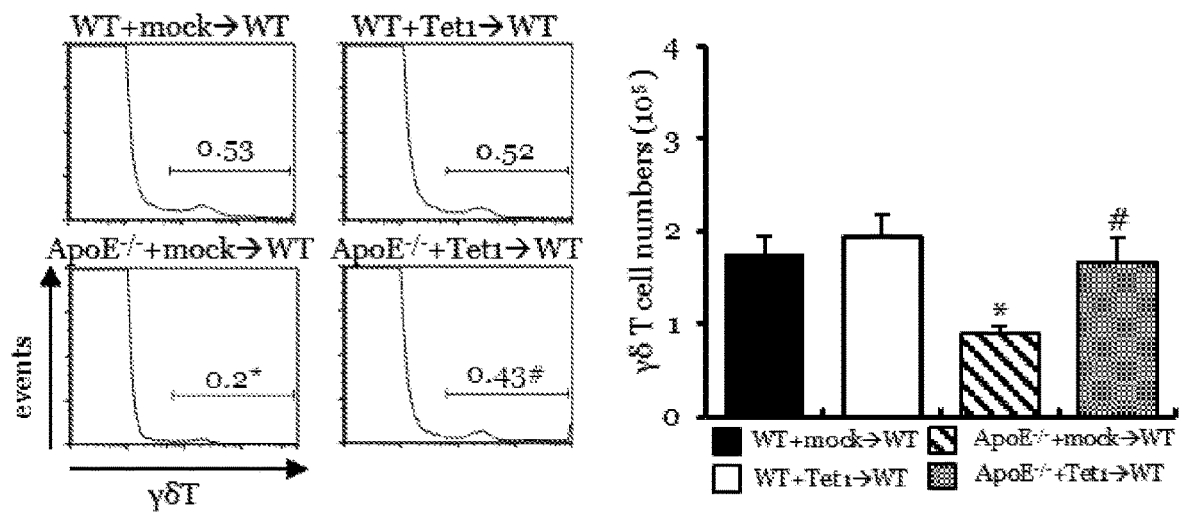
Figure 7F:
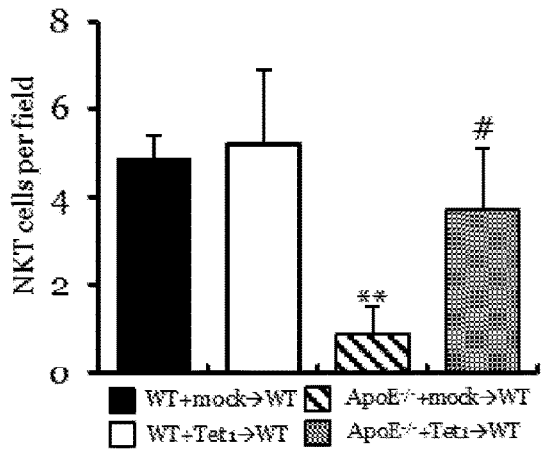
Figure 7F:
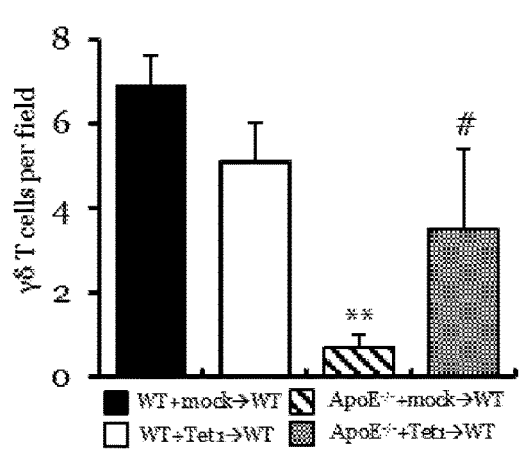
Figure 7F:
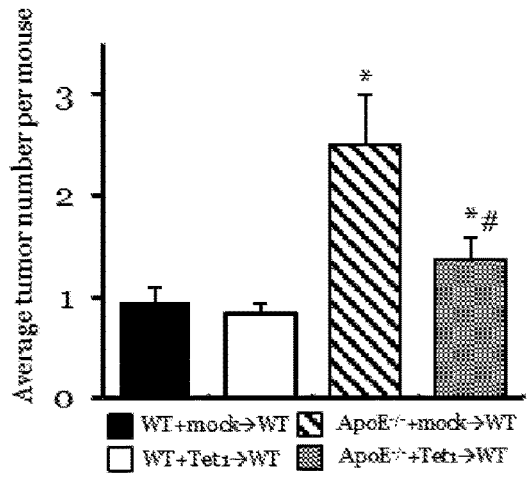
Figure 7G:
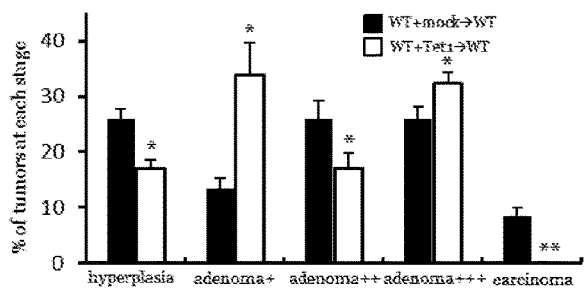
Figure 7G:
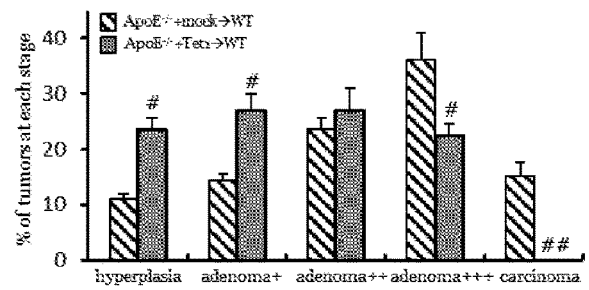

We next sought to determine in vivo whether the overexpression of Tet1 in HSCs from hypercholesterolemic mice could restore their normal lineage specification towards NKT and γδT cells and thereby immunosurveillance against colorectal cancer. We reconstituted hematopoiesis of lethally irradiated WT recipient mice with WT HSCs, Tet1-overexpressing WT HSCs or Tet1-overexpressing ApoE$^{-/-}$ HSCs. When we tried to reconstitute WT and ApoE$^{-/-}$ mice with HSCs that overexpress Tet1, all the mice died. We assumed these deaths were secondary to failed reconstitution of hematopoiesis in the bone marrow of the irradiated mice. To address this problem, the transplantation of Tet1 overexpressing WT HSCs was supported with normal, non-transduced WT HSCs and similarly the transplantation of Tet1 overexpressing ApoE$^{-/-}$ HSCs was supported with ApoE$^{-/-}$ HSCs, both at the ratio of 3:1 (FIG. 7A). Our assumption proved correct. Under these conditions all mice survived and overexpression of Tet1 in ApoE$^{-/-}$ HSCs restored the number of NKT and γδT cells in the thymus of recipient WT mice to that of recipient WT mice reconstituted with WT HSCs (FIGS. 7B, C). In a similar manner, overexpression of Tet1 in ApoE$^{-/-}$ HSCs restored the number of submucosal NKT and γδT cells in recipient irradiated WT mice (FIGS. 7D, E). Most significantly, overexpression of Tet1 in ApoE$^{-/-}$ HSCs reduced the average tumor number of colorectal cancer in recipient WT to a level similar to that of overexpressing of Tet1 in WT mice (FIGS. 7F, G). Moreover, overexpression of Tet1 in both ApoE$^{-/-}$ and WT HSCs had a profound effect on the histopathologic severity of the tumors. Indeed, lethally irradiated WT recipient mice reconstituted with either Tet1-overexpressing WT HSCs or Tet1-overexpressing ApoE$^{-/-}$ HSCs eliminated the progression of any tumors to the carcinoma stage in both groups (FIG. 7G). These results indicate that restoration of Tet1 expression in ApoE$^{-/-}$ HSCs rescues both their reduced lineage specification towards NKT and γδT cell populations and effective immunosurveillance against colorectal cancer. The increase in NKT and γδT cell populations in the mucosa and submucosa and the consequent reduction in the histopathologic severity of the AOM-induced tumors in WT mice transplanted with Tet1 overexpressing HSCs was an unexpected finding that might have potential immunotherapeutic implications.

Taken together, in mice with WT-HSCs that overexpressed Tet1, a number of salutary effects were noted that suggest that mi101C therapy is applicable to patients that do not have hypercholesterolemia. Reflecting their function, both the proportion of γδT cells' and the proportion of CCR6$^+$ were increased significantly with the mice that had HSCs that overexpressed Tet19 (14). Overexpression of Tet1 in WT HSCs also eliminated all tumors from progressing to carcinoma.

In the in vitro differentiation assay, overexpression of Tet1 in WT HSCs caused a 10 fold increase in the number of NKT cells versus the mock transduced WT cells. Overexpression of Tet1 in WT HSCs caused a 65 fold increase in the number of γδT cells versus mock transduced HSC. We also noted changes in gene expression that is consistent with these dramatic changes in cell number. Interestingly, several genes (ETV5, EGR2, SLAMF1, ZBTB16, and RELb) whose expression did not change significantly in ApoE$^{-/-}$ HSCs were also increased after overexpression of Tet1 in HSCs of both WT and ApoE$^{-/-}$ mice (FIG. 9C), suggesting that Tet1 overexpression to levels higher than those found in WT HSCs can increase the expression of genes required for NKT and γδ T specification. These are clinically significant findings because current human trials utilizing these cell types for cellular immunotherapy all suffer from inadequate cell number.

Figure 8E:
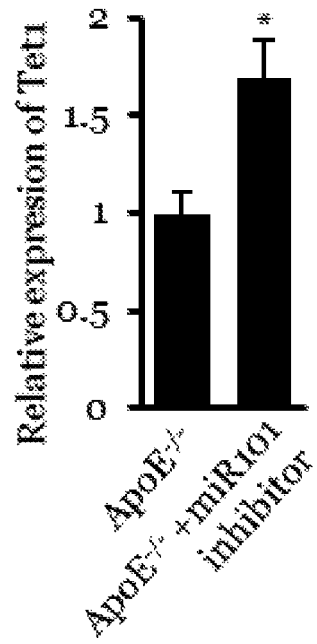
Figure 8F:
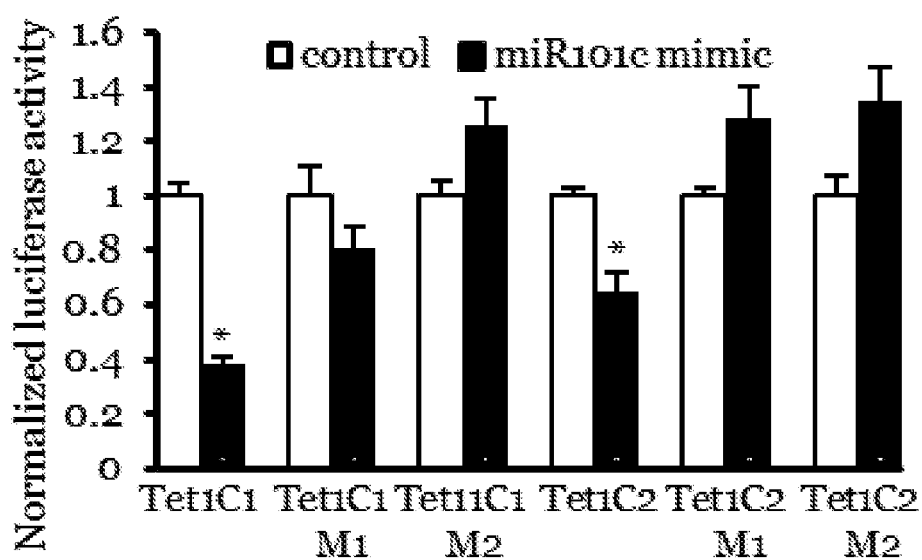
Figure 8G:
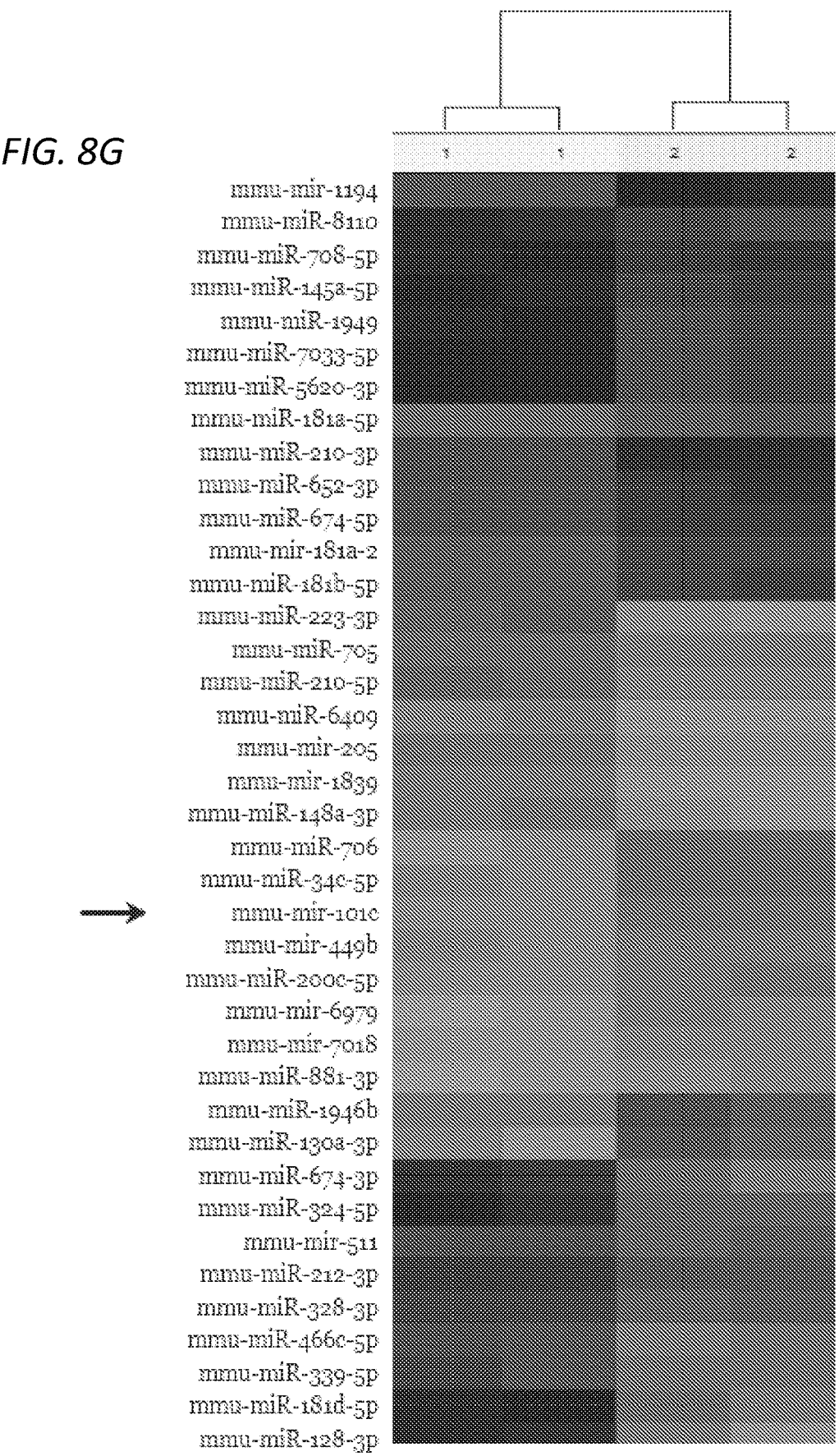
Figure 8H:
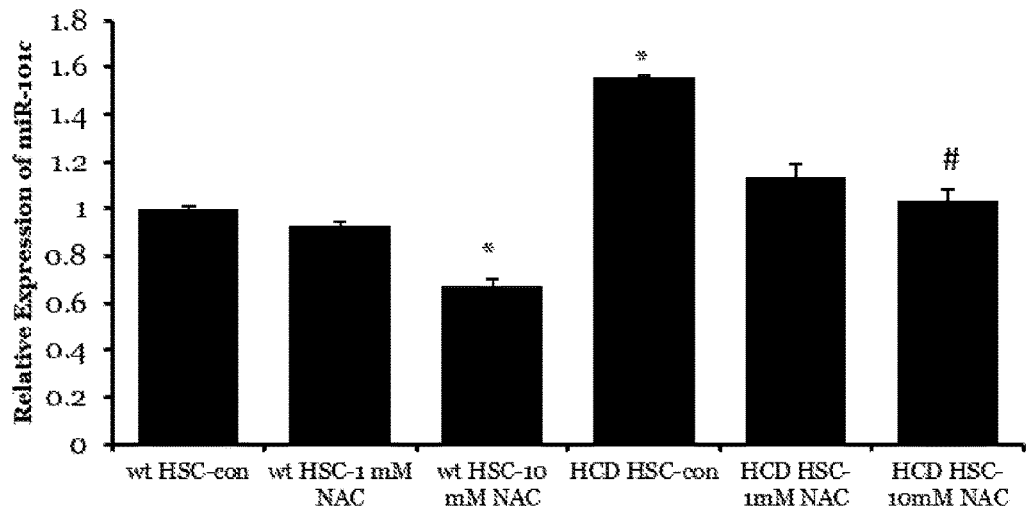

Example 7. miR101c Mediates the Downregulation of Tet1 in HSCs Isolated from Hypercholesterolemic Mice Besides DNA methylation and histone modification, microRNAs function as important components in epigenetic regulation. To identify microRNAs that are altered by hypercholesterolemia, we performed miRNA microarray analysis in HSCs isolated from WT and hypercholesterolemic ApoE$^{-/-}$ mice (FIG. 8G). Among them, miR101c, which is predicted to directly target Tet1, showed a significant upregulation in HSCs from ApoE$^{-/-}$ mice. This increased level of miR101c was further validated by RT-PCR (FIGS. 8A, H). The administration of NAC effectively reduced the overexpression of miR101c in HSCs from hypercholesterolemic mice (FIGS. 8A, H). Transfection of miR101c mimics in HSCs from WT mice significantly repressed Tet1 expression (FIGS. 8B, C), while transfection of miR101c inhibitors in HSCs from ApoE$^{-/-}$ mice significantly increased Tet1 expression (FIGS. 8D, E). To show the direct interaction between miR101c and Tet1, we cloned the mouse Tet1 3'UTR regions that contain predicted miR101c binding sites and determined luciferase activity in HEK293T cells transfected with miR101c mimics. MiR101c significantly repressed luciferase activity in cells transfected with the constructs containing the predicted miR101c binding sites in the Tet1 3'UTR regions. In contrast, miR101c failed to alter luciferase activity when we mutated the Tet1 binding sites, thereby confirming that Tet1 is the direct binding target of miR101c (FIG. 8F). These findings represent the first known effects of miR101c on gene expression in vivo.

Example 8. Tet1 Directly Induces the Expression of Genes Critical for HSC Differentiation Towards NKT and γδT Cells Although the molecular mechanism underlying the differentiation and maturation of NKT and γδ T cells is still incompletely characterized, a group of genes that have been shown to mediate the differentiation and maturation of NKT and γδ T cells have been identified (Matsuda, J L. Et al. 2005; Garbe, A. et al. 2007). In order to determine the mechanism by which hypercholesterolemia-induced downregulation of Tet1 impairs differentiation of HSCs towards NKT and γδ T cells, we examined the expression and epigenetic regulation of genes necessary for NKT and γδ T cell specification (Table 1; The genes in bold showed significant changes).

TABLE 1

Genes related to the differentiation of NKT and γδT cells

| Genes related to NKT cell differentiation | Genes related to γδ T cell differentiation |
|---|---|
| Interleukin-2 receptor β (IL-2Rb) | B-cell lymphoma/leukemia 11B (BCL11b) |
| Interleukin-15 receptor (IL-15R) | Early growth response protein 2 (EGR2) |
| E26 Transformation specific transcription factor 1 (Ets1) | Ets variant 5 (ETV5) |
| myeloid Elf-1-like factor (MEF) | inhibitor of DNA binding protein 2 (ID2) |
| Interferon regulatory factor 1 (IRF-1) | inhibitor of DNA binding protein 3 (ID3) |
| Fyn | interleukin-2-inducible T-cell kinase (ITK) |
| | interleukin 7 receptor (IL-7R) |
| interleukin-2-inducible T-cell kinase (Itk) | |
| Activator protein-1 (AP-1) | Interleukine-15 receptor (IL-15R) |
| T cell factor 1 (TCF-1) | PHD finger protein 1 (PHF1) |
| Nuclear factor κB p50 (NFκb) | SLAM-Associated Protein (SAP, SH2D1a) |
| RELb | Sry-related HMG box 13 (Sox13) |
| IκB kinase 2 (IKK2) | T cell factor 12 (TCF12) |
| Protein kinase C-θ (PKCθ) | Zinc finger and BTB domain-containing protein 16 (ZBTB16) |
| Signaling lymphocytic activation molecule F1 (SLAMF1) | 1. |
| signaling lymphocytic activation molecule-associated protein (SAP) | 2. |
| Krüppel-like factor 2 (KLF2) | 3. |
| CCR9 | 4. |

Figure 9A:
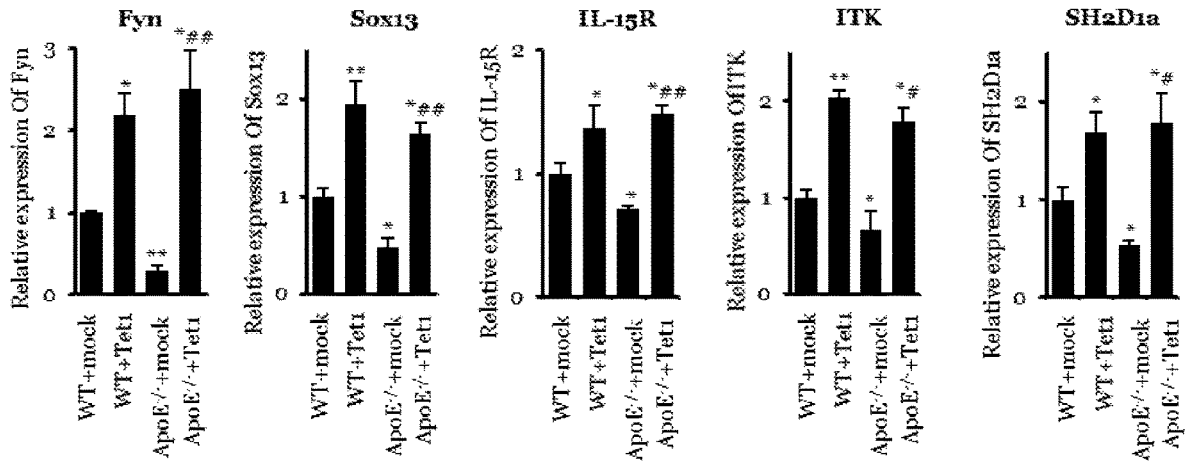
FIGS. 9A-D. Tet1 regulates the expression of the key regulatory genes in the differentiation of NKT and γδT cells. A, Gene expression in cells from with WT HSCs, ApoE$^{-/-}$ HSCs, Tet1 overexpressing WT HSCs or Tet1 overexpressing ApoE$^{-/-}$ HSCs. n=4, *, p<0.05, **, p<0.01, vs. WT+mock; #, p<0.05, ##, p<0.01, vs. ApoE$^{-/-}$+mock. B, DNA methylation status of the genes analyzed in A. n=4, *, p<0.05, **, p<0.01, vs. WT+mock; #, p<0.05, ##, p<0.01, vs. ApoE$^{-/-}$+mock. C, Gene expression analysis in WT HSCs, ApoE$^{-/-}$ HSCs, Tet1 overexpressing WT HSCs and Tet1 overexpressing ApoE$^{-/-}$ HSCs. n=4, *, p<0.05, **, p<0.01, vs. WT+mock; #, p<0.05, ##, p<0.01, vs. ApoE$^{-/-}$+mock. D, DNA methylation status of the genes analyzed in c. n=4, *, p<0.05, **, p<0.01, vs. WT+mock; #, p<0.05, ##, p<0.01, vs. ApoE$^{-/-}$+mock.

Among the genes screened, only five genes, Fyn, Sox13, IL-15R, ITK and SH2D1a, had lower expression in ApoE$^{-/-}$ HSCs than in WT HSCs (FIG. 9A). Moreover, the expression of these genes increased when Tet1 was overexpressed in HSCs from WT and hypercholesterolemic mice (FIG. 9A,C), thereby indicating a repression of the genes essential for NKT and γδ T differentiation in HSCs from hypercholesterolemic mice.

Figure 9B:
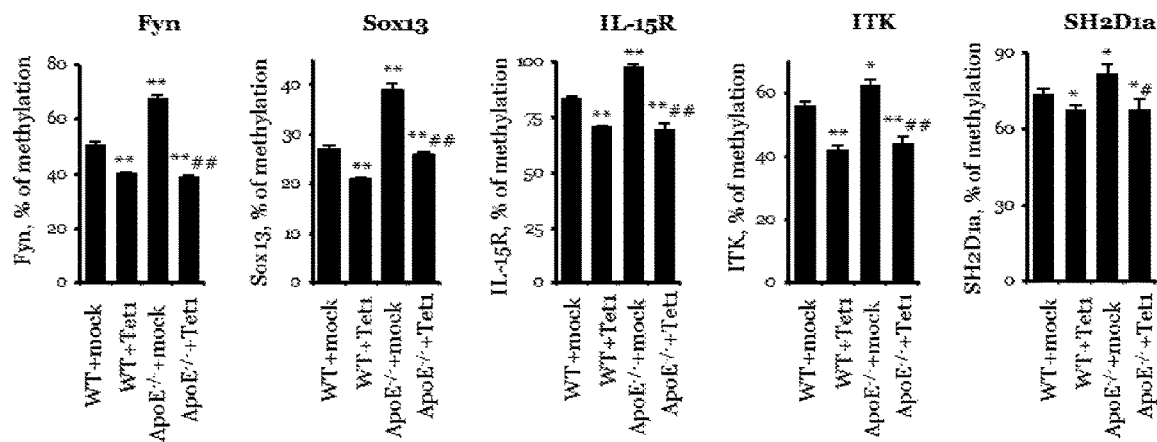
Figure 9C:
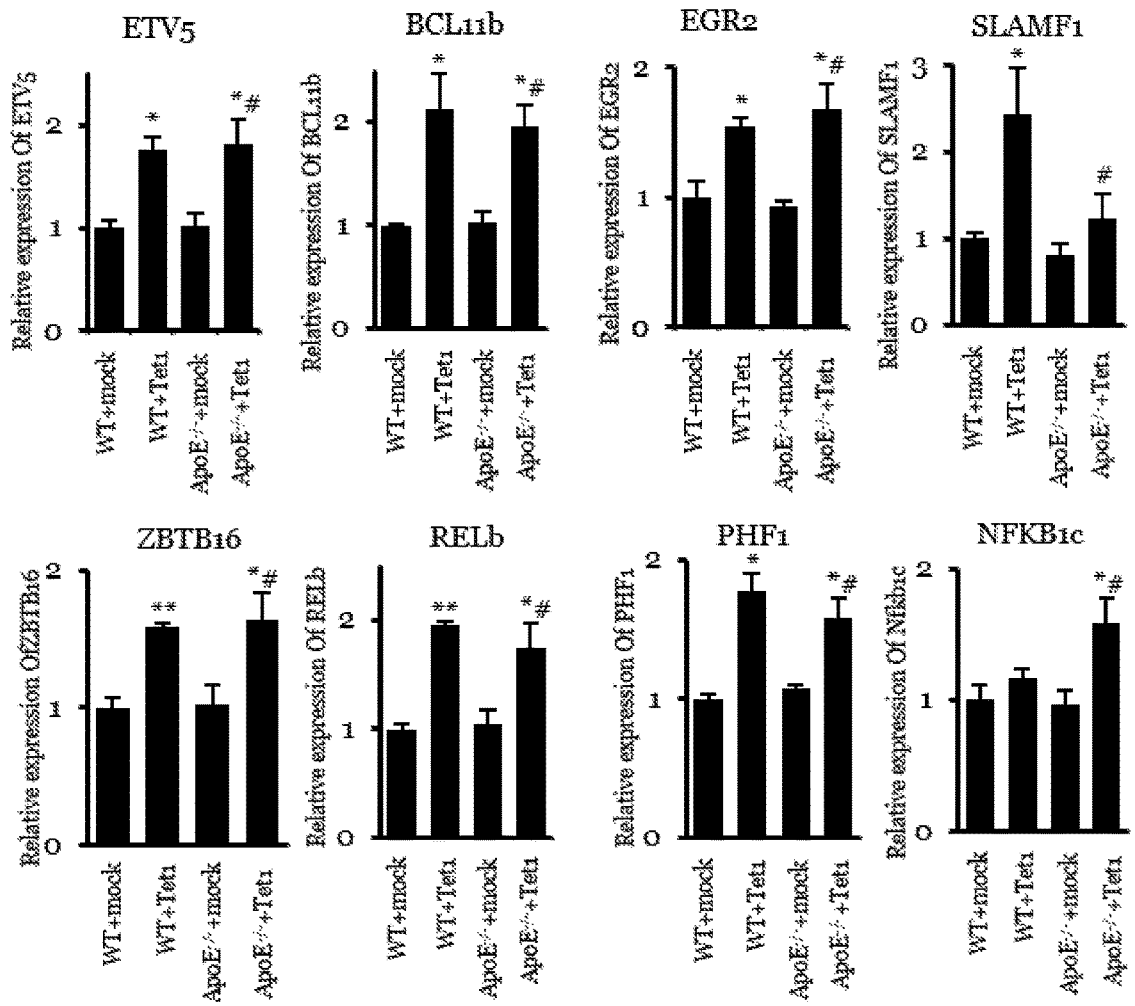
Figure 9D:
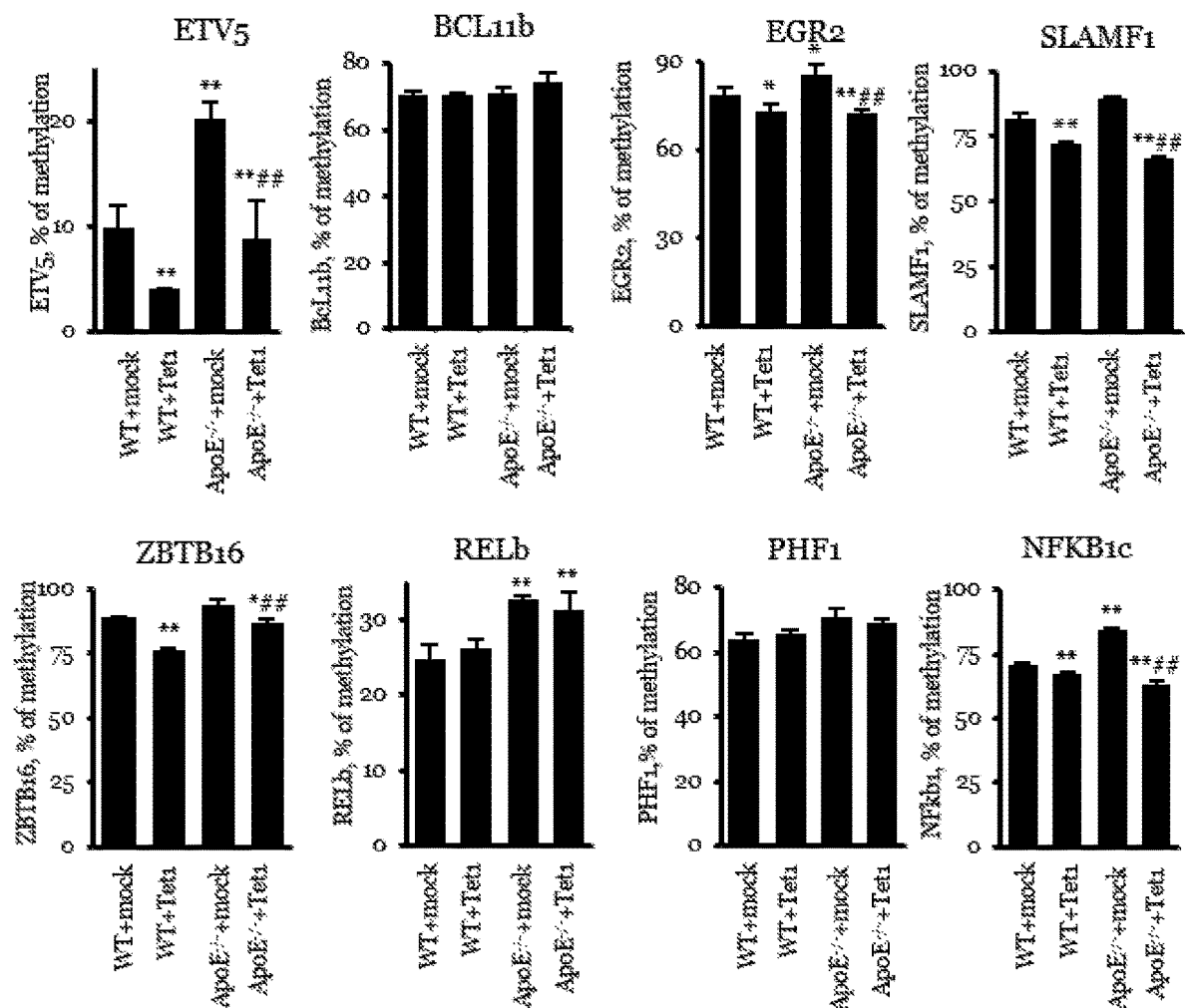

Since Tet dependent DNA demethylation typically increases the transcription of target genes (Ko, M. et al. 2011; Wu, H. et al. 2011) we next sought to characterize the changes in DNA methylation at the regulatory regions of the five genes whose expression was reduced in ApoE$^{-/-}$ mice. Pyrosequencing analysis showed that Fyn, Sox13, IL-15R, ITK and SH2D1a were more hypermethylated in ApoE$^{-/-}$ HSCs than in WT HSCs (FIG. 9B). In contrast, overexpression of Tet1 in HSCs from WT and hypercholesterolemic mice significantly decreased the methylation and correspondingly increased the expression of these genes in both WT and ApoE$^{-/-}$ HSCs (FIGS. 9B, D). Interestingly, several genes (ETV5, EGR2, SLAMF1, ZBTB16, and RELb) whose expression did not change significantly in ApoE$^{-/-}$ HSCs were also increased after overexpression of Tet1 in HSCs of both WT and ApoE$^{-/-}$ mice (FIG. 9C), suggesting that Tet1 overexpression to levels higher than those found in WT HSCs can increase the expression of genes required for NKT and γδ T specification. This is also consistent with the many salutatory effects noted above about the effects of overexpression of Tet1 WT HSCS. Consistent with this possibility, methylation of ETV5, EGR2 and NFKB1c was significantly higher in cells derived from ApoE$^{-/-}$ HSCs than those from WT HSCs, and this hypermethylation was reduced to levels at or below WT upon overexpression of Tet1 (FIG. 9D). Taken together, these results show that Tet1 directly activates genes required for NKT and γδ T specification, and this activation is impaired upon Tet1 downregulation in hypercholesterolemic HSCs.

Figure 10A:
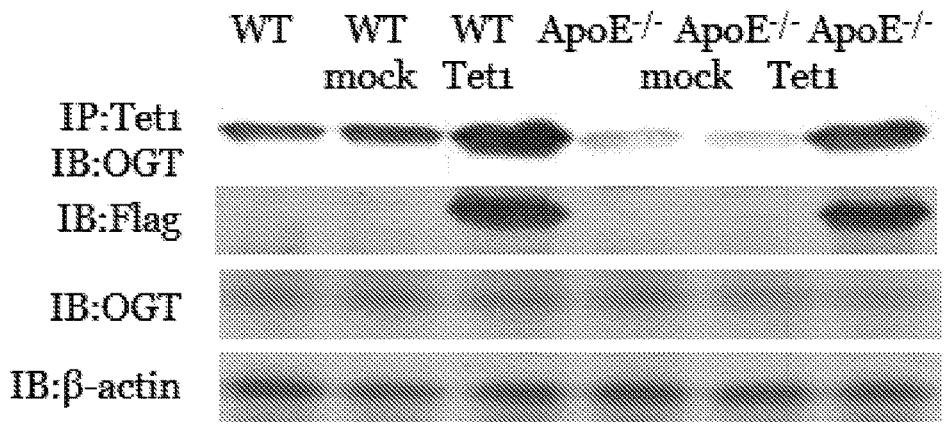
FIGS. 10A-C. Tet1 regulates H3K4me3 modification of the key regulatory genes in the differentiation of HSCs towards NKT and γδT cells in vitro. A, Detection of the expression of Tet1 and its association with OGT. Immunoprecipitation was performed with WT HSCs, ApoE$^{-/-}$ HSCs, Tet1 overexpressing WT HSCs or Tet1 overexpressing ApoE$^{-/-}$ HSCs. B, Detection of the expression of Tet3 and its association with OGT. C, H3K4me3 modification of the key regulatory genes in the differentiation of HSCs towards NKT and γδT cells in vitro. n=4, *, p<0.05, **, p<0.01, vs. WT+mock; #, p<0.05, ##, p<0.01, vs. ApoE$^{-/-}$+mock.
Figure 10B:
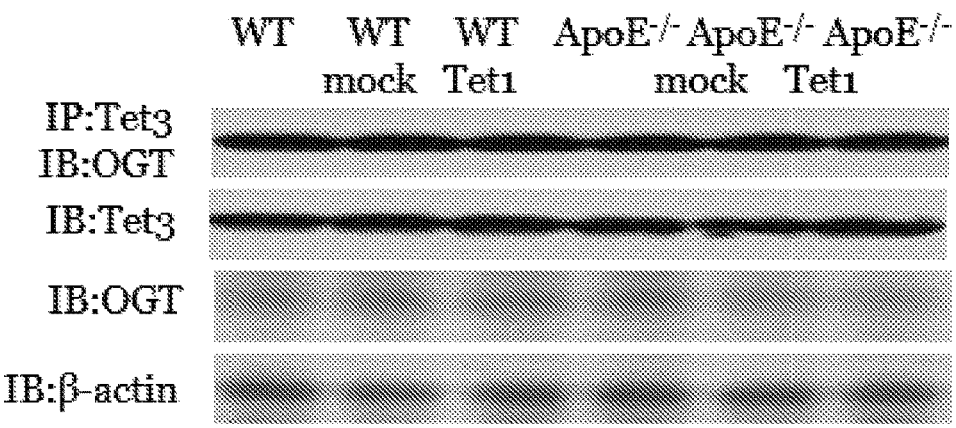
Figure 10C:
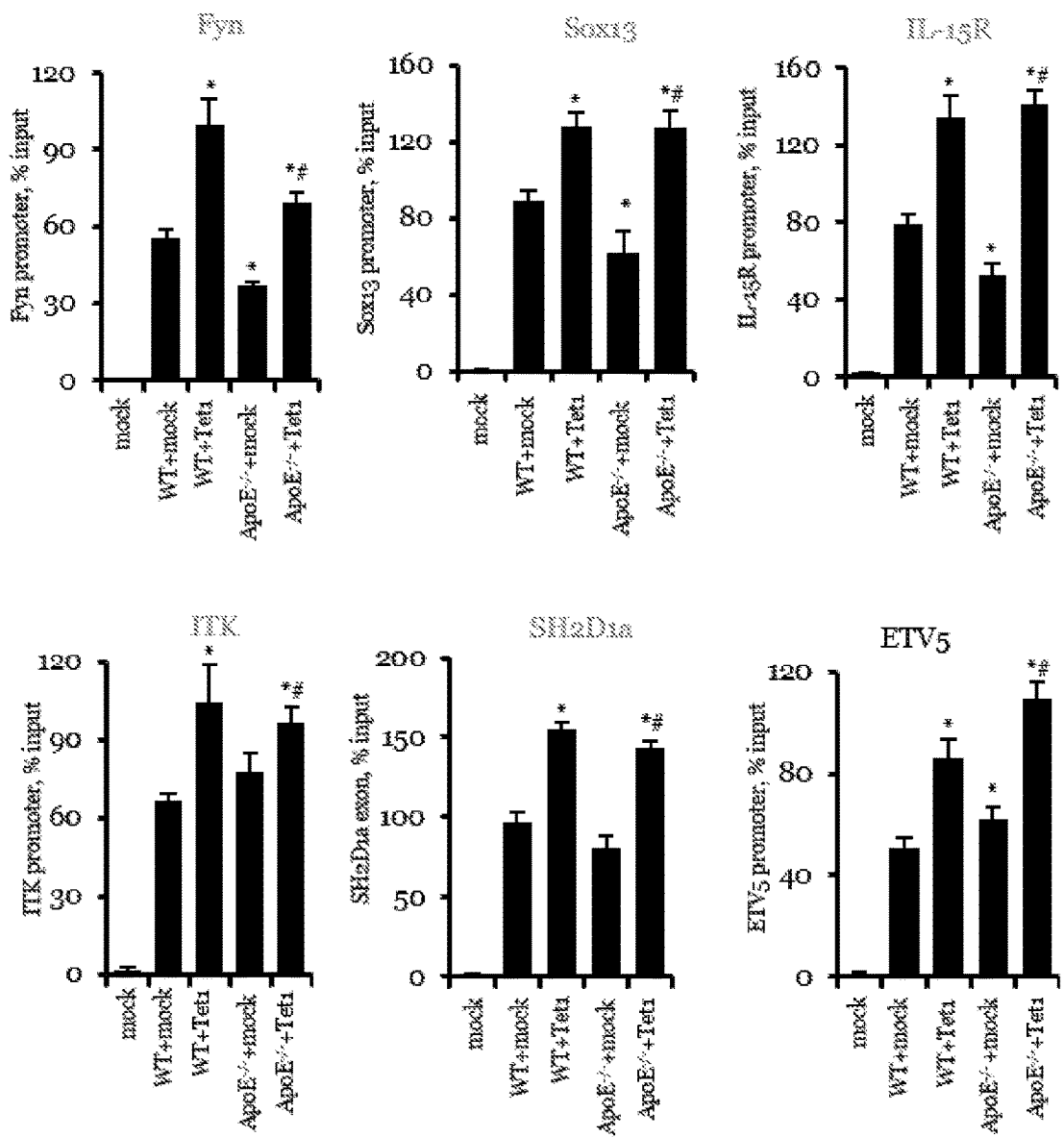
Figure 10C:
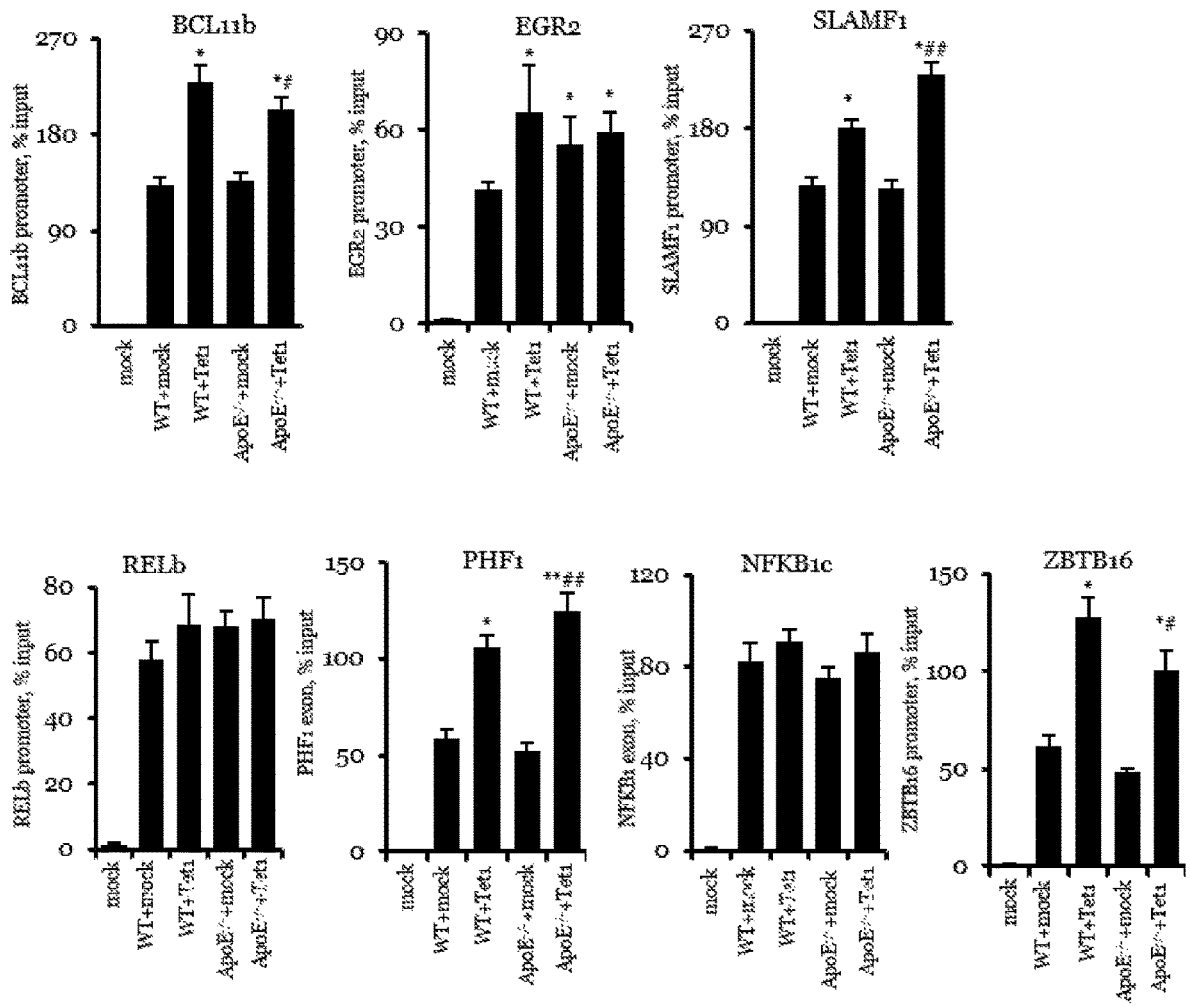

Recent studies indicate that Tet proteins may also participate in the regulation of histone modifications via distinct pathways. The O-linked N-acetylglucosamine (O-GlaNAc) transferase OGT is an evolutionarily conserved enzyme that catalyzes O-linked protein glycosylation. Tet proteins were identified as stable partners of OGT in the nucleus (Vella, P. et al. 2013; Chen, Q. et al. 2013; Shi, F T. et al. 2013). The interaction of Tet2 and Tet3 with OGT leads to the GlcNAcylation of Host Cell Factor 1 and contributes to the integrity of the H3K4 methyltransferase SET1/COMPASS complex, revealing that Tet proteins increase the level of H3K4me3, a modification that functions in transcriptional activation (Deplus, R. et al. 2013). Although an early observation showed that the interaction between Tet1 and OGT was limited to embryonic stem cells, our immunoprecipitation studies show that OGT also interacts with Tet1 in HSCs (FIG. 10A). In accordance with the decrease in Tet1 expression, the Tet1-OGT interaction was significantly reduced in HSCs isolated from hypercholesterolemic mice. The overexpression of Tet1 significantly increased the interaction of Tet1 and OGT, but did not influence the expression or interaction of Tet3 and OGT in the cells (FIGS. 10A, B). Consistent with these findings, overexpression of Tet1 caused an increase of H3K4me3 methylation near the promoters of all genes investigated, except RELb and NFKB1. The results suggest that, by interacting with OGT, Tet1 also increases histone H3K4me3 levels and maintains active chromatin structure near many of the genes critical for the differentiation of HSCs towards NKT and γδT cells (FIG. 10C). Consequently, Tet1 promotes the expression of genes driving NKT and γδT specification by multiple mechanisms.

Figure 11A:
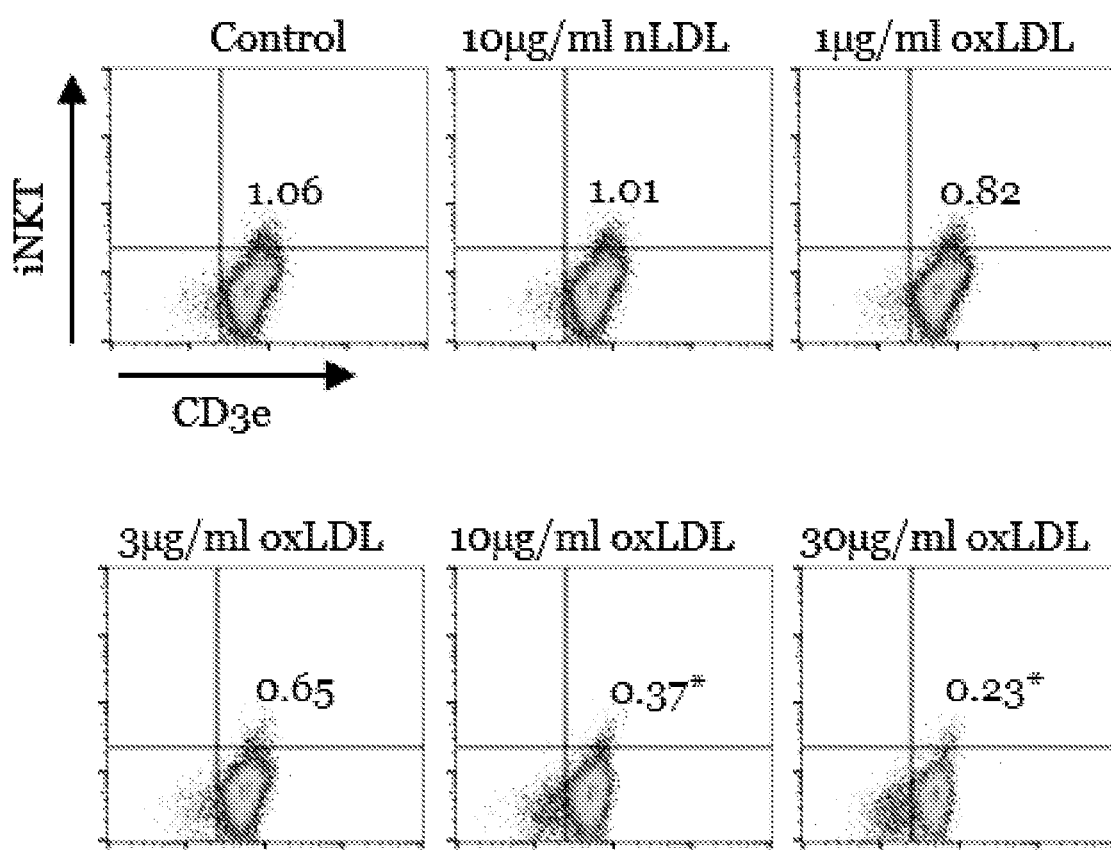
FIGS. 11A-C. OxLDL impairs the differentiation of human HSCs towards NKT and γδ T cells in vitro. A, Differentiation of human HSCs towards iNKT cells in vitro. B, Differentiation of human HSCs towards γδT cells in vitro. C, Relative expression of Tet1 in human HSCs treated with oxLDL. n=3, *, p<0.05, vs. control.
Figure 11B:
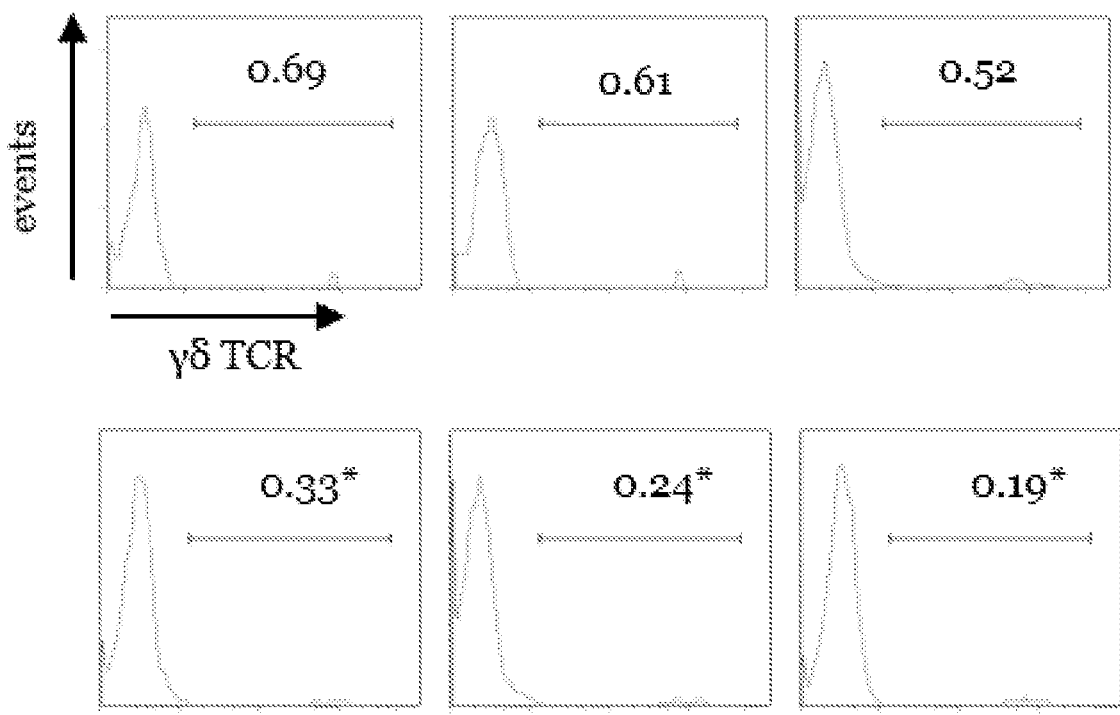
Figure 11C:
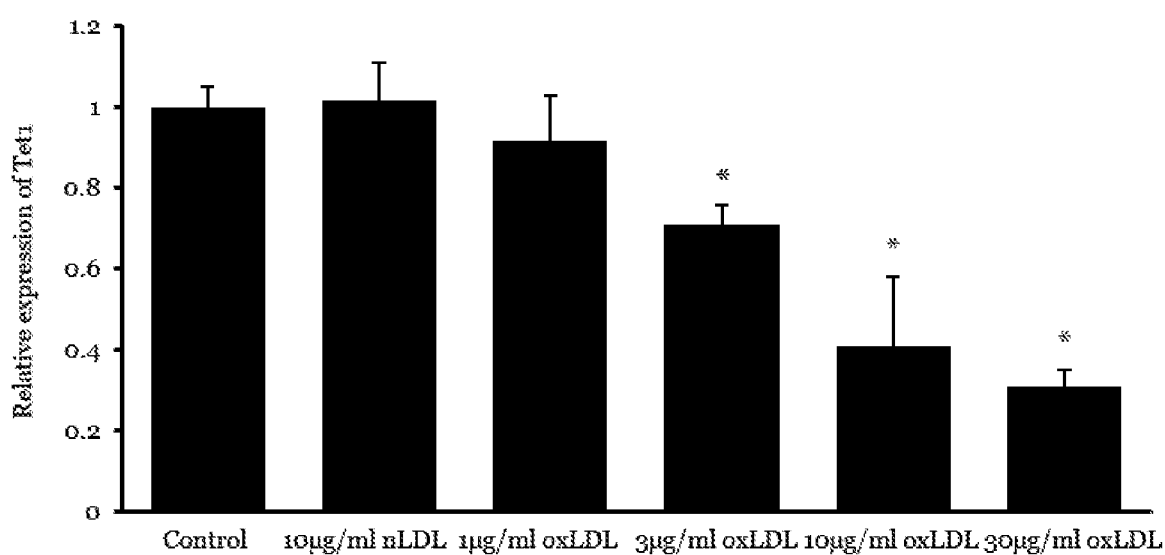

Example 9. Hypercholesterolemia Also Downregulates Tet1 Expression in Human HSCs and Impairs their Differentiation Towards NKT and γδ T Cells To test whether these findings in mouse models of hypercholesterolemia were applicable to human HSCs, we employed the same in vitro differentiation assay used in the mouse experiments. Human HSCs were exposed to oxLDL, the primary source of oxidant stress in the HSCs of hypercholesterolemic mice (Tie, G. et al. 2014) and their differentiation capacities towards NKT and γδ T cells were examined. We observed an oxLDL concentration dependent decrease in the differentiation of human HSCs towards NKT and γδ T cells (FIGS. 11A, B). Congruent with our mouse studies, the treatment with oxLDL inhibited Tet1 expression in human HSCs in a dose dependent manner (FIG. 11C). Thus, these results in human HSCs are parallel to those in hypercholesterolemic mice, suggesting that these findings may be generalizable to humans.

REFERENCES

Koene R J, Prizment A E, Blaes A, Konety S H. Shared Risk Factors in Cardiovascular Disease and Cancer. *Circulation.* 2016; 133:1104-14.

Hennekens C H, Andreotti F. Leading avoidable cause of premature deaths worldwide: case for obesity. *Am J Med* 2013; 126:97-8.

Font-Burgada J, Sun B, Karin M. Obesity and Cancer: The Oil that Feeds the Flame. *Cell Metab* 2016; 23:48-62.

Notarnicola M, Altomare D F, Correale M, Ruggieri E, D'Attoma B, Mastrosimini A, Guerra V, Caruso M G. serum lipid profile in colorectal cancer patients with and without synchronous distant metastases. *Oncology* 2005; 68:371-374.

Drechsler M, Megens R T, van Zandvoort M, Weber C, Soehnlein O. Hyperlipidemia-triggered neutrophilia promotes early atherosclerosis. *Circulation* 2010; 122:1837-1845.

Klingenberg R, Gerdes N, Badeau R M, Gistera A, Strodthoff D, Ketelhuth D F, Lundberg A M, Rudling M, Nilsson S K, Olivecrona G, Zoller S, Lohmann C, Luscher T F, Jauhiainen M, Sparwasser T, Hansson G K. Depletion of FOXP3+ regulatory T cells promotes hypercholesterolemia and atherosclerosis. *J Clin Invest* 2013; 123:1323-1334.

Sag D, Wingender G, Nowyhed H, Wu R, Gebre A K, Parks J S, Kronenberg M, Hedrick C C. ATP-binding cassette transporter Gi intrinsically regulates invariant NKT cell development. *J Immunol.* 2012; 189:5129-5138.

Sag D, Cekic C, Wu R, Linden J, Hedrick C C. The cholesterol transporter ABCG1 links cholesterol homeostasis and tumour immunity. *Nat Commun* 2015; 6:6354.

van Galen P, Kreso A, Wienholds E, Laurenti E, Eppert K, Lechman E R, Mbong N, Hermans K, Dobson S, April C, Fan J B, Dick J E. Reduced lymphoid lineage priming promotes human hematopoietic stem cell expansion. *Cell Stem Cell* 2014; 14:94-106.

Guo G, Luc S, Marco E, Lin T W, Peng C, Kerenyi M A, Beyaz S, Kim W, Xu J, Das P P, Neff T, Zou K, Yuan G C, Orkin S H. Mapping cellular hierarchy by single-cell analysis of the cell surface repertoire. *Cell Stem Cell* 2013; 13:492-505.

Mercer E M, Lin Y C, Benner C, Jhunjhunwala S, Dutkowski J, Flores M, Sigvardsson M, Ideker T, Glass C K, Murre C. Multilineage priming of enhancer repertoires precedes commitment to the B and myeloid cell lineages in hematopoietic progenitors. *Immunity* 2011; 35:413-425.

Orkin S H. Priming the hematopoietic pump. *Immunity* 2003; 19:633-4.

Tie G, Messina K E, Yan J, Messina J A, Messina L M. Hypercholesterolemia induces oxidant stress that accelerates the ageing of hematopoietic stem cells. *J Am Heart Assoc.* 2014; 3:e000241.

Greten F R, Eckmann L, Greten T F, Park J M, Li Z W, Egan L J, Kagnoff M F, Karin M. IKKbeta links inflammation and tumorigenesis in a mouse model of colitis-associated cancer. *Cell* 2004; 118:285-96.

Schmitt T M, de Pooter R F, Gronski M A, Cho S K, Ohashi P S, Zniga-Pflücker J C. Induction of T cell development and establishment of T cell competence from embryonic stem cells differentiated in vitro. *Nat Immunol* 2004; 5:410-7.

Nunez-Cruz S, Yeo W C, Rothman J, Ojha P, Bassiri H, Juntilla M, Davidson D, Veillette A, Koretzky G A, Nichols K E. Differential requirement for the SAP-Fyn interaction during N K T cell development and function. *J Immunol* 2008; 181:2311-20.

Chien Y H, Meyer C, Bonneville M. γδ T cells: first line of defense and beyond. *Annu Rev Immunol.* 2014; 32:121-55.

Taniguchi M, Seino K, Nakayama T. The NKT cell system: bridging innate and acquired immunity. *Nat Immunol* 2003; 4:1164-5.

Todaro M, D'Asaro M, Caccamo N, Iovino F, Francipane M G, Meraviglia S, Orlando V, La Mendola C, Gulotta G, Salerno A, Dieli F, Stassi G. Efficient killing of human colon cancer stem cells by gammadelta T lymphocytes. *J Immunol* 2009; 182:7287-96.

Ito S, D'Alession A C, Taranova O V, Hong K, Sowers L C, Zhang Y. Role of Tet proteins in 5 mC to 5 hmC conversion, E S-cell self-renewal and inner cell mass specification. *Nature* 2010; 466:1129-33.

Ko M, Huang Y, Jankowska A M, Pape U J, Tahiliani M, Bandukwala H S, An J, Lamperti E D, Koh K P, Ganetzky R, Liu X S, Aravind L, Agarwal S, Maciejewski J P, Rao A. Impaired hydroxylation of 5-methylcytosine in myeloid cancers with mutant TET2. *Nature* 2010; 468: 839-43.

Ito S, Shen L, Dai Q, Wu S C, Collins L B, Swenberg J A, He C, Zhang Y. Tet proteins can convert 5-methylcytosine to 5-formylcytosine and 5-carboxylcytosine. *Science* 2011; 333:1300-3.

Ko M, Bandukwala H S, An J, Lamperti E D, Thompson E C, Hastie R, Tsangaratou A, Rajewsky K, Koralov S B, Rao A. Ten-Eleven-Translocation 2 (TET2) negatively regulates homeostasis and differentiation of hematopoietic stem cells in mice. *Proc Natl Acad Sci USA.* 2011; 108:14566-71.

Corpuz T M, Stolp J, Kim H O, Pinget G V, Gray D H, Cho J H, Sprent J, Webster K E. Differential Responsiveness of Innate-like IL-17- and IFN-γ-Producing γδ T Cells to Homeostatic Cytokines. *J Immunol* 2016; 196:645-54.

Shibata S, Tada Y, Hau C S, Mitsui A, Kamata M, Asano Y, Sugaya M, Kadono T, Masamoto Y, Kurokawa M, Yamauchi T, Kubota N, Kadowaki T, Sato S. Adiponectin regulates psoriasiform skin inflammation by suppressing IL-17 production from γδ-T cells. *Nat Commun.* 2015; 6:7687.

Wilson R P, Ives M L, Rao G, Lau A, Payne K, Kobayashi M, Arkwright P D, Peake J, Wong M, Adelstein S, Smart J M, French M A, Fulcher D A, Picard C, Bustamante J, Boisson-Dupuis S, Gray P, Stepensky P, Warnatz K, Freeman AF17, Rossjohn J, McCluskey J, Holland S M, Casanova J L, Uzel G, Ma C S, Tangye S G, Deenick E K. STAT3 is a critical cell-intrinsic regulator of human unconventional T cell numbers and function. *J Exp Med.* 2015; 212:855-64.

Zarin P, Chen E L, In T S, Anderson M K, Zniga-Pflucker J C. Gamma delta T-cell differentiation and effector function programming, TCR signal strength, when and how much? *Cell Immunol.* 2015; 296:70-5.

Matsuda J L, Gapin L. Developmental program of mouse Valpha14i NKT cells. *Curr Opin Immunol* 2005; 17:122-30.

Garbe A, von Boehmer H. TCR and Notch synergize in alphabeta versus gammadelta lineage choice. *Trends Immunol* 2007; 28:124-31.

Wu H, Zhang Y. Mechanisms and functions of Tet protein-mediated 5-methylcytosine oxidation. *Genes Dev* 2011; 25:2436-52.

Vella P, Scelfo A, Jammula S, Chiacchiera F, Williams K, Cuomo A, Roberto A, Christensen J, Bonaldi T, Helin K, Pasini D. Tet proteins connect the O-linked N-acetylglucosamine transferase Ogt to chromatin in embryonic stem cells. *Mol Cell.* 2013; 49:645-56.

Chen Q, Chen Y, Bian C, Fujiki R, Yu X. TET2 promotes histone O-GlcNAcylation during gene transcription. *Nature.* 2013; 493:561-4.

Shi F T, Kim H, Lu W, He Q, Liu D, Goodell M A, Wan M, Songyang Z. Ten-eleven translocation 1 (Tet1) is regulated by O-linked N-acetylglucosamine transferase (Ogt) for target gene repression in mouse embryonic stem cells. *J Biol Chem* 2013; 288:20776-84.

Deplus R, Delatte B, Schwinn M K, Defrance M, Mendez J, Murphy N, Dawson M A, Volkmar M, Putmans P, Calonne E, Shih A H, Levine R L, Bernard O, Mercher T, Solary E, Urh M, Daniels D L, Fuks F. TET2 and TET3 regulate GlcNAcylation and H3K4 methylation through OGT and SET1/COMPASS. *EMBO J* 2013; 32:645-55.

Cimmino L, Dawlaty M M, Ndiaye-Lobry D, Yap Y S, Bakogianni S, Yu Y, Bhattacharyya S, Shaknovich R, Geng H, Lobry C, Mullenders J, King B, Trimarchi T, Aranda-Orgilles B, Liu C, Shen S, Verma A K, Jaenisch R, Aifantis I. TET1 is a tumor suppressor of hematopoietic malignancy. *Nat Immunol* 2015; 16:653-62.

Chapman C G, Mariani C J, Wu F, Meckel K, Butun F, Chuang A, Madzo J, Bissonette M B, Kwon J H, Godley L A. TET-catalyzed 5-hydroxymethylcytosine regulates gene expression in differentiating colonocytes and colon cancer. *Sci Rep.* 2015; 5:17568.

Frank B, Marcu A, de Oliveira Almeida Petersen A L, Weber H, Stigloher C, Mottram J C, Scholz C J, Schurigt U. Autophagic digestion of *Leishmania major* by host macrophages is associated with differential expression of BNIP3, CTSE, and the miRNAs miR-101c, miR-129, and miR-210. *Parasit Vectors.* 2015; 8:404.

Dunn G P, Bruce A T, Ikeda H, Old L J, Schreiber R D. Cancer immunoediting: from immunosurveillance to tumor escape. *Nat Immunol.* 2002; 3:991-998.

Vantourout P, Hayday A. Six-of-the-best: unique contributions of γδ T cells to immunology. *Nat Rev Immunol* 2013; 13:88-100.

Strid J, Roberts S J, Filler R B, Lewis J M, Kwong B Y, Schpero W, Kaplan D H, Hayday A C, Girardi M. Acute upregulation of an NKG2D ligand promotes rapid reorganization of a local immune compartment with pleiotropic effects on carcinogenesis. *Nat Immunol* 2008; 9:146-154.

Bendelac A, Savage P B, Teyton L. The biology of NKT cells. *Annu Rev Immunol* 2007; 25:297-336.

Dhodapkar M V, Geller M D, Chang D H, Shimizu K, Fujii S, Dhodapkar K M, Krasovsky J. A reversible defect in natural killer T cell function characterizes the progression of premalignant to malignant multiple myeloma. *J Exp Med.* 2003; 197:1667-76.

Themeli M, Kloss C C, Ciriello G, Fedorov V D, Perna F, Gonen M, Sadelain M. Generation of tumor-targeted human T lymphocytes from induced pluripotent stem cells for cancer therapy. *Nat Biotechnol.* 2013; 31:928-33.

Galon et al., Cancer classification using the Immunoscore: a worldwide task force. *J Transl Med.* 2012; 10:205-214.

Li L, Li C, Mao H, Du Z, Chan W Y, Murray P, et al. Epigenetic inactivation of the CpG demethylase TET1 as a DNA methylation feedback loop in human cancers. *Sci Rep* 2016; 6: 26591.

Neri F, Dettori D, Incarnato D, Krepelova A, Rapelli S, Maldotti M, et al. TET1 is a tumour suppressor that inhibits colon cancer growth by derepressing inhibitors of the WNT pathway. Oncogene 2015; 34: 4168-76.

Santos, B Serre, K, Norell, H. γδ T cells in cancer. Nature Reviews Vol. 15 Nov. 2015 883-89.

Bollino, D Webb, T. Chimeric antigen receptor-engineered natural killer and natural killer T cells for cancer. Immunotherapy. Translational Research 2017; 187:32-43

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating colorectal cancer that has elevated levels of miR-101-3p in a subject, the method comprising administering to the subject a therapeutically effective amount of (i) a miR-101-3p inhibitory nucleic acid, or (ii) hematopoietic stem cells (HSCs) expressing a miR-101-3p inhibitory nucleic acid, wherein the miR-101-3p inhibitory nucleic acid is an antisense molecule, a small interfering RNA, an antagomir, or a small hairpin RNA comprising a sequence that is complementary to a contiguous sequence of at least 12-30 nucleotides present in miR-101-3p and wherein the miR-101-3p inhibitory nucleic acid increases levels of Ten-eleven translocation methylcytosine dioxygenase 1 (Tet1).

2. The method of claim 1, wherein the miR-101-3p inhibitory nucleic acid is an oligonucleotide.

3. The method of claim 1, wherein the miR-101-3p inhibitory nucleic acid targets a nucleic acid encoding SEQ ID NO:3.

4. The method of claim 1, wherein the subject is human.

5. The method of claim 1, wherein the subject has, or is at risk of having hypercholesterolemia.

6. The method of claim 1, further comprising administering to the subject one or more anti-cancer therapies.

7. The method of claim 6, wherein the one or more anti-cancer therapies is selected from the group consisting of surgical resection with cold instruments or lasers, radiation therapy, phototherapy, biologic therapy, radiofrequency ablation (RFA), radioembolisation, chemotherapy, and immunotherapy.

8. A method of reducing the risk of colorectal cancer that has elevated levels of miR-101-3p in a subject who has, or is at risk of having hypercholesterolemia, the method comprising administering to the subject a therapeutically effective amount of a miR-101-3p inhibitory nucleic acid, wherein the miR-101-3p inhibitory nucleic acid is an antisense molecule, a small interfering RNA, an antagomir, or a small hairpin RNA comprising a sequence that is complementary to a contiguous sequence of at least 12-30 nucleotides present in miR-101-3p and wherein the miR-101-3p inhibitory nucleic acid increases expression of Ten-eleven translocation methylcytosine dioxygenase 1 (Tet1).

9. The method of claim 8, wherein the miR-101-3p inhibitory nucleic acid is an oligonucleotide.

10. The method of claim 8, wherein the miR-101-3p inhibitory nucleic acid targets a nucleic acid encoding SEQ ID NO:3.

11. The method of claim 1, wherein the method increases the number of NKT and γδT cells in blood or within the cancer.

12. The method of claim 1, wherein the miR-101-3p inhibitory nucleic acid is an antisense molecule.

13. The method of claim 1, wherein the miR-101-3p inhibitory nucleic acid is a small interfering RNA.

14. The method of claim 1, wherein the miR-101-3p inhibitory nucleic acid is an antagomir.

15. The method of claim 1, wherein the miR-101-3p inhibitory nucleic acid is a small hairpin RNA.

16. The method of claim 8, wherein the method increases the number of NKT and γδT cells in blood.

17. The method of claim 8, wherein the miR-101-3p inhibitory nucleic acid is an antisense molecule.

18. The method of claim 8, wherein the miR-101-3p inhibitory nucleic acid is a small interfering RNA.

19. The method of claim 8, wherein the miR-101-3p inhibitory nucleic acid is an antagomir.

20. The method of claim 8, wherein the miR-101-3p inhibitory nucleic acid is a small hairpin RNA.

* * * * *

SEQUENCE LISTING

```
<160> NUMBER OF SEQ ID NOS: 3

<210> SEQ ID NO 1
<211> LENGTH: 19
<212> TYPE: RNA
<213> ORGANISM: Mus musculus

<400> SEQUENCE: 1
acaguacugu gauaacuga                                                  19

<210> SEQ ID NO 2
<211> LENGTH: 21
<212> TYPE: RNA
<213> ORGANISM: Homo sapiens
```

```
<400> SEQUENCE: 2
uacaguacug ugauaacuga a                                          21

<210> SEQ ID NO 3
<211> LENGTH: 8
<212> TYPE: RNA
<213> ORGANISM: Homo sapiens

<400> SEQUENCE: 3 acaguacu                                                          8
```